(12) United States Patent
Kashanchi et al.

(10) Patent No.: US 12,208,080 B2
(45) Date of Patent: Jan. 28, 2025

(54) COMPOSITIONS AND METHODS FOR MODULATION OF EXTRACELLULAR VESICLE RELEASE AND TREATMENT OF NEUROLOGICAL DISORDERS

(71) Applicant: GEORGE MASON RESEARCH FOUNDATION, INC., Fairfax, VA (US)

(72) Inventors: Fatah Kashanchi, Potomac, MD (US); Catherine DeMarino, Annandale, VA (US)

(73) Assignee: George Mason Research Foundation, Inc., Fairfax, VA (US)

(*) Notice: Subject to any disclaimer, the term of this patent is extended or adjusted under 35 U.S.C. 154(b) by 804 days.

(21) Appl. No.: 17/227,786

(22) Filed: Apr. 12, 2021

(65) Prior Publication Data

US 2021/0260021 A1   Aug. 26, 2021

Related U.S. Application Data

(63) Continuation-in-part of application No. PCT/US2019/056453, filed on Oct. 16, 2019.

(Continued)

(51) Int. Cl.
*A61K 31/352* (2006.01)
*A61K 31/05* (2006.01)
(Continued)

(52) U.S. Cl.
CPC ............ *A61K 31/352* (2013.01); *A61K 31/05* (2013.01); *A61K 45/06* (2013.01); *A61P 31/18* (2018.01)

(58) Field of Classification Search
CPC .... C11B 1/10; C11B 3/16; C11B 1/02; A23K 10/12; A23K 20/158; A23K 10/20; A23K 50/10; C12N 1/06
See application file for complete search history.

(56) References Cited

U.S. PATENT DOCUMENTS 4,929,442 A * 5/1990 Powell .................. A61K 38/21
424/85.4
5,093,116 A * 3/1992 Suzuki ................. A61K 38/212
514/262.1
(Continued)

FOREIGN PATENT DOCUMENTS

WO   WO-2016025010 A1 *   2/2016   ............. A61K 35/14
WO   WO-2017011785 A1 *   1/2017   ............. A61K 31/05

OTHER PUBLICATIONS

Kosgodage, et al., "Cannabiniol(CBD) is a Novel Inhibitor for Exosome and Microvesicle (EMV) Release in Cancer", Front Pharmacol 9:889, p. 1-17, 2018 (Year: 2018).*

(Continued)

*Primary Examiner* — Deborah D Carr
(74) *Attorney, Agent, or Firm* — Saul Ewing LLP; Alireza Behrooz

(57) ABSTRACT

This disclosure relates to methods and compositions for inhibiting release of extracellular vesicles from a cell infected by a virus. One aspect of the disclosure relates to methods for treating viral diseases, reducing damage to a neuron from the central neural system ("CNS") and/or treating neuroinflammation in a subject. In another aspect, provided herein are methods for inhibiting transcription of a viral RNA and/or release of extracellular vesicles from a cell infected by a virus.

18 Claims, 33 Drawing Sheets
Specification includes a Sequence Listing.

Related U.S. Application Data

(60) Provisional application No. 62/746,247, filed on Oct. 16, 2018.

(51) Int. Cl.
*A61K 45/06* (2006.01)
*A61P 31/18* (2006.01)

(56) References Cited

U.S. PATENT DOCUMENTS

2009/0028820 A1  1/2009  Ishii et al.
2010/0317566 A1* 12/2010  Bond .................. C07K 7/06
                                                 435/320.1

OTHER PUBLICATIONS

International Search Report published Apr. 23, 2020, PCT/US2019/056453.
Kosgodage, et al., "Cannabiniol (CBD) is a Novel Inhibitor for Exosome and Microvesicle (EMV) Release in Cancer", Front Pharmacol 9:889, p. 1-17—Aug. 13, 2018.

* cited by examiner

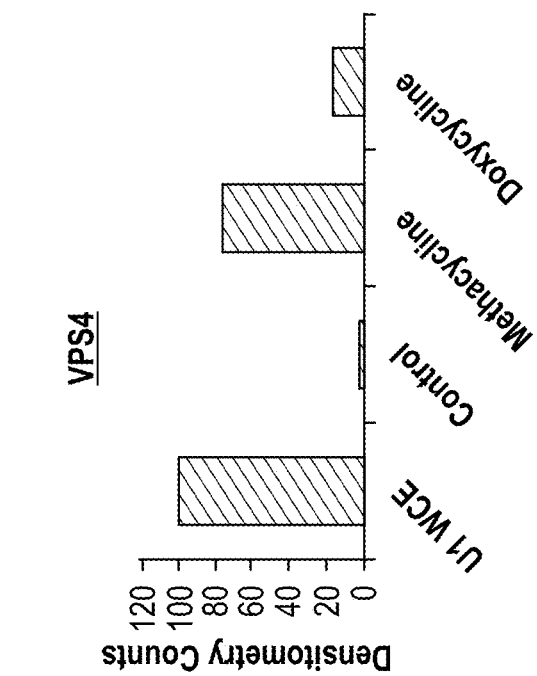
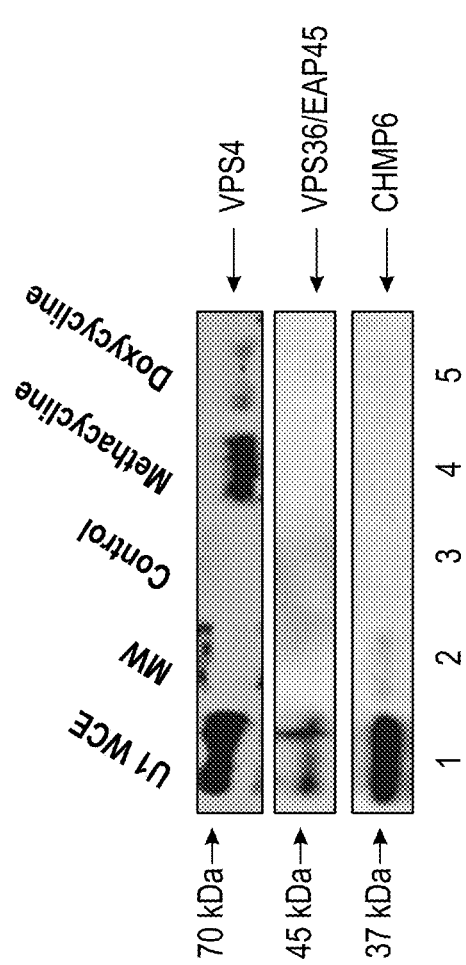
FIG. 5C

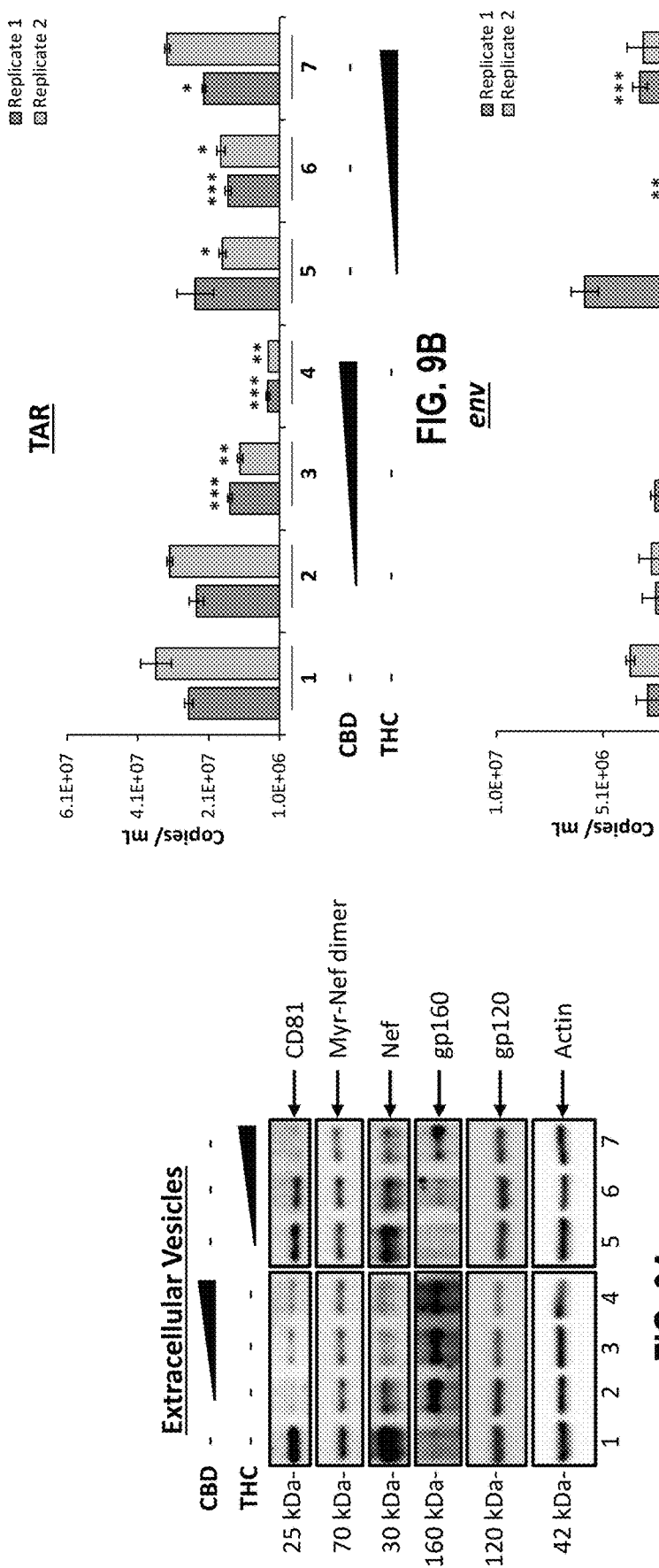

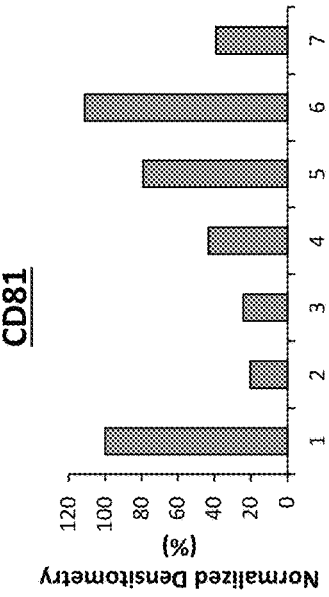
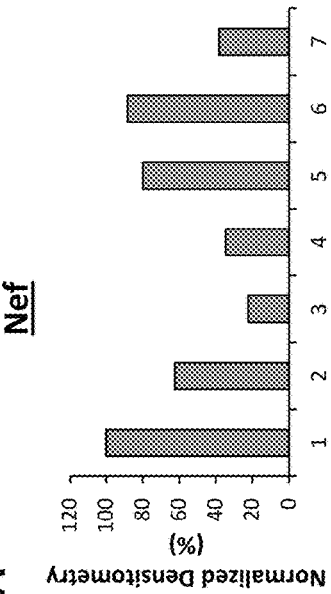
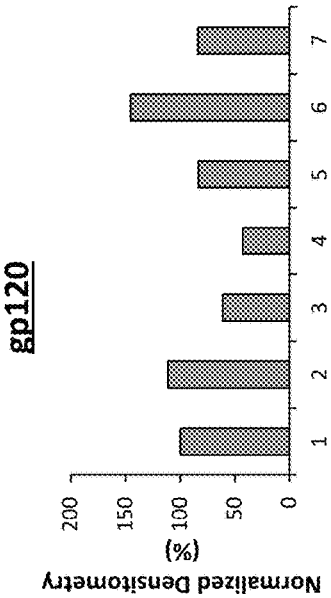
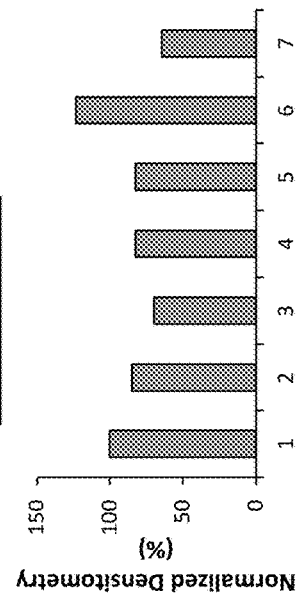
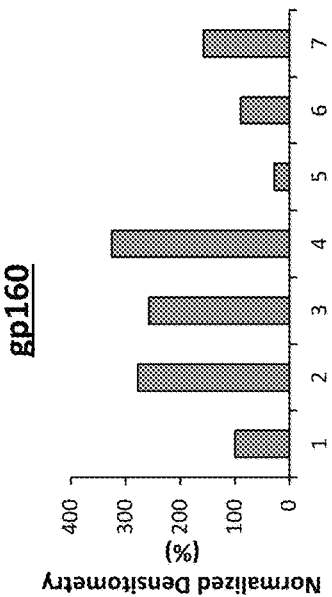

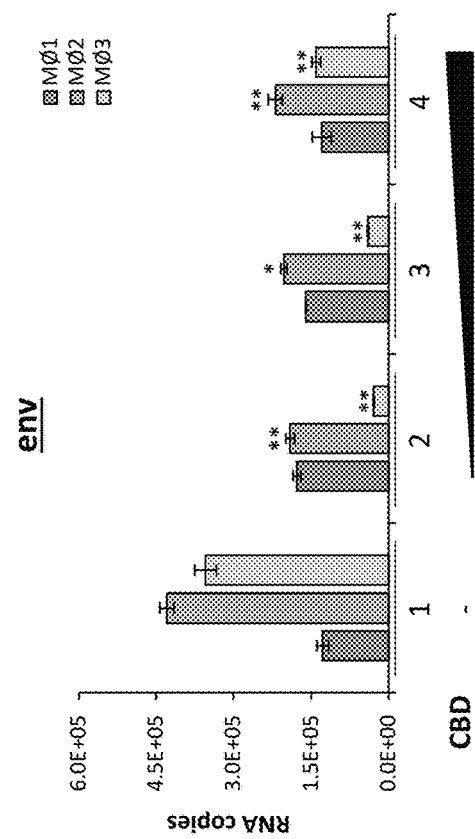
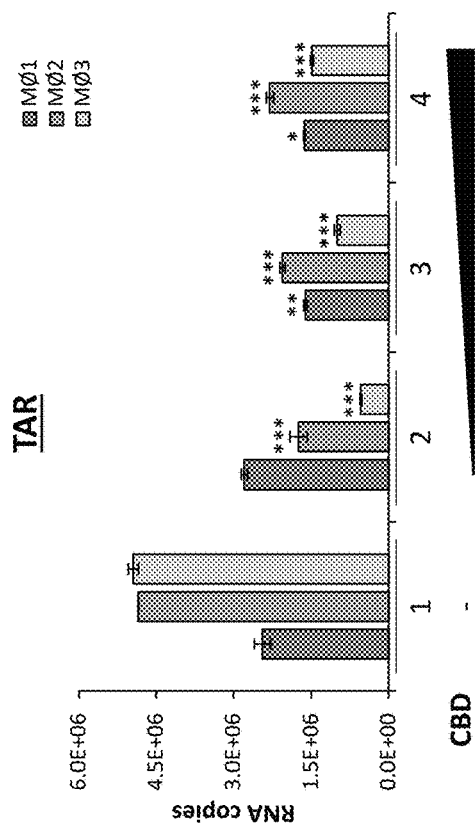
FIG. 11A
FIG. 11B

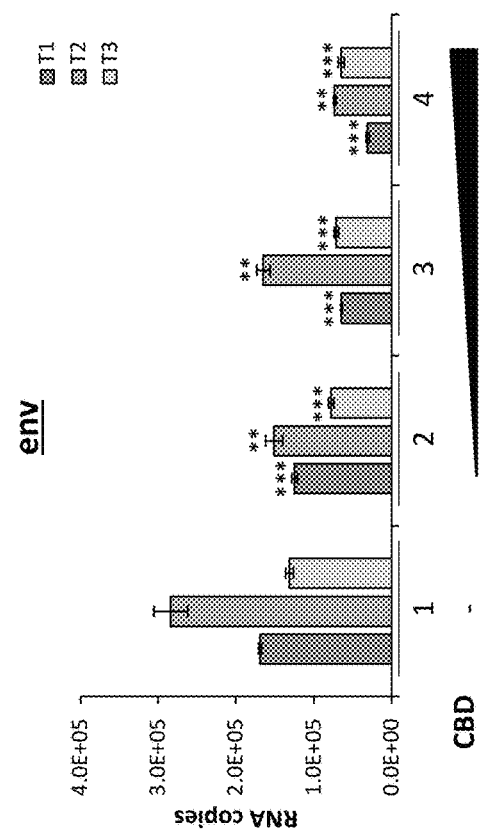
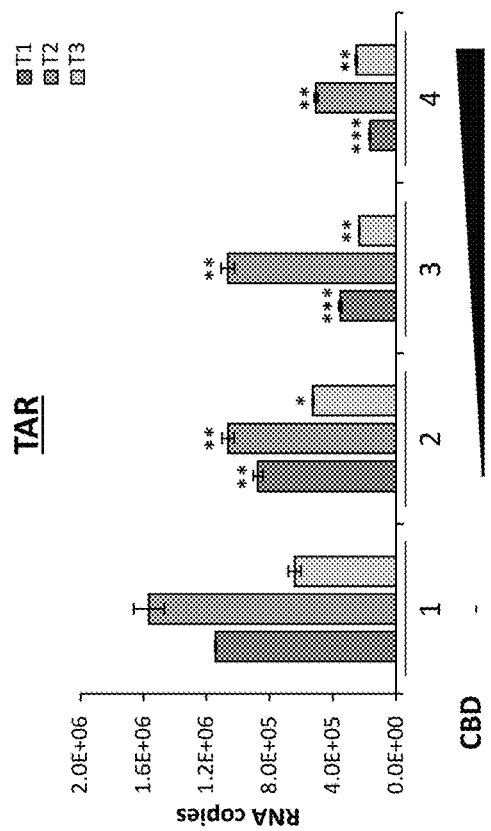
FIG. 13A
FIG. 13B

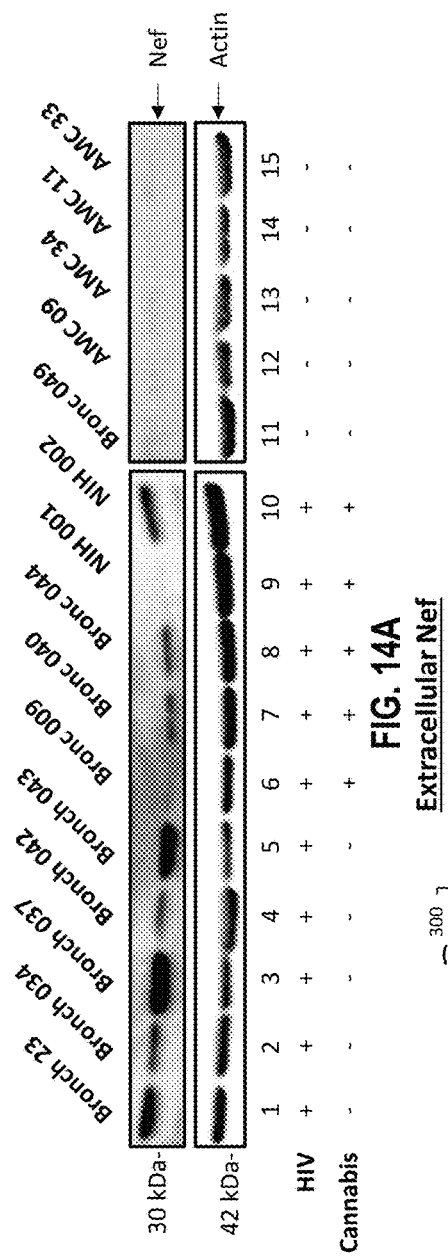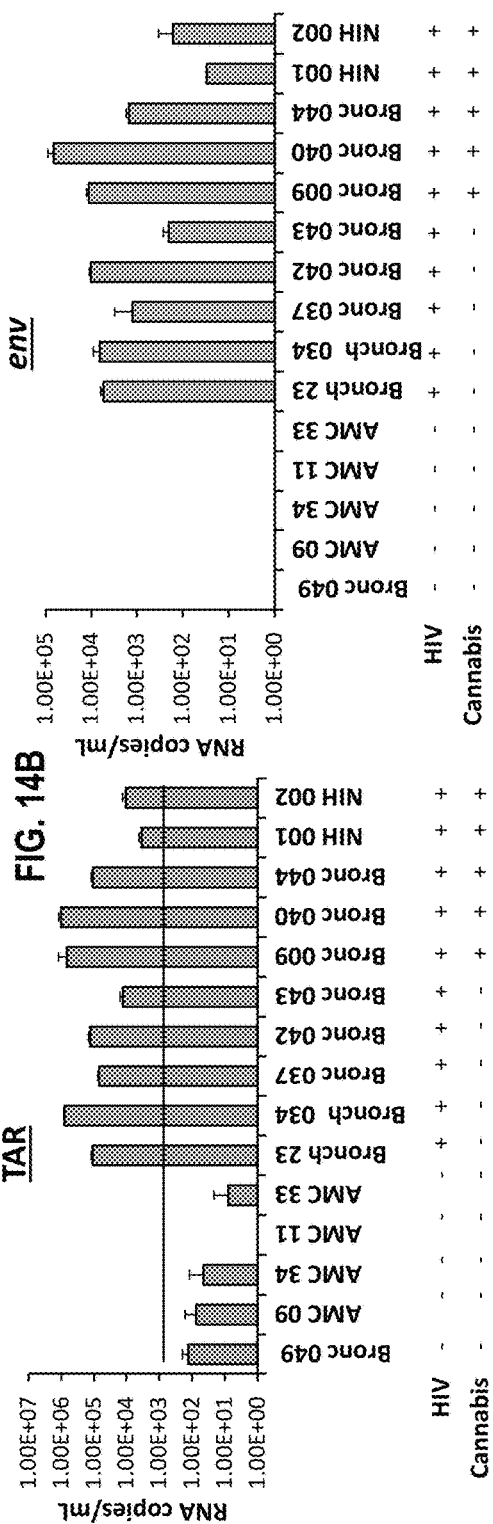
FIG. 14A
FIG. 14B
FIG. 14C
FIG. 14D

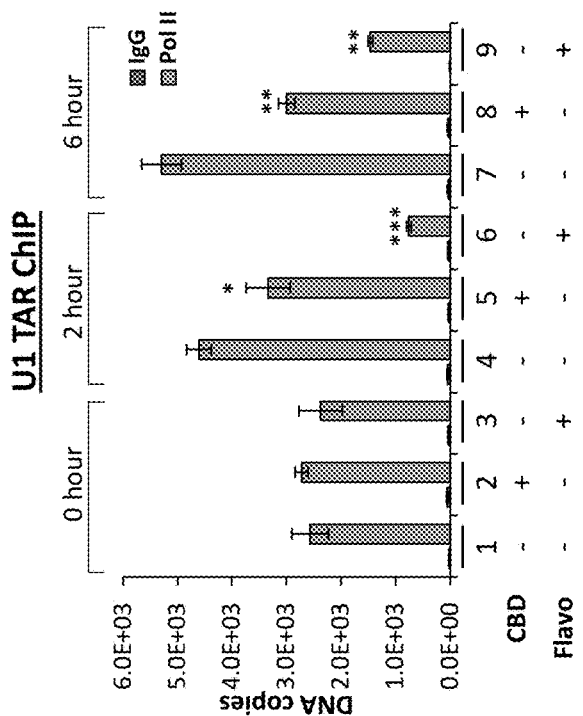
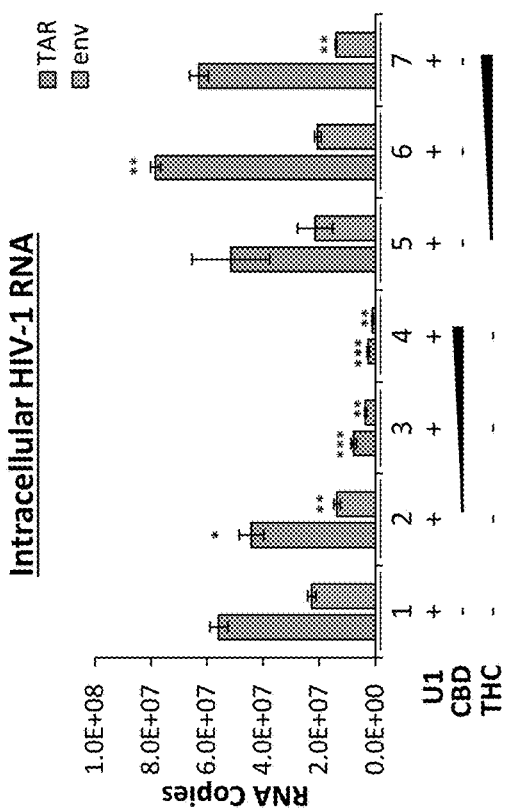
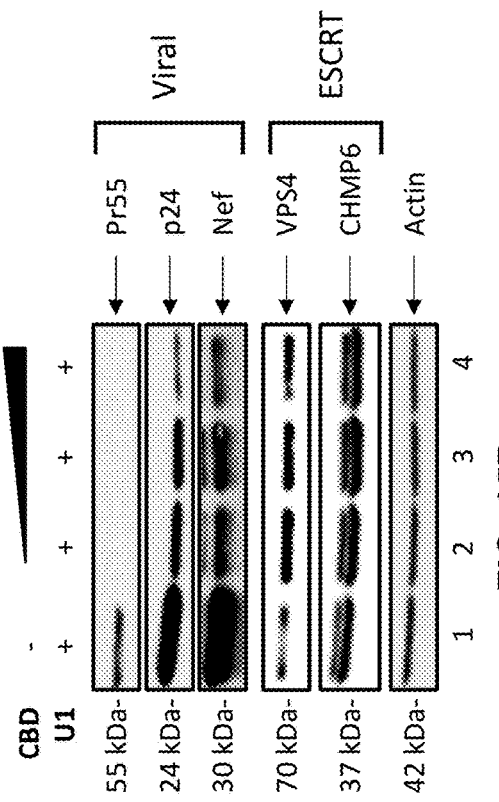
FIG. 15A
FIG. 15B
FIG. 15C

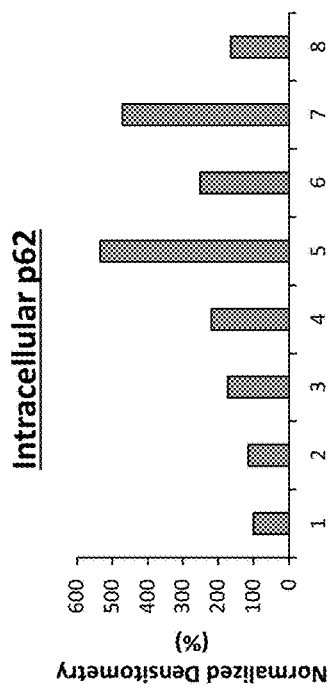
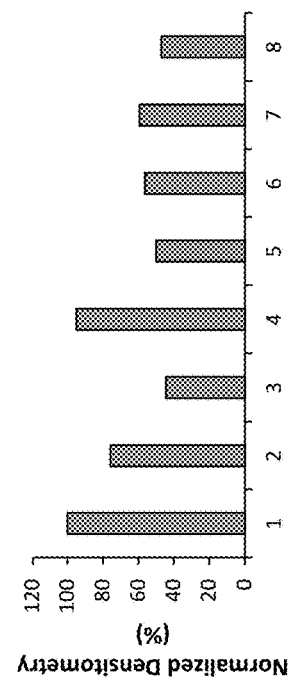
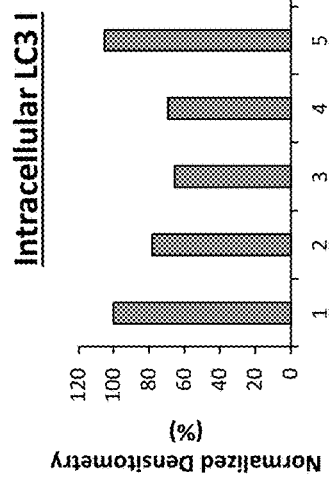
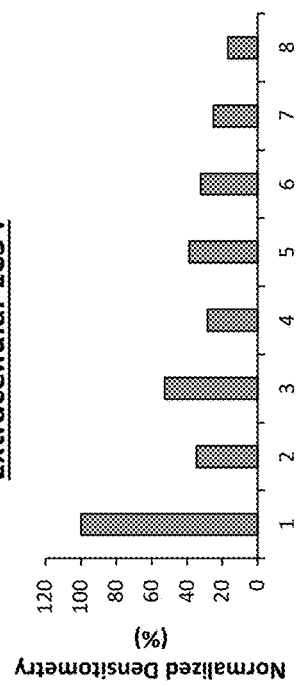
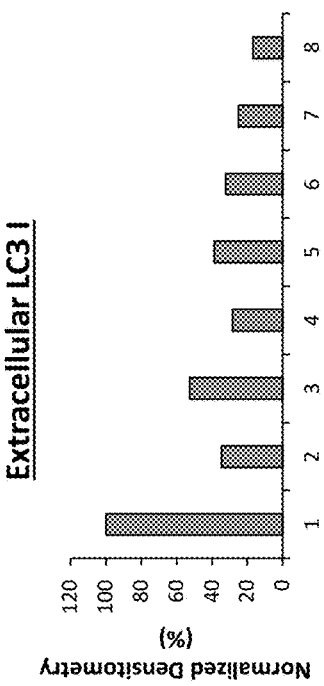

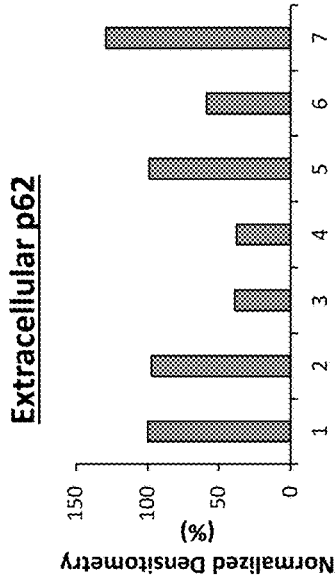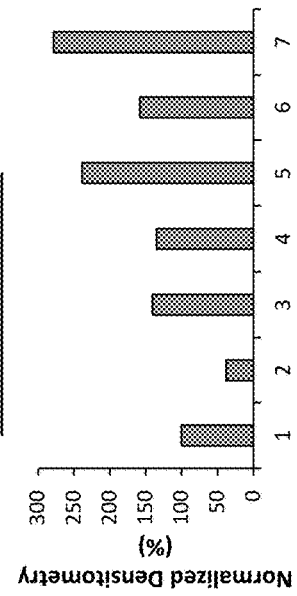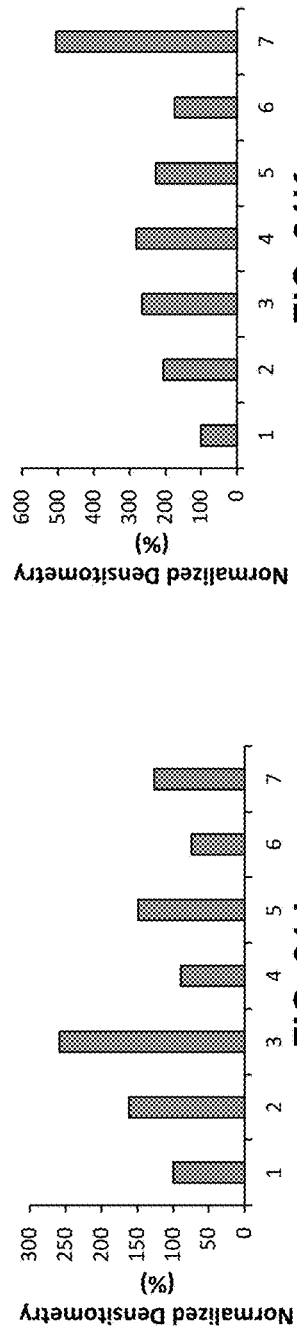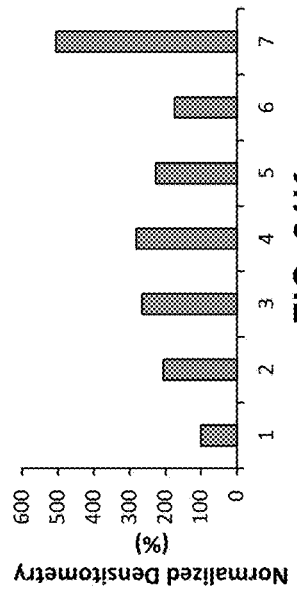

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tgggataagg gtctgaaacg                                             20

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 2
caacagacgg gcacacacta c                                              21

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
ggtctctctg gttagaccag atctg                                          25

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
caacagacgg gcacacacta c                                              21

<210> SEQ ID NO 5
<211> LENGTH: 30
<212> TYPE: DNA
<213> ORGANISM: Artificial Sequence
<220> FEATURE:
<223> OTHER INFORMATION: Synthetic probe

<400> SEQUENCE: 5
agcctcaata aagcttgcct tgagtgcttc                                     30
```

COMPOSITIONS AND METHODS FOR MODULATION OF EXTRACELLULAR VESICLE RELEASE AND TREATMENT OF NEUROLOGICAL DISORDERS

CROSS-REFERENCE TO RELATED APPLICATIONS

This application is a continuation-in-part of International Application No. PCT/US2019/056453 filed on Oct. 16, 2019, which claims priority to U.S. Provisional Application No. 62/746,247 filed on Oct. 16, 2018; each of which is herein incorporated by reference in its entirety.

STATEMENT REGARDING FEDERALLY SPONSORED RESEARCH OR DEVELOPMENT

This invention was made with government support under grant number AI127351, AI043894, NS099029 awarded by the National Institutes of Health. The government has certain rights in the invention.

REFERENCE TO SEQUENCE LISTING

The Sequence Listing concurrently submitted herewith as a text file named "381789_7002US1_Sequence_Listing.txt," created on Apr. 28, 2021 and having a size of 1,421 bytes is herein incorporated by reference pursuant to 37 C.F.R. § 1.52(e)(5).

BACKGROUND OF THE INVENTION

Extracellular vesicles (EVs) are small, extracellular, membrane-bound vesicles of from approximately 30 to above 250 nm in diameter. EVs have emerged as a means of intercellular communication and can contribute to the pathogenesis of several diseases including viral infection, cancer and neurodegenerative diseases through the selective incorporation of cargo. Following extracellular release, EVs can bind to recipient cells and deliver packaged proteins, mRNAs, and miRNAs that are then capable of inducing change in the recipient cell, thereby promoting disease phenotypes in affected individuals.

Human immunodeficiency virus ("HIV") infection causes a broad range of pathologic processes. HIV-associated neurocognitive disorder is one of the late-stage complications of HIV infection, which contributes to a spectrum of disorders in cognitive function that ranges from asymptomatic disease to severe dementia (HIV-associated dementia, or HAD). HAD is characterized by frank memory loss, social withdrawal, alterations in personality, and the inability to perform normal daily living activities. Neurodegenerative diseases are characterized by abnormal protein turnover. For example, Alzheimer's disease is associated with aggregation of the microtubule-associated cytosolic protein tau in the extracellular space. Astrocytes exposed to amyloid peptide actively secrete EVs that contain prostate apoptosis response 4 (PAR-4) and ceramide, which in turn are taken up by neighboring astrocytes and cause apoptosis in astrocytes or neighbor cells.

Given the role of EVs in the neurological pathology, there is a genuine interest in suppressing the EV release induced by pathogens (e.g., HIV) to control pathology in the central nervous system. Several compounds have had success in in vitro studies in the reduction of EV release, however, they are poor therapeutic candidates due to their lack of specificity, low solubility, and blood brain barrier impermeability.

As a result, there is a need for an EV release modulator that could overcome these shortcomings to provide a protective effect.

SUMMARY OF THE INVENTION

This disclosure relates to pharmaceutical compositions for modulating release of extracellular vesicles from a cell infected by a virus. In at least one embodiment, the pharmaceutical composition may include one or more cannabinoid products. In one or more embodiments, the pharmaceutical composition may include azidothymidine, an interferon ("IFN"), a tetracycline, or a combination thereof. In various embodiments, the cannabinoid product can include, but is not limited to, one or more of tetrahydrocannabinol ("THC"), cannabidiol ("CBD"), olivetol, cannabinol ("CBN"), cannabigerol ("CBG"), cannabichromene ("CBC"), cannabicyclol ("CBCL"), nabilone, tetrahydrocannabinolic acid ("THCA"), cannabichromenic acid ("CBCA"), cannabicyclolic acid ("CBCLA"), cannabigerolic acid ("CBGA"), cannabidiolic acid ("CBDA"), cannabinolic acid ("CBNA"), tetrahydrocannabivarin ("THCV"), cannabivarin ("CBV"), cannabidivarin ("CBDV"), cannabigerovarin ("CBGV"), cannabichromevarin ("CBCV"), cannabicyclovarin ("CBCLV"), cannabicyclovarinic acid ("CBCLVA"), cannabigerovarinic acid ("CBGVA"), tetrahydrocannabivarinic acid ("THCVA"), cannabichrome varinic acid ("CBCVA"), and cannabidivarinic acid ("CBDVA").

In at least one aspect, the present disclosure relates to methods of treating a viral disease in a subject including, but not limited to, administering to the subject a therapeutically effective amount of the pharmaceutical composition. In one or more embodiments, the viral disease can include human immunodeficiency virus ("HIV")-associated neurocognitive disorder ("HAND"). In one or more embodiments, the viral disease can include HIV-associated dementia ("HAD"). In various embodiments, the viral disease can include a neurodegenerative disease.

In at least one aspect, the present disclosure relates to methods of reducing damage to neurons from the central neural system ("CNS") or neuroinflammation in a subject. In various aspects, the present disclosure relates to methods of inhibiting transcription of a viral RNA in a cell including contacting the cell with the composition. In one or more aspects, the disclosure relates to methods of modulating extracellular release of EVs.

BRIEF DESCRIPTION OF THE DRAWINGS

FIG. 2C shows that extracellular vesicles from the same supernatant were enriched using NT 80/82 and analyzed by Western blot for gp120, Nef, and CD81, with Actin as a control.

FIG. 5C shows that tetracycline class antibiotics altered EV cargo via binding of the VPS4 protein of the endosomal sorting complex required for transport (ESCRT) pathway. U1 whole cell extracts were incubated with either biotin alone, or biotinylated methacycline or doxycycline. Resulting complexes were pulled down using streptavidin-sepharose beads. The samples were eluted with 40× excess free biotin, run on a 4-20% SDS/PAGE gel, and analyzed by Western blot for VPS4, VPS35/EAP45, and CHMP6. Densitometry counts as determined by ImageJ software show amounts of bound VPS4 relative to the U1 whole cell extract control (set to 100%).

FIGS. 9A-9C are graphs and gels showing cannabinoids decrease the amount of viral cargo carried inside EVs released from infected monocytes. U1 cells ($1\times10^6$) were treated with a titration of CBD (1, 5, 10 μM) and THC (1, 5, 10 μg/mL) every day for 5 days. Cellular supernatant was collected, exosomes were enriched with nanoparticles (NT80/82) beads overnight at 4° C., (A) pelleted, run through SDS-PAGE, and western blotted for exosomal (CD81) and HIV viral markers (myr-Nef, Nef, gp160, gp120), as well as actin. B) Following the same experimental design as (A), cellular supernatant was nanotrapped and pelleted. RNA was isolated from the samples, followed by RT-qPCR analysis for HIV-1 viral transcripts, TAR and (C) env. Student's t-test was used for statistical analysis, where *p-value≤0.05; p-value≤0.01, *p-value≤0.001.

FIGS. 10A-10E are graphs showing normalized densitometry analysis of cannabidiol components lowering of EV-associated viral cargo from HIV-1 infected monocytes. (A) CD81, (B) Myr-Nef, (C) Nef, (D) gp160, and (E) gp120 densitometry counts were performed on the Western blot data from FIG. 2A, all of which were normalized to Actin levels.

FIGS. 11A-11B are graphs showing CBD lowers viral RNAs in EVs released from HIV-1 infected primary macrophages. Primary PBMCs were purchased (Precision For Medicine, Frederick, Md.) and cultured in vitro first with PMA/GM-CSF for 3 days to obtain macrophages, and were then infected with HIV-1 89.6 strain (MOI.1.0) for 12 days. The macrophages were treated with PMA and GM-CSF during the infection period (added every 3 days into the fresh media). On day 12, all cells were treated with cART (4 antivirals) and kept in culture for another 3 days. On day 15, media was removed and CBD was added for 5 days (1, 5, 10 µM; at 0 and 48 hours). Supernatants were then isolated and exosomes were enriched using NT80/82 beads overnight at 4° C. The NT80/82 beads were then pelleted, RNA was isolated, followed by RT-qPCR analysis for A) TAR and (B) env viral RNA transcripts. These are an average of 3 replicates. Student's t-test was used for statistical analysis, where *p-value≤0.05; p-value≤0.01, *p-value≤0.001.

Figures 12A, 12B:
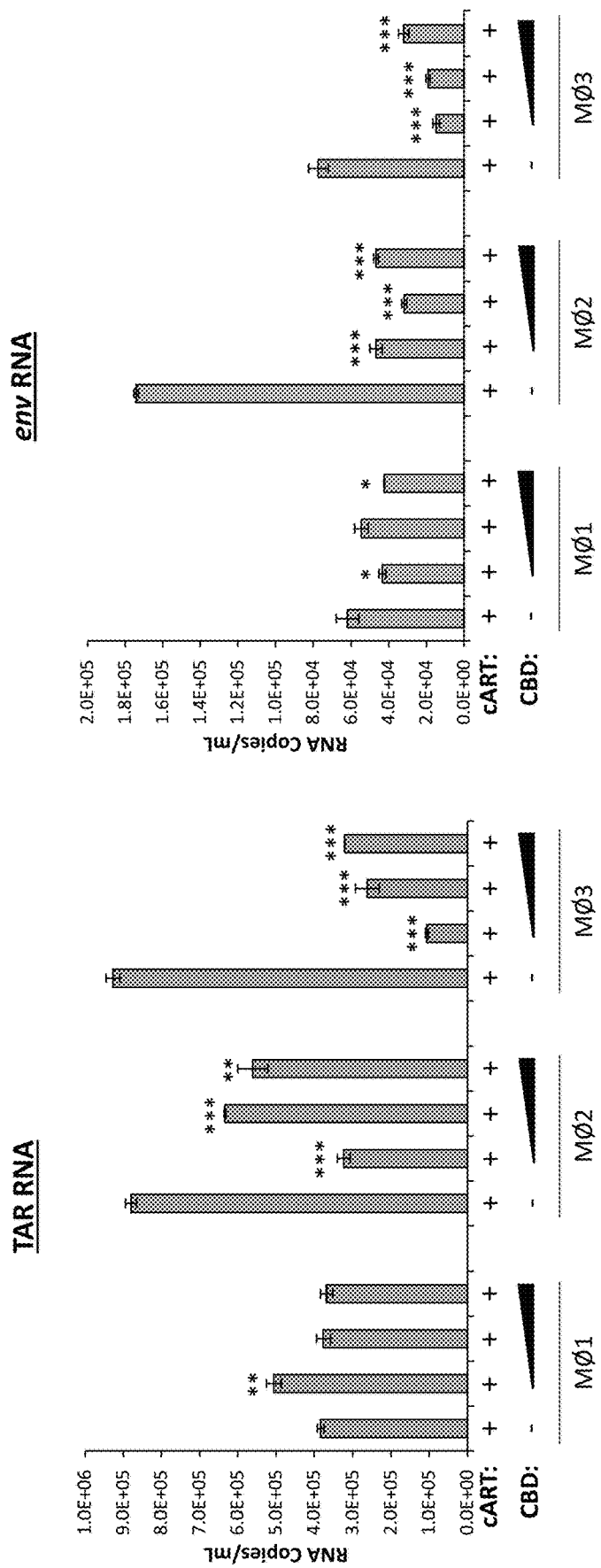

FIGS. 12A-12B are graphs showing CBD lowers EV-associated viral RNAs from HIV-1 infected primary macrophages treated with cART. HIV-1 infected primary macrophages ($1\times10^6$ cells) were treated with cART (10 µM; Emtricitabine, Tenofovir, Darunavir and 5 µM Ritonavir) twice for 5 days. EVs from the supernatant were enriched using NT80/82 beads and RNA was isolated, followed by RT-qPCR analysis for (A) TAR and (B) env RNA transcripts in three biological replicates. Student's t-test was used for statistical analysis, where *p-value≤0.05; p-value≤0.01, *p-value≤0.001.

FIGS. 13A-13B are graphs showing CBD lowers EV-associated viral RNAs from HIV-1 infected primary T-cells. PBMCs were purchased and cultured in vitro first to obtain macrophages. The suspension cells were then taken and treated with PHA/IL-2 for 3 days to obtain T-cells, and were then infected with HIV-1 89.6 strain (MOI.1.0) for 6 days. The 6th-day cultures were then treated with cART for an additional 3 days to stop the spreading of the virus. On day 9, media was removed and CBD (1, 5, 10 µM) was added for another 3 days. EVs from the supernatant were enriched using NT80/82 beads, and RNA was isolated from the EVs. RT-qPCR analysis was performed for presence of (A) TAR and (B) env viral RNA transcripts in three biological replicates. Student's t-test was used for statistical analysis, where *p-value≤0.05; p-value≤0.01, *p-value≤0.001.

FIGS. 14A-14D are graphs and gels showing *Cannabis* lowers EV-associated viral proteins from HIV-1 infected individuals. A) Plasma from three groups of patients (HIV-1 infected, HIV-1 infected taking *Cannabis*, uninfected) were extracted. The EVs from the plasma samples were enriched using NT80/82 particles, and were run through SDS-PAGE, followed by Western blot analysis for Nef and Actin. B) Densitometry counts of Nef protein levels from panel A were calculated, normalized to Actin, and plotted. C) Following the same experimental design as panel A, RNA was isolated from EVs enriched by NT80/82 particles of the patient biofluids, followed by RT-qPCR analysis for levels of TAR and (D) env RNA transcripts. Student's t-test was used for statistical analysis, where *p-value≤0.05; p-value≤0.01, *p-value≤0.001.

FIGS. 15A-15C are graphs and gels showing cannabidiols lower intracellular viral transcription and downstream viral products. U1 cells ($1\times10^6$) were treated with a titration of CBD (1, 5, 10 µM) and THC (1, 5, 10 µg/mL) every day for 5 days. A) Intracellular RNA was isolated and analyzed through RT-qPCR for HIV-1 viral transcripts TAR and env. Each bar represents an average of three independent replicates. B) U1 cells ($2\times10^6$) were treated with a titration of CBD (1, 5, 10 µM) every day for 5 days. Cells pellets were lysed, run through SDS-PAGE, and western blotted for (p-)/NF-κB, autophagosomal markers (p63, LC3), EV biogenesis marker VPS4, viral markers (gp120, Nef, p24), and Actin. C) U1 cells ($5\times10^6$) were treated±CBD (10 µM) and Flavopiridol hydrochloride (50 nM; indicated as Flavo) incubated for the following time points: 0 minutes, 2 hours and 6 hours. Cells were cross-linked with 1% formaldehyde solution and ChIP-ed for IgG and Pol II. ChIP DNA samples were analyzed via qPCR for TAR and env. Student's t-test was used for statistical analysis, where *p-value≤0.05; p-value≤0.01, *p-value≤0.001.

FIGS. 16A-16E are graphs showing normalized densitometry analysis of CBD lowering intracellular viral RNAs in HIV-1 infected monocytes. (A) Nef, (B) Pr55, (C) p24, (D) VPS4, and (E) CHMP6 densitometry counts were performed on the Western blot data from FIG. 4B, all of which were normalized to Actin levels.

Figure 17:
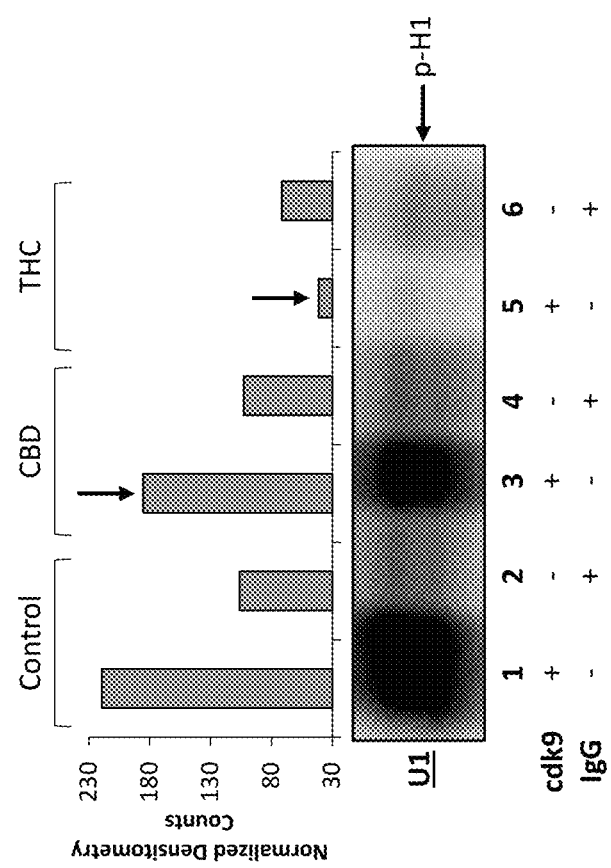

FIG. 17 is a graph with gel showing cannabinoids lower phosphorylation of Histone H1. U1 cells ($5\times10^6$) were treated with CBD (1 µM) and THC (1 µg/mL) every day for 5 days. Cells were then lysed, centrifuged and the supernatants (~150 ug) incubated with anti-cdk9 and IgG antibodies as described in the Kinase Assay section (Materials and Methods), ran on a 4-20% gel and dried, followed by imaging for phosphorylated Histone 1 (p-H1). p-H1 Densitometry counts were calculated on the kinase blot and normalized to background gel pieces.

Figures 18A, 18B:
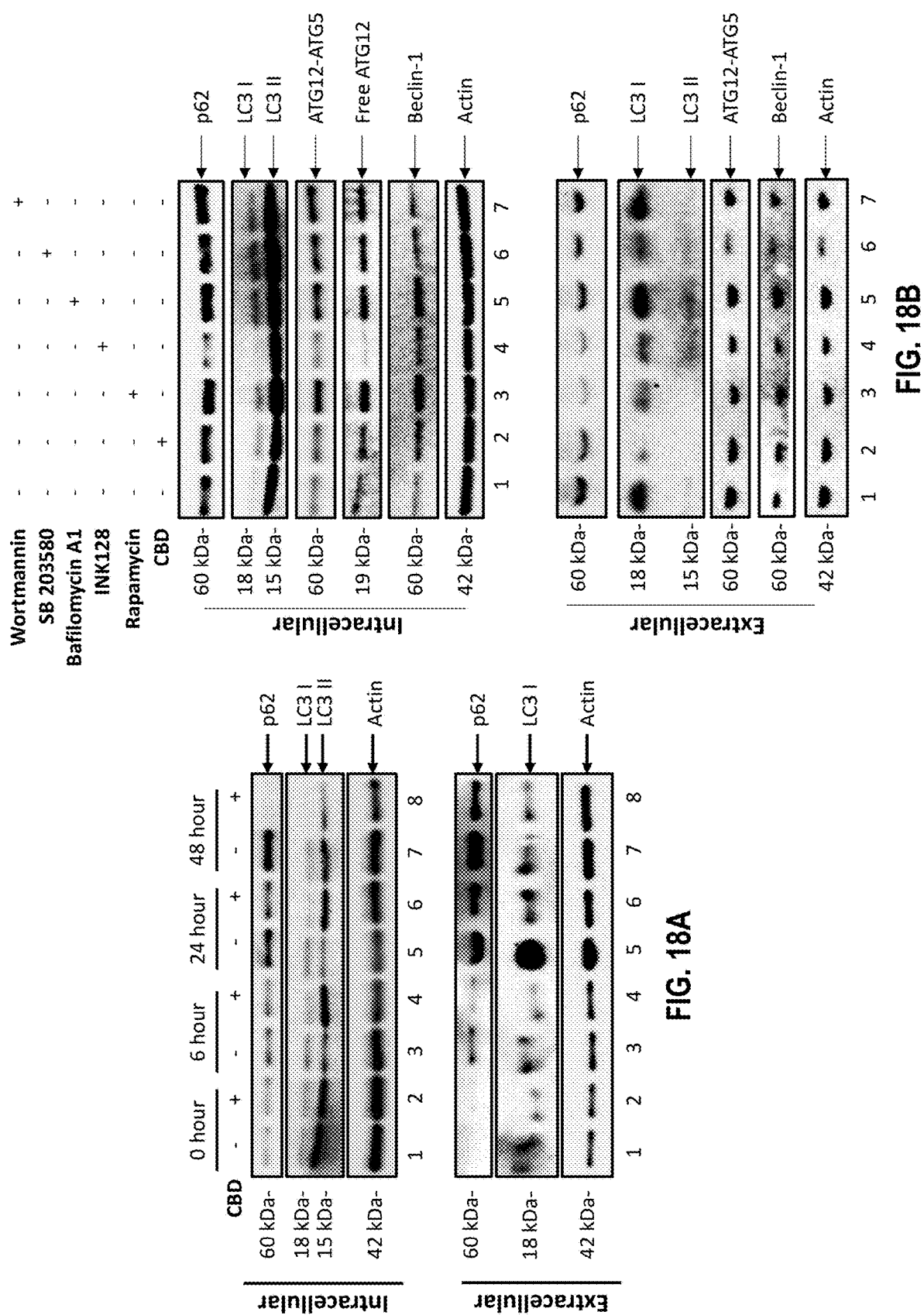

FIGS. 18A-18B are gels showing CBD promotes autophagy turnover, resulting in a decrease in extracellular autophagosomal secretion. A) U1 cells ($1\times10^6$) were treated±CBD (10 µM) for the following incubation periods: 0, 6, 24, and 48 hours. Cells were pelleted and lysed, exosomes from supernatants were enriched with NT80/82 beads overnight at 4° C. Samples were run through SDS-PAGE and western blotted for autophagy proteins (p62 and LC3), and Actin. B) U1 cells ($1\times10^6$) were treated±10 µM CBD (every day), Rapamycin (50 nM), INK128 (50 nM), Bafilomycin A1 (50 nM), SB 203580 (20 µM), Wortmannin (2 nM) for a 5-day incubation period. Cells were pelleted and lysed, exosomes from supernatants were enriched using NT80/82 beads overnight at 4° C. Samples were run through SDS-PAGE and western blotted for autophagy proteins (p62, LC3, ATG12-ATG5, ATG12, Beclin-1), and Actin.

FIGS. 19A-19E are graphs showing normalized densitometry analysis of CBD treatment of HIV-1 infected monocytes over time and autophagy. Intracellular (A) p62, (B) LC3 I, and (C) LC3 II levels, and extracellular (D) p62, and (E) LC3 I levels were counted on the Western blot data from FIG. 5A through densitometry analysis, followed by normalization to Actin levels.

Figure 20:
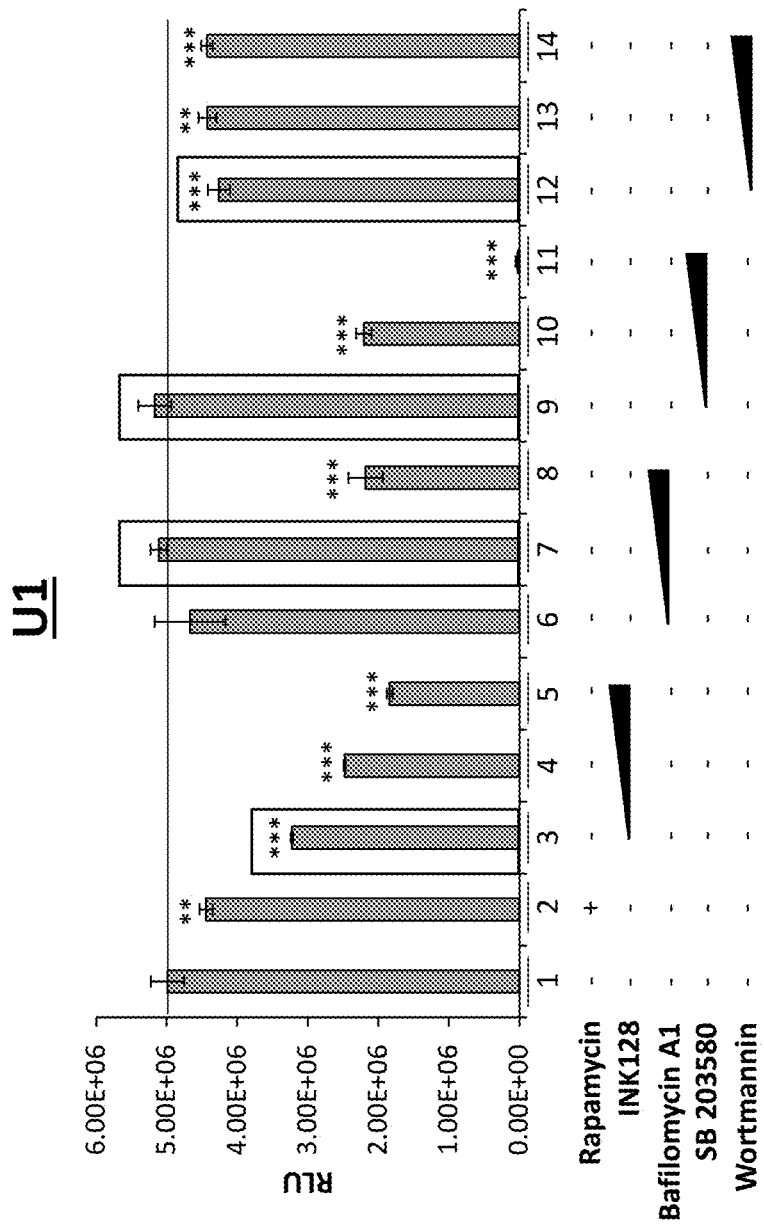
Figure 21B:
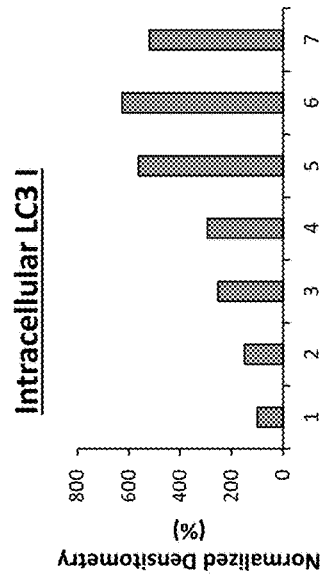
Figure 21A:
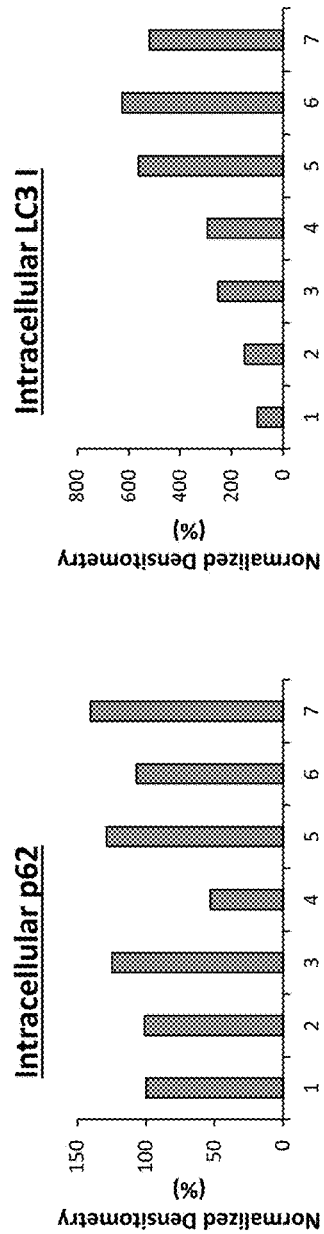
Figure 21D:
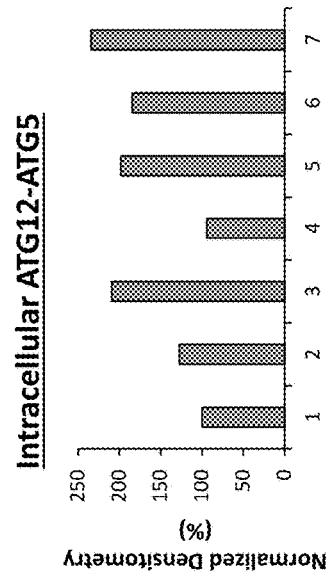
Figure 21C:
Figure 21F:
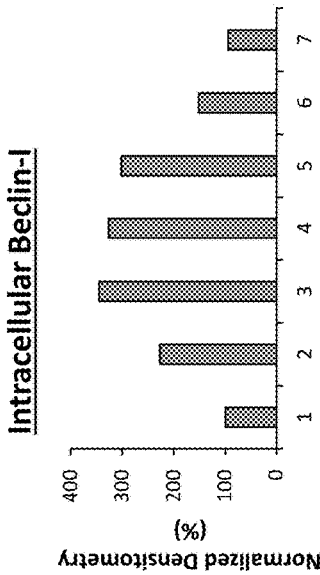
Figure 21E:
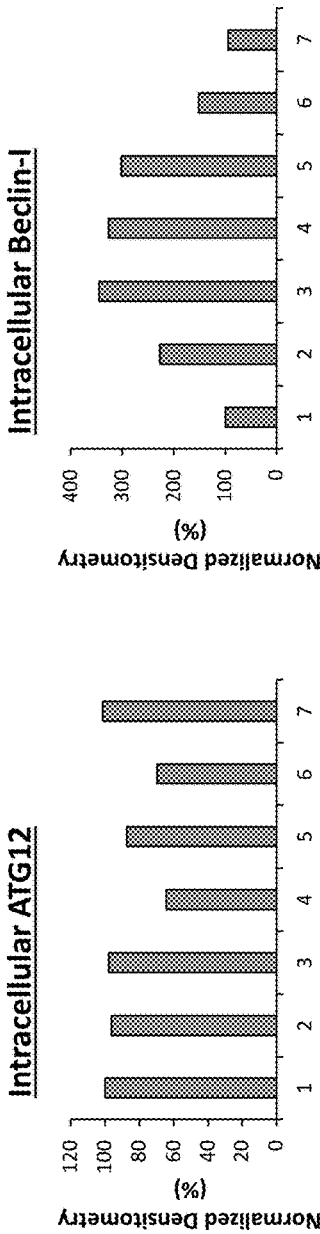

FIG. 20 is a graph showing cell viability analysis of autophagy drugs on HIV-1 infected monocytes and secreted EVs. HIV-1 infected U1 cells ($5\times10^4$ cells) were treated with a titration of the following autophagy drugs for 5 days: Rapamycin (50 nM), INK128 (50, 100, and 200 nM), Bafilomycin A1 (10, 50, and 100 nM), SB 203580 (20, 50, and 100 µM), and Wortmannin (2, 10, and 100 nM). Cells were developed and assessed for cell viability using CellTiter Glo reagent. Student's t-test was used for statistical analysis, where *p-value≤0.05; p-value≤0.01, *p-value≤0.001.

FIGS. 21A-21K are graphs showing normalized densitometry analysis of CBD and autophagy drug treatment on HIV-1 infected monocytes. Intracellular (A) p62, (B) LC3 I, (C) LC3 II, (D) ATG12-ATG5 complex, (E) ATG12, and (F) Beclin-1, and extracellular (G) p62, (H) LC3 I, (I) LC3 II, (J) ATG12-ATG5 complex, and (K) Beclin-1 densitometry counts were calculated from the Western blot data in FIG. 5B, normalized to respective intracellular and extracellular Actin levels, and plotted.

FIGS. 22A-22D are graphs, gels, schematics, and images showing cannabidiol lowers viral transcripts in 3D neurospheres. A) Differential workflow of 3D neurospheres. B) Phase contrast microscopic images of three 3D neurospheres taken where scale bar=100 um. D) 3D neurospheres were treated±89.6 viral strain±cART (10 µM; Tenofovir, Emtricitabine, Lamuvidine, and Indinavir)±CBD titration (5 and 10 µM) and incubated for 7 days. RNA was isolated from the 3D neurospheres and supernatants, followed by RT-qPCR analysis for viral RNA transcripts TAR, TAR-gag, env. Student's t-test was used for statistical analysis, where *p-value≤0.05; p-value≤0.01, *p-value≤0.001.

Figure 23A:
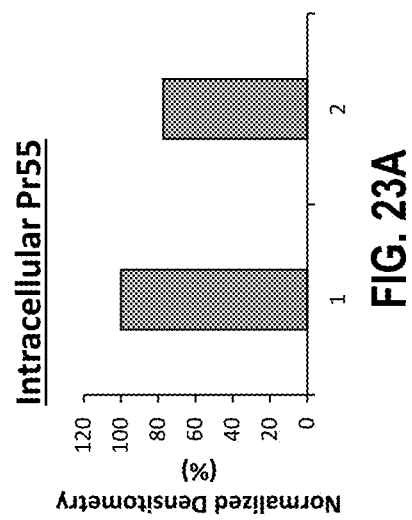
Figure 23B:
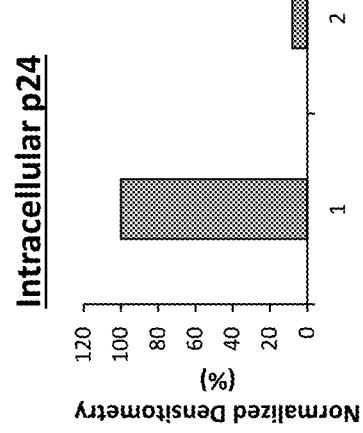
Figure 23C:
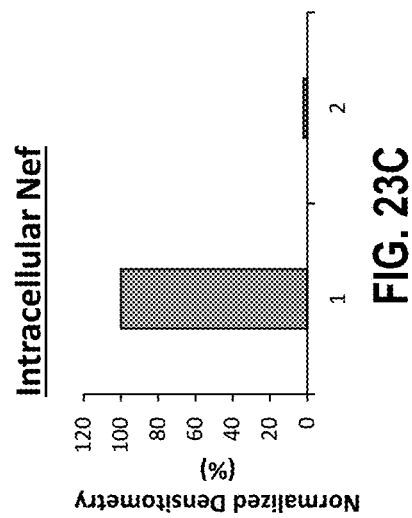
Figure 24A:
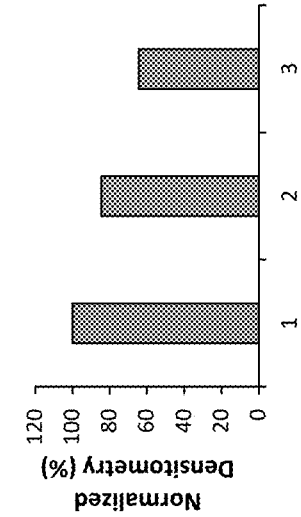
Figure 24B:
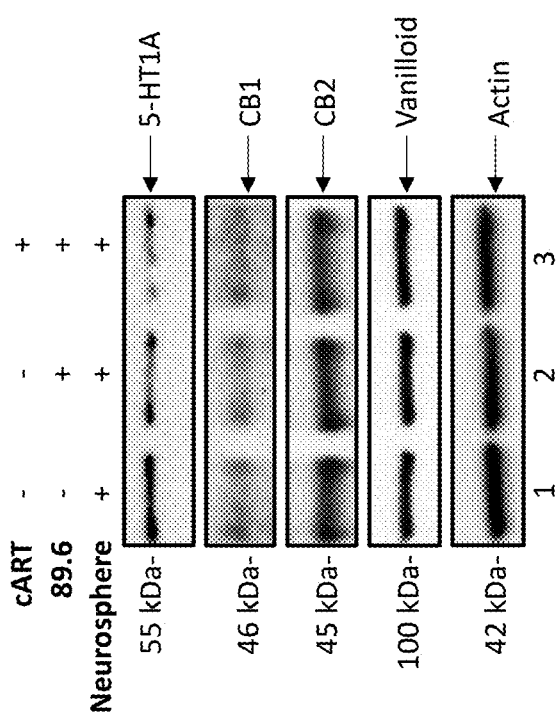
Figure 24E:
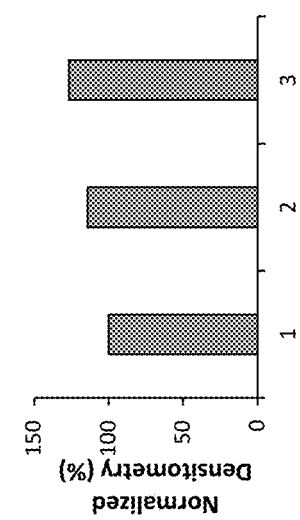
Figure 24D:
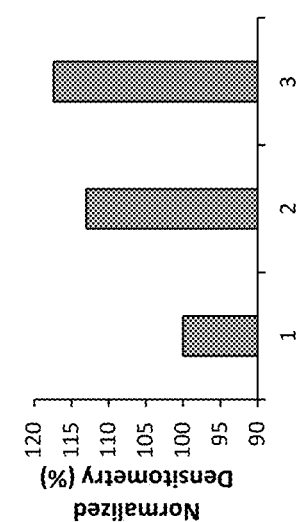
Figure 24C:
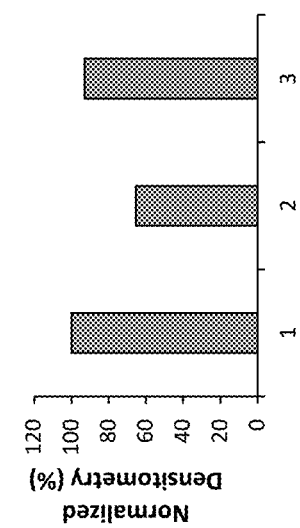

FIGS. 23A-23C are graphs showing normalized densitometry analysis of cART on HIV-1 infected 3D neurospheres. Intracellular (A) Pr55, (B) p24, and (C) Nef densitometry counts were analyzed from the Western blot data of FIG. 6C, followed by normalization to Actin.

FIGS. 24A-24E are graphs and gels showing expression of glial receptors in 3D neurospheres. A) 3D neurospheres were treated±89.6 HIV strain±cART cocktail (10 µM; Tenofovir, Emtricitabine, Lamuvidine, and Indinavir) for a period of 7 days. Neurospheres were harvested, pelleted, and lysed, followed by SDS-PAGE and western blot analysis for neuronal receptor (Vanilloid), cannabinoid receptors (CB1 and CB2), serotonin receptor (5-HT1A), and Actin. Intracellular (B) 5-HT1A, (C) CB1, (D) CB2, and (E) Vanilloid densitometry counts were analyzed from panel A, all of which were normalized to Actin.

Figure 25A:
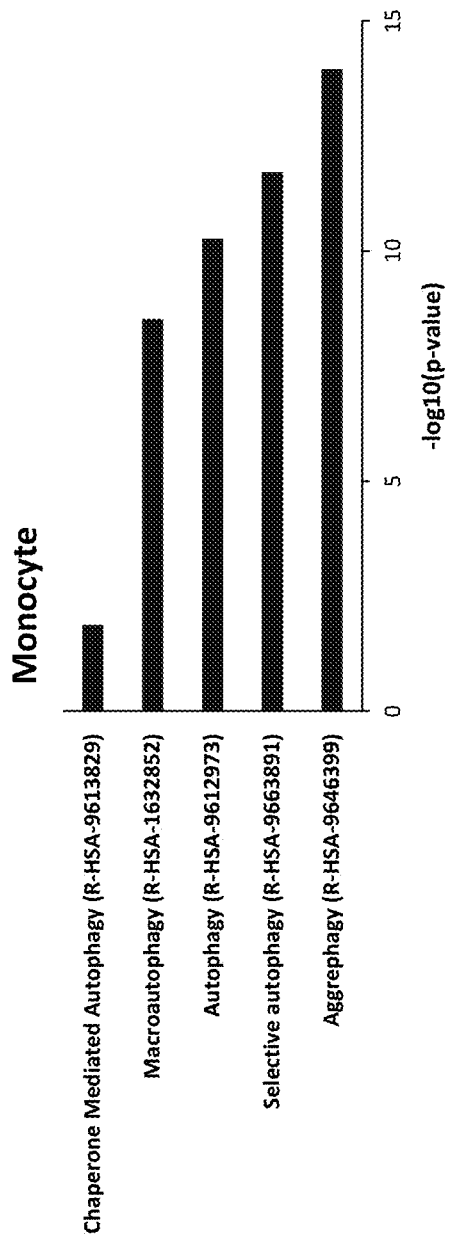
Figure 25B:
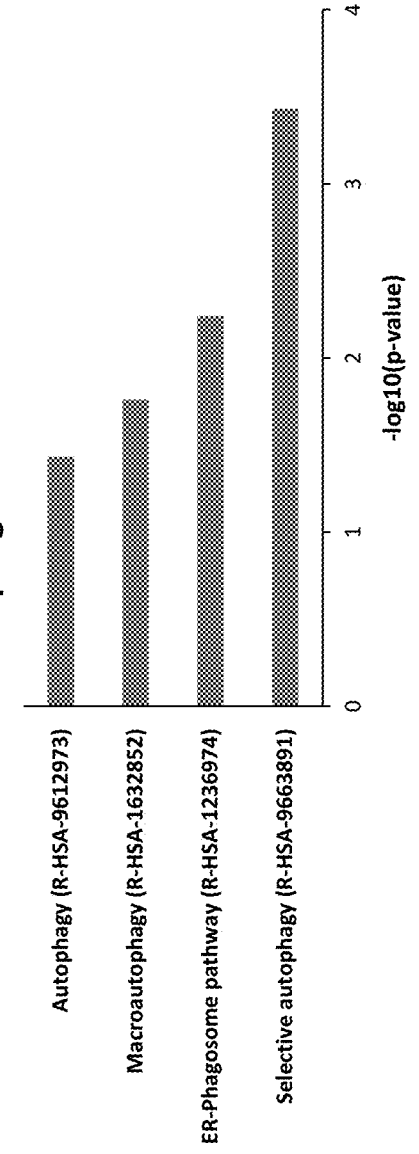

FIGS. 25A-25B are graphs showing mass spectrometry analysis of biotinylated CBD pull down from HIV-1 infected lysates. U1 and U1 MDM cells were cultured and lysed. D-Biotin or Biotinylated CBD pull-down from the lysates was performed using Streptavidin-Sepharose beads, which were washed with $TNE_{300}$ (high salt)+0.1% NP40 buffers. The complexes were analyzed by mass spectrometry. Reactome enrichment analysis was used to assess the CBD pull-down of (A) HIV-1 infected MDM and (B) HIV-1 infected monocytes (U1) proteins for involvement of the autophagy pathway.

Figure 26:
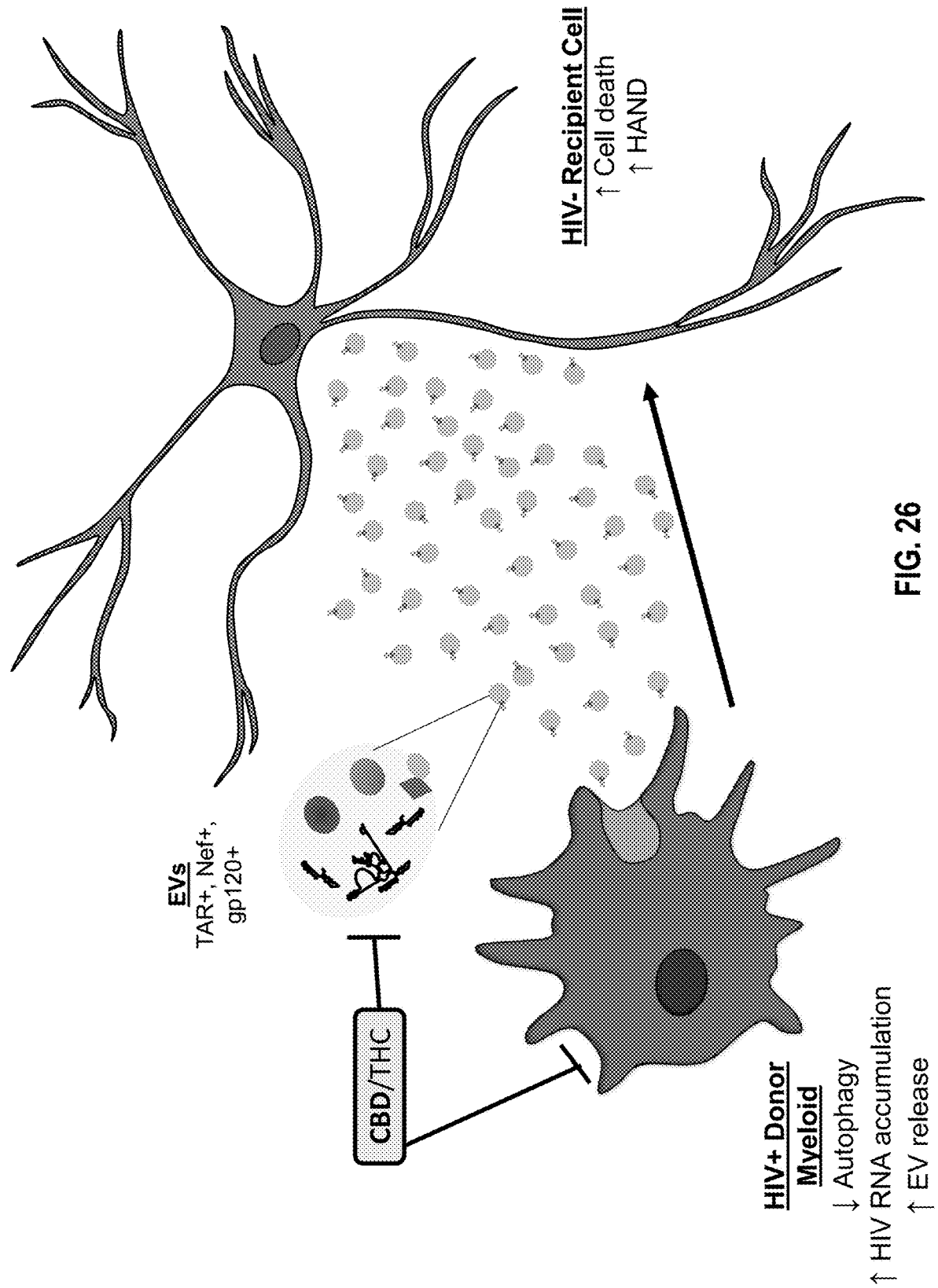

FIG. 26 is a schematic summary of effects of cannabinoids on HIV-1 infected myeloid cells and their EVs. HIV-1 infected myeloid cells, even in the presence of cART, can transcribe viral RNAs that can be made into proteins. HIV proteins can alter the autophagy pathway, resulting in the accumulation of viral products in the cytosol. This can induce increased secretion of EVs carrying viral RNAs and proteins, which can potentially contribute to the neuroinflammation seen in HAND and neuronal cell death. Cannabinoids, specifically CBD and THC, can inhibit the abundance of EVs secreted from HIV-1 infected myeloid cells, as well as the viral RNA and protein cargo incorporated inside the EVs potentially through inhibition of intracellular transcription processes and restoration of the autophagy pathway. This can potentially contribute to decreased EV-mediated inflammation and cellular death.

DETAILED DESCRIPTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated, that all numerical designations are preceded by the term "about." It also is to be understood, although not always explicitly stated, that the reagents described herein are merely exemplary and that equivalents of such are known in the art.

It must be noted that as used herein and in the appended claims, the singular forms "a," "an," and "the" include plural references unless the context clearly dictates otherwise. Thus, for example, reference to "a cell" includes a plurality of cells.

The following definitions assist in defining the meets and bounds of the inventions as described herein. Unless specifically noted, the embodiments describing "extracellular vesicles" shall include "exosomes," "microvesicles," alone or in combination. In some aspects, only one or more of the vesicles are intended.

The term "about" when used before a numerical designation, e.g., temperature, time, amount, concentration, and such other designations, including a range, indicates approximations which may vary by (+) or (−) 10%, 5% or 1%.

The terms "administering" or "administration" are included in reference to delivering an agent or a composition to a subject to perform the intended function. Administration can be carried out by any suitable route, including orally, intranasally, parenterally (intravenously, intramuscularly, intraperitoneally, or subcutaneously), intrathecally, intracranially, or topically. Additional routes of administration include intraorbital, infusion, intra-arterial, intracapsular, intracardiac, intradermal, intrapulmonary, intraspinal, intranasal, intrasternal, intrauterine, intravenous, subarachnoid, subcapsular, subcutaneous, transmucosal, or transtracheal. Administration includes self-administration and the administration by another.

The terms "including", "includes," "comprising," or "comprises" are intended to mean that the compositions, media, and methods include the recited elements, but not excluding others. "Consisting essentially of," when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The terms "patient," "subject," and "mammalian subject" are used interchangeably herein and include any mammal in need of the treatment or prophylactic methods described herein (e.g., methods for the treatment of inflammation). Such mammals include humans (e.g., fetal humans, human infants, human teens, human adults, etc.). Other mammals in need of such treatment or prophylaxis can include non-human mammals such as dogs, cats, or other domesticated animals, horses, livestock, laboratory animals (e.g., lagomorphs, non-human primates, etc.), and the like. The subject may be male or female. In certain embodiments the subject is at risk, but asymptomatic for diseases or conditions related to inflammation or an inflammatory response. In certain embodiments the subject is at risk with virus-associated neurological disorder.

As used herein, the term "cytokine" encompasses low molecular weight proteins secreted by various cells in the immune system that act as signaling molecules for regulating a broad range of biological processes within the body at the molecular and cellular levels. "Cytokines" include individual immunomodulating proteins that fall within the class of lymphokines, interleukins, or chemokines. Interferon is one type of cytokines.

Non-limiting examples of cytokines are disclosed herein. For example, IL-1A and IL-1B are two distinct members of the human interleukin-1 (IL-1) family. Mature IL-1A is a 18 kDa protein, also known as fibroblast-activating factor (FAF), lymphocyte-activating factor (LAF), B-cell-activating factor (BAF), leukocyte endogenous mediator (LEM), etc. IL-4 is a cytokine that induces T helper-2 (Th2) cell differentiation, and is closely related to and has similar functions to IL-13. IL-5 is produced by Th2 cells and mast cells. It acts to stimulate B-cell growth and increase immunoglobulin secretion. It is also involved in eosinophil activation. IL-6 is an interleukin that can act as either a pro-inflammatory or anti-inflammatory cytokine. It is secreted by T-cells and macrophages to stimulate immune response to trauma or other tissue damage leading to inflammation. IL-6 is also produced from muscle in response to muscle contraction. IL-8 is a chemokine produced by macrophages and other cell types, such as epithelial cells and endothelial cells, and acts as an important mediator of the immune reaction in the innate immune system response. IL-12 is involved in the differentiation of naïve T-cells to T helper (Th1 or Th2) cells. As a heterodimeric cytokine, IL-12 is formed after two subunits encoded by two separate genes, IL-12A (p35) and IL-12B (p40), dimerize following protein synthesis. IL-12p70 indicates this heterodimeric composition. IL-13, a cytokine secreted by many cell types, especially Th2 cells, is an important mediator of allergic inflammation and disease. IL-17 is a cytokine produced by T helper cells and is induced by IL-23, resulting in destructive tissue damage in delayed-type reactions. IL-17 functions as a pro-inflammatory cytokine that responds to the invasion of the immune system by extracellular pathogens and induces destruction of the pathogen's cellular matrix. IP-10, or Interferon gamma-induced protein 10, is also known as C-X-C motif chemokine 10 (CXCL10) or small-inducible cytokine B10. As a small cytokine belonging to the CXC chemokine family, IP-10 is secreted by several cell types (including monocytes, endothelial cells and fibroblasts) in response to IFN-γ. Macrophage Inflammatory Proteins (MIP) belong to the family of chemokines. There are two major forms of human MIP, MIP-1a and MIP-10, which are also known as chemokine (C—C motif) ligand 3 (CCL3) and CCL4, respectively. Both are produced by macrophages following stimulation with bacterial endotoxins. Granulocyte colony-stimulating factor (G-CSF or GCSF), also known as colony-stimulating factor 3 (CSF 3), is a colony-stimulating factor hormone. G-CSF is a glycoprotein, growth factor, and cytokine produced by a number of different tissues to stimulate the bone marrow to produce granulocytes and stem cells. G-CSF also stimulates the survival, proliferation, differentiation, and function of neutrophil precursors and mature neutrophils. Epidermal growth factor or EGF is a growth factor that plays an important role in the regulation of cell growth, proliferation, and differentiation by binding with high affinity to its receptor EGFR. Vascular endothelial growth factor (VEGF) is a family of growth factors that are important signaling proteins involved in both vasculogenesis (the de novo formation of the embryonic circulatory system) and angiogenesis (the growth of blood vessels from pre-existing vasculature).

As used herein, the term "interferon" or "IFN" refers to a signaling protein that is released by a host cell in response to presence of a pathogen, e.g., virus, bacterium, a parasite, and a tumor cell. In at least one embodiment, IFNs can prevent or suppress viral replication by protecting cells from virus infections. In another embodiment, IFNs may activate immune cells, such as natural killer cells and macrophages. In various embodiments, IFNs may increase host defenses by up-regulating antigen presentation by virtue of increasing the expression of major histocompatibility complex (MHC) antigens. Non-limiting examples of interferon include interferon type I (e.g., IFN-α, IFN-β, IFN-ε, IFN-κ, and IFN-ω), interferon type II (e.g., IFN-γ), and interferon type III (e.g., IFN-λ1, IFN-λ2, and IFN-λ3).

As used herein, the term "interferon-α" or "IFN-α" refers to interferon-α in native-sequence or in variant forms, and from any source, whether natural, synthetic, or recombinant. One illustrative example is human interferon-α (h IFN-α), which is the natural or recombinant IFN-α with the human native sequence (also known as leukocyte interferon, Type I interferon, B-cell interferon, buffy coat interferon, foreign cell induced interferon, lymphoblast interferon, lymphoblastoid interferon, mamalwa interferon, pH2-stable interferon, or RSV-induced factor). In at least one embodiment, IFN-α of this disclosure includes at least 23 different subtypes of IFN-α. In one or more embodiments, the individual proteins may have molecular masses between 16-27 kDa and consist of proteins with lengths of 156-166 and 172 amino acids. In one or more embodiments, IFN-α subtypes may possess a common conserved sequence region between amino acid positions 115-151 while the amino-terminal ends are variable. In various embodiments, IFN-α subtypes may differ in their sequences at only one or two positions. In at least one embodiment, IFN a includes a naturally occurring variant with a protein truncated by 10 amino acids at the carboxy-terminal end. In one or more embodiments, disulfide bonds may be formed between cysteines at positions 1/98 and 29/138. The disulfide bond 29/138 is essential for biological activity while the 1/98 bond can be reduced without affecting biological activity. In at least one embodiment, IFN-α forms can contain a potential glycosylation site. As used herein, recombinant interferon-α (rIFN-α) can refer to any IFN-α or variant produced by means of recombinant DNA technology. In various embodiments, a group of therapeutic compounds of interest for mucosal delivery may be interferon α (IFN-α), such as, for example, human interferon α-2b, (IntronA©, Schering Corporation).

As used herein, the term "azidothymidine" or "AZT" refers to the chemical compound of 3'-azido-2'3'-di deoxythymidine or its derivatives or analogs. In various embodiments, AZT can be an analogue of thymidine, which is one of the four incorporated in the DNA nucleosides. In at least one embodiment, AZT and thymidine may differ by the substitution of the OH group at the 3'-position of the deoxysugar by an azido group. In one or more embodiments, AZT can inhibit replication of HIV virus by inhibiting enzyme reverse transcriptase that HIV uses to make DNA.

As used herein, the term "tetracycline antibiotic" refers to a class of antibiotics that are characterized by four hydrocarbon rings. In various embodiments, tetracycline antibiotics may be used in treatment of infections of the urinary tract, respiratory tract, and the intestines and can also be used in the treatment of *Chlamydia*, especially in patients allergic to β-lactams and macrolides. Non-limiting examples of tetracycline antibiotics include tetracycline, chlortetracycline, oxytetracycline, demeclocycline, lymecycline, meclocycline, methacycline, minocycline, rolitetracycline, and tigecycline.

As used herein, the term "viral disease" refers to a disorder that occurs when a subject is infected with a virus or a viral particle. Non-limiting examples of pathogenic viruses that can cause viral diseases include adenovirus, coxsackievirus, Epstein-Barr virus ("EBV"), hepatitis A virus ("HAV"), hepatitis B virus ("HBV"), hepatitis C virus ("HCV"), herpes simplex virus ("HSV") (e.g., type 1 or type 2), cytomegalovirus ("CMV"), herpesvirus, Kaposi's sarcoma herpes virus, human immunodeficiency virus ("HIV"), human endogenous retroviruses ("HERV"), human T-cell lymphotrophic virus ("HTLV"), human herpes virus-6 ("HHV-6"), varicella zoster virus ("VSV"), influenza virus, measles virus, mumps virus, human papillomavirus, parainfluenza virus, poliovirus, rabies virus, respiratory syncytial virus, rubella virus, varicella-zoster virus, hepatitis virus, and bunyavirus. In at least one embodiment, the virus can cause infection in the CNS, and the virus can include but is not limited to retroviridae (e.g., HIV, HTLV, and HERV), herpesviridae (e.g., VSV, CMV, HHV-6, HSV, and EBV), picornaviridae (e.g., nonpolio enterovirus ("NPEV"), poliovirus ("PV"), and human parchovirus ("HPeV")), flaviviridae (e.g., tick-borne encephalitis virus ("TBEV"), West Nile virus ("WNV"), zika virus ("ZIKV"), and Japanese encephalitis virus ("JEV")), filoviridae (e.g., Ebola virus ("EBOV") and marburg virus ("MARV")), paramyxoviridae (e.g., measles virus (MV) and mumps virus ("MuV")), rhabdoviridae (e.g., rabies virus ("RV")), polyomaviridae (e.g., John Cunningham virus ("JCV")), togaviridae (e.g., chikungunya virus ("CHIKV") and/or Eastern Equine encephalitis virus ("EEV")).

In one or more embodiments, the virus can include, but is not limited to, HIV, HTLV, HSV, EBV, Kaposi's sarcoma herpes virus, CMV, human HPV, hepatitis virus, and/or bunyavirus. The viral diseases can infect the subject with various mechanisms. Non-limiting examples of the viral diseases include influenza, meningitis, Acquired Immune Deficiency Syndrome ("AIDS"), fever, herpes simplex, measles, cancers, gastroenteritis, keratoconjunctivitis, pharyngitis, croup, pharyngoconjunctival fever, and pneumonia. In one embodiment, the viral disease includes a HIV-associated neurocognitive disorder. In another embodiment, the viral disease includes Alzheimer's disease, multiple sclerosis, stroke, or the combination thereof. In another embodiment, the viral disease is an HIV-associated dementia.

The term "HIV-associated neurocognitive disorder" or "HAND" refers to a neurological disorder associated with HIV infection and AIDS. In one embodiment, the HIV-associated neurocognitive disorders are associated with a metabolic encephalopathy induced by HIV infection and fueled by immune activation of macrophages and microglia. These infected cells can secrete neurotoxins of both host and viral origin, which causes disabling cognitive impairment accompanied by motor dysfunction, speech problems and behavioral change. In some embodiments, the HIV-associated neurocognitive disorders are characterized by mental slowness, trouble with memory, poor concentration, and motor symptoms including a loss of fine motor control leading to clumsiness, poor balance and tremors. Behavioral changes associated with HAND may include apathy, lethargy, and diminished emotional responses and spontaneity. In one embodiment, HAND can be identified by the infiltration of monocytes and macrophages into the central nervous system ("CNS"), gliosis, pallor of myelin sheaths, abnormalities of dendritic processes, and neuronal loss. Non-limiting examples of HAND include asymptomatic neurocognitive impairment ("ANI"), minor neurocognitive disorder ("MND"), and HIV-associated dementia ("HAD").

The terms "treatment," "treat," "treating," etc., as used herein include, but are not limited to, alleviating a symptom of a disease or condition (e.g., a disease or condition involving an HIV-associated neurocognitive disorder in a subject in need thereof) and/or reducing, suppressing, inhibiting, lessening, ameliorating, or affecting the progression, severity, and/or scope of the disease or condition. Additional treatments include but are not limited to inhibiting damage to a CNS neuron, treating HIV-associated dementia, treating brain inflammatory disease and/or viral diseases, treating stroke, treating multiple sclerosis (MS), treating Alzheimer's disease, treating inflammation-induced soft tissue damage, treating frailty, treating peripheral arterial disease ("PAD"), or treating brain damage. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented. In one aspect, the term "treatment" excludes prophylaxis. In another aspect, treatment is only prophylaxis.

As used herein, the term "agent" or "factor" refers to a molecule, complex of molecules, cell, organelle, cellular product, or cellular component or fragment that is chemically, physically, and/or biologically active. Non-limiting examples of agents include but are not limited to peptides, polypeptides, proteins, nucleic acids, polynucleotides, DNA, RNA, miRNA, siRNA, mRNA, lipids, small molecules, sugars, pharmaceutical compounds, cells, stem cells, cell-derived vesicles, cytokines, chemokines, steroids, microbes, viruses, vaccines, blood, blood components, allergenics, somatic cells, and tissues. In some aspects, administration or use of an agent or factor results in a desired effect in a target cell, cell product, population, cell-derived vesicle, and/or subject. For example, a neurotrophic factor may produce a neuroprotective effect. An anti-inflammatory agent may produce an anti-inflammatory effect.

The term "substantially" refers to the complete or nearly complete extent or degree of a characteristic and in some aspects, defines the purity of the isolated or purified population of exosomes or microvesicles. For example, a substantially homogenous cell-derived vesicle population may be a cell-derived vesicle population that contains more than 50%, more than 60%, more than 70%, more than 80%, more than 90%, more than 95%, more than 98%, or 100% cell-derived vesicles that include at least one exogenous nucleic acid, protein, or both.

As used herein, the term "pharmaceutically acceptable carrier" refers to any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions including such carriers are formulated by well-known conventional methods. Depending on the intended mode of administration and the intended use, the compositions may be in the form of solid, semi-solid, or liquid dosage forms, such as, for example, powders, granules, crystals, liquids, suspensions, liposomes, pastes, creams, salves, etc., and may be in unit-dosage forms suitable for administration of relatively precise dosages.

A "therapeutically effective amount" refers to an amount sufficient to effect beneficial or desired results. An effective amount can be administered in one or more administrations, applications, or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

As used herein, "neuroinflammatory disease" or "neuroinflammation" is inflammation of the nervous tissue and related diseases or conditions. In one embodiment, neuroinflammation is an immune response that causes damage to the central nervous system. Neuroinflammation can be caused by infection, traumatic brain injury, toxic metabolites, neurodegeneration, and/or autoimmunity. Exemplary neuroinflammatory diseases include but are not limited to acute disseminated encephalomyelitis ("ADEM"), Optic Neuritis ("ON"), Transverse Myelitis, Neuromyelitis Optica ("NMO"), Alzheimer's disease, Parkinson's disease, multiple sclerosis, primary and secondary progressive MS, relapsing remitting MS, brain inflammation, and traumatic brain injury.

As used herein, the term "anti-inflammatory agent" is used to refer to an agent that suppresses an inflammatory response. Non-limiting examples include but are not limited to anti-inflammatory cytokines and chemokines (e.g., TGF-β, IL-2, IL-1Rα, IL-4, IL-6, IL-10, IL-17, IL-11, IL-13, IL-35, IL-37, INF-α), non-steroidal anti-inflammatory drugs ("NSAIDs"), antileukotrienes, and immune selective anti-inflammatory derivatives ("ImSAIDs").

As used herein, the term "neurotrophic factor" is used to refer to an agent that supports the growth, proliferation, survival, and/or differentiation of developing and/or mature neural tissue such as neurons. In some aspects, administration of a neurotrophic factor has neuroprotective effects. Many neurotrophic factors function through tyrosine kinase signaling pathways. Neurotrophic factors include but are not limited to neurotrophins, glial cell-line derived neurotrophic factor family ligands, and neuropoietic cytokines. In some embodiments, the neurotrophic factors of the disclosed compositions and methods include but are not limited to brain derived neurotrophic factor ("BDNF", e.g., NP_001137277), nerve growth factor ("NGF", NP_002497) Neurotrophin-3 ("NTF3", NP_001096124, NP_002518), ciliary neurotrophic factor ("CTNF", NP_000605), glial cell derived neurotrophic factor ("GDNF", e.g., NP_000505), fibroblast growth factors ("FGFs", e.g., FGF1, NP_000791, FGF2 NP_001997), insulin-like growth factors ("IGFs", e.g., IGF1, NP_000609, IGF2, e.g., NP_000603), hepatocyte growth factor ("HGF", e.g., NP_000592), Noggin ("NOG", NP_005441), thyroid hormone triiodothyronine (T3", (2S)-2-amino-3-[4-(4-hydroxy-3-iodo-phenoxy)-3,5-diiodo-phenyl]propanoic acid, molecular formula $C_{15}H_{11}I_3NNaO_4$), and equivalents of each thereof. Preferably, the FGF is FGF2 and the IGF is IGF2. In some aspects, the neurotrophic factors are recombinant. Exemplary recombinant neurotrophic factors are available from, for example, Peprotech (Rocky Hill, N.J., USA) (e.g., rh/m/rBDNF cat #450-02, rhCTNF cat #450-13, rhGDNF cat #450-10, -NGF cat #450-01, rhNT-3 cat #450-03, rhFGF2 cat #100-18B, rhIGF2 cat #100-12, rhHGF cat #100-39, rhNOG cat #120-10C). T3 is available from, for example, Santa Cruz Biotechnology (Santa Cruz, Calif., USA) (e.g., T3 CAS #55-06-1).

As used herein, the term "neuroprotective" refers to an effect that protects neural tissue against damage, degeneration, and/or impairment of function. In some aspects, neuroprotective means that an agent or factor enhances the efficacy of certain neurological indications. Neuroprotective effects include but are not limited to proliferation of neural stem cells (assayed by flow cytometry), differentiation of glial restricted precursor cells toward oligodendrocytes (assayed by flow cytometry and/or immunohistochemistry optionally through use of organotypic brain slice cultures and/or multiple sclerosis animal studies), reduction of apoptosis of neural cells when exposed to high oxidative stress (assayed by flow cytometry), remyelination of axons (assayed by flow cytometry and/or immunohistochemistry optionally through use of organotypic brain slice cultures and/or multiple sclerosis animal studies), functional recovery in models with neurodeficits (assayed by behavioral test, immunohistochemistry, and/or flow cytometry optionally in MS animal studies), enhanced neurotrophic secretion (assayed by antibody array and/or RNA-seq, optionally in MS animal studies), and neurite outgrowth (assayed by immunohistochemistry).

Extracellular Vesicles ("EVs")

Cell-derived vesicles, also referred to as extracellular vesicles ("EV"), are membrane surrounded structures that are released by cells in vitro and in vivo. EVs can contain proteins, lipids, and nucleic acids and can mediate intercellular communication between different cells, including different cell types, in the body. Various types of extracellular vesicles exist, which include exosomes, microvesicles and secreted autophagosomes. Exosomes are small lipid-bound, cellularly secreted vesicles that mediate intercellular communication via cell-to-cell transport of proteins and RNA. See El Andaloussi, S. et al., *Nature Reviews: Drug Discovery* 12(5):347-357 (2013). Exosomes range in size from approximately 30 nm to about 200 nm and can be released from a cell by fusion of multivesicular endosomes ("MVE") with the plasma membrane.

Microvesicles ("MVs"), on the other hand, can be released from a cell upon direct budding from the plasma membrane ("PM"). Typically MVs may be larger than exosomes and range from approximately 100 nm to 1 μm.

EVs can be released from a variety of cell types and contain RNA, protein, and lipids from the cells. In one embodiment, the EVs can be released from a cell including a neuron, an immune cell, an astrocyte, an endothelial cell, a muscle cell, an oligodendrocyte, a reticulocyte, or a combination thereof. In another embodiment, the immune cell includes a T-cell, a B-cell, a dendritic cell, a macrophage, or the combination thereof.

Figure 1:
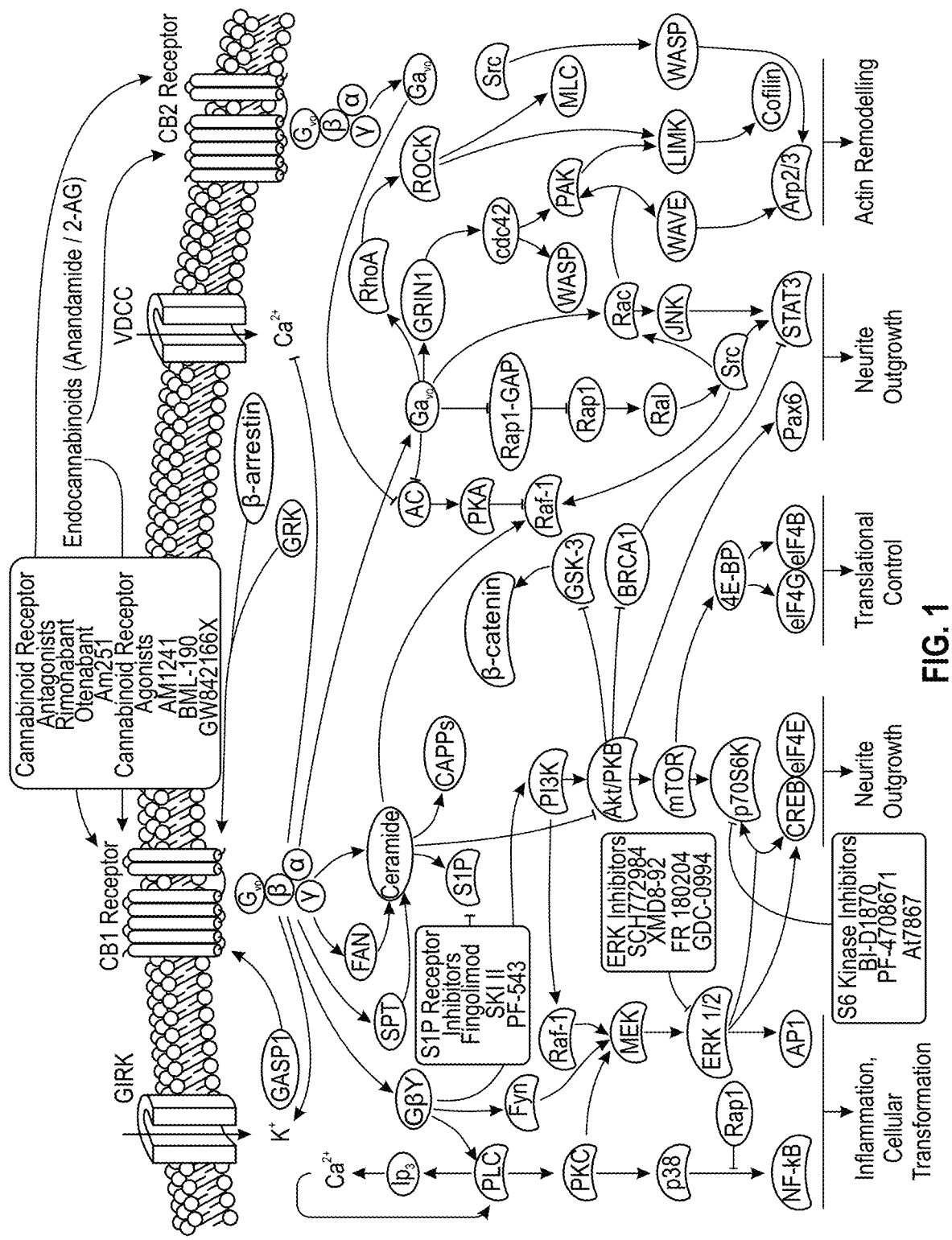
FIG. 1 shows the CB receptor mediate signal transduction pathway.

EV release also relates to a signal transduction pathway mediated by a CB1 receptor and/or a CB2 receptor. The CB1 receptor-mediated signal transduction pathways can contribute to modification of EV release with targets such as Fyn, MEK, ERK1/2, PI3K, mTOR, and CREBV/eIF4E. The CB2 receptor-mediated signal transduction pathways contribute to modification of EV release such as Src, LIMK, Cofilin, JNK, and cdc42. FIG. 1 shows a diagram of CB1- and CB2-mediated signal transduction pathways.

In another embodiment, the EVs can be released from a cell in the nervous system. The nervous system includes both the central nervous system ("CNS") and the peripheral nervous system. Non-limiting examples of cells in the nervous system include neurons, astrocytes, oligodendrocytes, microglia, ependymal cells, neurolemmocytes, satellite cells, endothelial cells (e.g., endothelial cells of the capillary wall that are related to the blood brain barrier), and pericytes.

The content in EVs also varies and depends on the cells from which they originate. In one embodiment, the EVs include proteins, mRNAs, microRNAs (miRNAs), lipids, and carbohydrates. Once released, the components within EVs can influence the local microenvironment or spread through circulation to locations far removed from their origins. Indeed, exosomes can cross the blood-brain barrier and allow coordination with the immune system in even immune-privileged sites. For example, EVs can bind to neighbor cells, travel along the blood stream to a more paracrine location, cross blood-brain barrier to the brain, or be taken up by phagocytes in spleen and liver.

Surprisingly, Applicant discovered that the pharmaceutical composition of the disclosure can inhibit release of EVs, and thus suppresses or control the viral pathogens that are delivered by EVs. In particular, treating the HIV-1 infected myeloid cells with cannabidiol ("CBD") and Δ9-tetrahydrocannabinol ("THC") can slow or inhibit the release of EVs and the subsequent production of viral particles from infected cells without altering the size of the EVs. Two viral proteins, gp120 and Nef, which are associated with viral infection, were reduced with the treatment with the cannabinoid products, azidothymidine, an interferon ("IFN"), a tetracycline antibiotic, or a combination thereof.

In one or more embodiments, the present disclosure provides pharmaceutical compositions for inhibiting release of extracellular vesicles from a cell infected by a virus, the compositions including a cannabinoid product. In at least one embodiment, the pharmaceutical composition can include, but is not limited to, azidothymidine, an interferon ("IFN"), a tetracycline antibiotic, or the combination thereof. In one or more embodiments, the cannabinoid product can include a pentyl side chain on an aromatic ring and/or a propyl side chain on an aromatic ring. In various embodiments, the cannabinoid product can include one or more of tetrahydrocannabinol ("THC"), cannabidiol ("CBD"), olivetol, cannabinol ("CBN"), cannabigerol ("CBG"), cannabichromene ("CBC"), cannabicyclol ("CBCL"), nabilone, tetrahydrocannabinolic acid ("THCA"), cannabichromenic acid ("CBCA"), cannabicyclolic acid ("CBCLA"), cannabigerolic acid ("CBGA"), cannabidiolic acid ("CBDA"), cannabinolic acid ("CBNA"), tetrahydrocannabivarin ("THCV"), cannabivarin ("CBV"), cannabidivarin ("CBDV"), cannabigerovarin ("CBGV"), cannabichromevarin ("CBCV"), cannabicyclovarin ("CBCLV"), cannabicyclovarinic acid ("CBCLVA"), cannabigerovarinic acid ("CBGVA"), tetrahydrocannabivarinic acid ("THCVA"), cannabichrome varinic acid ("CBCVA"), and/or cannabidivarinic acid ("CBDVA"). In at least one embodiment, the cannabinoid product can includes CBD, THC, or a combination thereof.

In various embodiments, viral diseases targeted by the pharmaceutical composition may be caused by a DNA virus or an RNA virus. In at least one embodiment, the virus can include, but is not limited to, human immunodeficiency virus ("HIV"), human T-cell leukemia-lymphoma virus ("HTLV"), herpes simplex virus ("HSV"), Epstein-Barr virus ("EBV"), Kaposi's sarcoma herpes virus, cytomegalovirus ("CMV"), human papilloma virus ("HPV"), hepatitis virus, and/or bunyavirus. In one or more embodiments, the virus can cause infection in the CNS and can include, but is not limited to, retroviridae (e.g., HIV, HTLV, and HERV), herpesviridae (e.g., VSV, CMV, HHV-6, HSV, and EBV), picornaviridae (e.g., nonpolio enterovirus ("NPEV"), poliovirus ("PV"), and human parchovirus ("HPeV")), flaviviridae (e.g., tick-borne encephalitis virus ("TBEV"), West Nile virus ("WNV"), zika virus ("ZIKV"), and Japanese encephalitis virus ("JEV")), filoviridae (e.g., ebola virus ("EBOV") and marburg virus ("MARV")), paramyxoviridae (e.g., measles virus ("MV") and mumps virus ("MuV")), rhabdoviridae (e.g., rabies virus ("RV")), polyomaviridae (e.g., John Cunningham virus ("JCV")), togaviridae (e.g., chikungunya virus ("CHIKV"), and/or Eastern Equine encephalitis virus ("EEV")).

In at least one embodiment, the viral disease may include a HIV-associated neurocognitive disorder. In various embodiments, the viral disease can include, but is not limited to, Alzheimer's disease, multiple sclerosis, stroke, or the combination thereof. In one or more embodiments, the HIV-associated neurocognitive disorder may include, but is not limited to, asymptomatic neurocognitive impairment ("ANI"), minor neurocognitive disorder ("MND"), HIV-associated dementia ("HAD"), or a combination thereof.

In at least one embodiment, the IFN in the pharmaceutical composition may include, but is not limited to, IFN-α, IFN-β, IFN-ε, IFN-κ, IFN-ω, IFN-γ, IFN-λ1, IFN-λ2, and/or IFN-λ3. In various embodiments, the IFN may be IFN-α. In one or more embodiments, the tetracycline antibiotic in the pharmaceutical composition may include, but is not limited to, tetracycline, chlortetracycline, oxytetracycline, demeclocycline, lymecycline, meclocycline, methacycline, minocycline, rolitetracycline, and/or tigecycline, or a combination thereof. In at least one embodiment, the tetracycline antibiotic can include, but is not limited to, tetracycline, oxytetracycline, minocycline, doxycycline, methacycline, and/or demeclocycline, or a combination thereof.

In one or more embodiments, the pharmaceutical composition may include an anti-inflammatory agent, a neurotrophic factor, a neuroprotective agent, or a combination thereof. In various embodiments, the anti-inflammatory agent may be selected from TGFβ, IL-2, IL-17, IL-35, and/or IL-37. In at least one embodiment, the neurotrophic factor may be selected from BDNF, NGF, Neurotrophin-3, FGF2, CTNF, GDNF, IGF2, HGF, Noggin, and/or T3. The pharmaceutical composition, in some embodiments, may include pharmaceutically acceptable carrier.

Applicant discovered that, in one or more embodiments, the pharmaceutical composition can inhibit or suppress the incorporation of viral components to the EVs before the EV release, and thus reduce the spread of viral components as delivered by the EVs. In at least one embodiment, the viral components may include, but are not limited to, peptides, polypeptides, proteins, nucleic acids, lipids, carbohydrates, or a combination thereof. In various embodiments, the nucleic acid includes DNA and/or RNA. In one or more embodiments, the nucleic acid includes a gene or gene fragment (for example, a probe, primer, EST, or SAGE tag), an exon, an intron, a messenger RNA (mRNA), a transfer RNA, a ribosomal RNA, a ribozyme, cDNA, dsRNA, siRNA, miRNA, a recombinant polynucleotide, a branched polynucleotide, a plasmids, a vector, an isolated DNA of any sequence, an isolated RNA of any sequence, a nucleic acid probe, or a primer.

In at least one embodiment, the reduction of viral packaging can be due to reduction in expression, transcription, replication, or alteration in packaging. Applicant found that, in various embodiments the pharmaceutical composition can inhibit transcription of viral RNAs and thus reduce the incorporation of the viral RNAs to the EVs. Thus, in one or more aspects, the present disclosure relates to methods of inhibiting transcription of a viral RNA. In one embodiment, the viral RNA may be the TAR RNA and/or the env RNA.

In one or more embodiments, exosome biogenesis, cargo packaging, and release may involve an endosomal sorting complex required for transport ("ESCRT") pathway, an autophagy pathway, and/or an ESCRT independent pathways (e.g., ceramide-associated EV biogenesis and Rab-mediated EV biogenesis). Non-limiting examples of ESCRT-associated proteins include Alix and TSG101. In at least one embodiment, lipid raft-associated proteins such as transferrin and caveolins, and other proteins involved in membrane trafficking, e.g., CD9, CD63, and CD81, which have been shown to bind to ESCRT machinery, can be enriched in EVs. In one or more embodiments, ESCRT may not be the only pathway by which exosome formation can occur as there are also ESCRT-independent methods by which proteins, lipids, and RNA can enter the endosomal pathway. For example, oligodendrocytes direct exosome formation via the ceramide pathway, while other cell types rely on oligomerization of tetraspanin complexes. In at least one embodiment, knockdown of some ESCRT components may not completely abrogate the EV product, although it may reduce the exosome production.

In another aspect, the disclosure provides compositions and methods that target a pathway for EV (or exosome) biogenesis, for example, the ESCRT machinery. In various embodiments, compositions of the present disclosure may effectively reduce the release of EVs from disease ridden cells to decrease pathogenesis.

In one or more embodiments, EVs targeted by the present disclosure may include one or more of surface proteins which include, but are not limited to, CD9, HSPA8, PDCD6IP, GAPDH, ACTB, ANXA2, CD63, SDCBP, ENO1, HSP90AA1, TSG101, PKM, LDHA, EEF1A1, YWHAZ, PGK1, EEF2, ALDOA, ANXA5, FASN, YWHAE, CLTC, CD81, ALB, VCP, TPI1, PPIA, MSN, CFL1, PRDX1, PFN1, RAP1B, ITGB1, HSPA5, SLC3A2, GNB2, ATP1A1, WHAQ, FLOT1, FLNA, CLIC1, CDC42, CCT2, A2M, YWHAG, RAC1, LGALS3BP, HSPA1A, GNAI2, ANXA1, RHOA, MFGE8, PRDX2, GDI2, EHD4, ACTN4, YWHAB, RAB7A, LDHB, GNAS, TFRC, RAB5C, ANXA6, ANXA11, KPNB1, EZR, ANXA4, ACLY, TUBA1C, RAB14, HIST2H4A, GNB1, UBA1, THBS1, RAN, RAB5A, PTGFRN, CCT5, CCT3, BSG, RAB5B, RAB1A, LAMP2, ITGA6, GSN, FN1, YWHAH, TKT, TCP1, STOM, SLC16A1, RAB8A, FN1, EDIL3, TF, ITGB1, VCAN, ANXA2, MFGE8, TGB1, TGFB2, TGFBR1, TGBFR2, TGFBI, TGFBRAP1, BASP1, COL1, COL6, GAPDH, ITGA3, FBN1, ITGAV, ITGB5, NOTCH2, SDCBP, HSPA2, HSPA8, NT5E, MRGPRF, RTN4, NEFM, INA, NRP1, HSPA9, FBN1, BSG, PRPH, FBLN1, PARP4, FLNA, YBX1, EVA1B, ADAM10, HSPG2, MCAM, POSTN, GNB2, GNB1, ANPEP, ADAM9, ATP1A1, CSPG4, EHD2, PXDN, SERPINE2, CAV1, PKM, GNB4, NPTN, CCT2, LGALS3BP, MVP, or a combination thereof.

Viral Diseases and HIV-Associated Dementia ("HAD")

Viruses have evolved many mechanisms by which to evade and subvert the immune system to ensure survival and persistence. As described herein, EVs may deliver viral cargo (e.g., viral RNAs) to neighbor cells or a distant location. In at least one embodiment, by inhibiting EV release or incorporation of viral cargo to the EVs, the present disclosure provides a method of treating viral diseases in a subject. Non-limiting examples of the viral diseases include influenza, meningitis, AIDS, dementia, fever, herpes simplex, measles, cancers, gastroenteritis, keratoconjunctivitis, pharyngitis, croup, pharyngoconjunctival fever, and pneumonia.

In at least one embodiment, a wide variety of neurological disorders may be associated with viral infection, including, but not limited to, viral meningitis, viral Encephalitis, postherpetic Neuralgia, HIV-associated Neurological Disorders (including HIV Dementia, HIV-associated Myelopathy, and HIV-associated Peripheral Neuropathy), HTLV-1 myelopathy, poliomyelitis, influenza, Reye's Syndrome, Meniere's Disease, trigeminal neuralgia, and herpes zoster. In one embodiment, the virus includes human immunodeficiency virus ("HIV"), human T-cell leukemia-lymphoma virus ("HTLV"), herpes simplex virus ("HSV"), Epstein-Barr virus ("EBV"), Kaposi's sarcoma herpes virus, cytomegalovirus ("CMV"), human papilloma virus ("HPV"), hepatitis virus, and bunyavirus. In one or more embodiments, the viral disease may include a HIV-associated neurocognitive disorder. In various embodiments, the viral disease may include Alzheimer's disease, multiple sclerosis, stroke, or a combination thereof.

In at least one embodiment, the viral disease can include a virus-associated neurocognitive disorder. In various embodiments, the neurocognitive disorder can include, but is not limited to, viral meningitis, viral Encephalitis, postherpetic Neuralgia, HIV-associated Neurological Disorders (including HIV Dementia, HIV-associated Myelopathy, and HIV-associated Peripheral Neuropathy), HTLV-1 myelopathy, poliomyelitis, influenza, Reye's Syndrome, Meniere's Disease, trigeminal neuralgia, and herpes zoster. In one or more embodiments, the HIV-associated neurocognitive disorder can include, but is not limited to, asymptomatic neurocognitive impairment (ANI), minor neurocognitive disorder (MND), HIV-associated dementia (HAD), HIV-associated myelopathy, HIV-associated peripheral neuropathy, or combinations thereof.

HIV infection causes immunosuppression and can involve other disorders, such as myelopathy, vision loss, or a dementing neurological disorder, i.e., the AIDS dementia complex. HIV infection has been documented in various areas of the CNS, including the cerebral cortex, spinal cord, and retina. See Price et al., *Science,* 239:586 (1988) and Ho et al., *Annals in Internal Medicine,* 111:400 (1989). In various embodiments, the mechanism underlying the neurological dysfunction induced by HIV may be indirect tissue damage by either viral- or cellular-derived toxic substances released by infected cells. In addition to the previously known white matter lesions present in the brains of patients with AIDS-related dementia, approximately 20% of the neurons may be damaged or die. Ketzler et al., *Acta Neuropathologica* 80:92, (1990). As used herein, the term "HIV" refers to all types and variants of HIV including HIV-1, HIV-2, LAV, and others.

HIV enters the central nervous system ("CNS") early in the course of the infection and causes several important CNS conditions over the course of the disease, such as HIV encephalopathy and AIDS dementia complex. As part of the acute HIV syndrome during seroconversion, patients may experience HIV encephalopathy. HIV-associated progressive encephalopathy ("HPE") is a syndrome complex with cognitive, motor, and behavioral features seen in children. In at least one embodiment, HIV-associated neurocognitive disorder ("HAND") includes asymptomatic neurocognitive impairment ("ANI"), minor neurocognitive disorder ("MND"), HIV-associated dementia ("HAD"), minor cognitive motor disorder ("MCMD"), HIV-associated myelopathy, HIV-associated peripheral neuropathy, or a combination thereof. In one or more embodiments, HAD may be characterized by cognitive, motor, and behavioral features in adults, usually those with advanced AIDS. In at least one embodiment, highly active antiretroviral therapy ("HAART") may be used as a therapy for treating HIV or its associated disorders. In addition to HIV itself, other causes of neurologic complications in HIV-infected individuals may include, but are not limited to, opportunistic infections, tumors, and antiretroviral drugs. Other neurologic complications that arise from primary HIV infection may include, but are not limited to, vacuolar myelopathy, peripheral neuropathies, and polymyositis.

In one or more embodiments, the HIV-related disorder can include, but is not limited to, candidiasis, coccidioidomycosis, cryptococcosis, cryptosporidiosis, cytomegalovirus, herpes simplex virus, herpes zoster, histoplasmosis, isosporiasis, *Mycobacterium avium* complex, *Pneumocystis pneumonia*, bacterial pneumonia, progressive multifocal leukoencephalopathy *Salmonella*, toxoplasmosis, and/or tuberculosis. In various embodiments, the HIV-related disorder may be an AIDS-related cancer, such as, for example, cervical cancer, Kaposi sarcoma, and/or lymphomas. In at least one embodiment, the HIV-related disorder may be an AIDS-defining illness such as, for example, candidiasis of the esophagus, bronchi, trachea, or lungs, invasive cervical cancer, disseminated or extrapulmonary coccidioidomycosis, extrapulmonary cryptococcosis, chronic intestinal cryptosporidiosis, cytomegalovirus disease (other than liver, spleen, or nodes), cytomegalovirus retinitis with loss of vision, HIV related-encephalopathy, herpes simplex (with chronic ulcers, bronchitis, pneumonitis, or esophagitis), disseminated or extrapulmonary histoplasmosis, chronic intestinal isosporiasis, Kaposi sarcoma, Burkitt's lymphoma, immunoblastic lymphoma, primary lymphoma of brain, disseminated or extrapulmonary *Mycobacterium avium* complex or *M. kansasii*, pulmonary or extrapulmonary *Mycobacterium tuberculosis*, disseminated or extrapulmonary *mycobacterium* species, *Pneumocystis jiroveci pneumonia*, recurrent pneumonia, progressive multifocal leukoencephalopathy, recurrent *Salmonella* septicemia, toxoplasmosis of brain, and/or wasting syndrome due to HIV.

In one or more embodiments, the HIV-related disorder may be a neurological disorder. In various embodiments, the neurological disorder may include, but is not limited to, AIDS dementia complex, AIDS-induced encephalopathy, HIV encephalopathy, HIV-associated progressive encephalopathy, HIV-associated neurocognitive disorder, asymptomatic neurocognitive impairment, minor neurocognitive disorder, HIV-associated dementia, minor cognitive motor disorder, vacuolar myelopathy, peripheral neuropathies, and/or polymyositis. In at least one embodiment, the neurological disorder may be AIDS dementia complex. In one or more embodiments, the neurological disorder may be AIDS-induced encephalopathy. In various embodiments, the neurological disorder may be HIV encephalopathy.

In at least one embodiment, the neurological disorder may be HIV-associated progressive encephalopathy. In one or more embodiments, the neurological disorder may be HIV-associated neurocognitive disorder. In various embodiments, the neurological disorder may include, but is not limited, ANI, MND, HAD, minor cognitive motor disorder ("MCMD"), HIV-associated myelopathy, HIV-associated peripheral neuropathy, or a combination thereof.

HAD

HIV-1 associated dementia ("HAD") or AIDS dementia complex ("ADC") may be one of the HIV-associated neurocognitive disorders and may be characterized by cognitive decline and/or fine motor dysfunction. In at least one embodiment, HAD may be progressive or relatively static. In one or more embodiments, despite the incidence of fulminant HAD declining due to the highly-active antiretroviral therapy (HAART), the incidence of a more insidious and protracted dementia, with higher CD4 counts, appears to be increasing. The precise pathophysiology of HAD remains elusive. On pathology, atrophy and white matter pallor is observed usually without frank demyelination. Despite widespread scarring (gliosis) and neuronal cell loss, HIV-1 may not directly infect neuronal cells. HIV-1 is found in macrophages in the brain, and degree of macrophage infiltration, rather than brain viral load, may correspond best to dementia severity. Proinflammatory molecules, secreted by or induced by macrophages, may be responsible for the ongoing brain injury by HIV. Toxic synergies among viral protein products (e e.g., Tat) and macrophage-derived cytokines (e.g., TNF-$\alpha$), interleukins (e.g., IL-6), and oxygen free-radical reactions (e.g., peroxynitrite) lead to enhanced vulnerability to oxidative stress in the AIDS brain, resulting in massive cell death.

HIV proteins have been implicated in the development of HAD, e.g., Nef, Tat, Env, Vpu and the LTR. See Lamers, S. L., et al., *PLoS ONE,* 6(2), e16659 (2011). Among them, Nef is a multi-factorial protein required to maintain high viral loads. The loss of Nef function may result in delayed or absent AIDS progression. Additionally, Nef may promote the survival of infected cells and migration. In the cell, Nef can bind MHC class II receptors, allowing it to interfere with a variety of cellular process such as triggering rapid CD4 endocytosis, targeting the trans-golgi network, activating phosphatidylinositol 3-kinases and lysosomal degradation. Exposure of neuronal cell cultures to Nef may result in neurotoxicity. Within the brain of HIV-1-infected patients, Nef may be found in both macrophages and astrocytes. Stable expression of Nef may alter growth properties of human astrocytes, and Nef/LTR deleted viruses have either diminished neurotropism or insufficient systemic viral replication for entry into the CNS.

In at least one embodiment, the present disclosure provides a method of treating HIV-associated dementia. In one or more embodiments, the method may include, but is not limited to, administering a therapeutically effect amount of a pharmaceutical composition that includes a cannabinoid product. In various embodiments, the pharmaceutical composition can include one or more of azidothymidine, an interferon ("IFN"), and a tetracycline. In at least one embodiment, the cannabinoid product may include a pentyl side chain on an aromatic ring and/or a propyl side chain on an aromatic ring. In one or more embodiments, the cannabinoid product may include one or more of tetrahydrocannabinol (THC), cannabidiol (CBD), olivetol, cannabinol (CBN), cannabigerol (tetrahydrocannabinol ("THC"), cannabidiol ("CBD"), olivetol, cannabinol ("CBN"), cannabigerol ("CBG"), cannabichromene ("CBC"), cannabicyclol ("CBCL"), nabilone, tetrahydrocannabinolic acid ("THCA"), cannabichromenic acid ("CBCA"), cannabicyclolic acid ("CBCLA"), cannabigerolic acid ("CBGA"), cannabidiolic acid ("CBDA"), cannabinolic acid ("CBNA"), tetrahydrocannabivarin ("THCV"), cannabivarin ("CBV"), cannabidivarin ("CBDV"), cannabigerovarin ("CBGV"), cannabichromevarin ("CBCV"), cannabicyclovarin ("CBCLV"), cannabicyclovarinic acid ("CBCLVA"), cannabigerovarinic acid ("CBGVA"), tetrahydrocannabivarinic acid ("THCVA"), cannabichrome varinic acid ("CBCVA"), and cannabidivarinic acid ("CBDVA"). In various embodiments, the cannabinoid compound may include CBD, THC, or a combination thereof.

In at least one embodiment, IFN in the pharmaceutical composition can be an IFN type 1, an IFN type 2, and/or an IFN type 3. In one or more embodiments, the IFN may include, but is not limited to, one or more of IFN-α, IFN-β, IFN-ε, IFN-κ, IFN-ω, IFN-γ, IFN-λ1, IFN-λ2, and/or IFN-λ3. In various embodiments, the IFN may be IFN-α.

In at least one embodiment, tetracycline antibiotic may be an antibiotic compound with a four hydrocarbon ring structure. In one or more embodiments, the tetracycline antibiotic can include one or more of tetracycline, chlortetracycline, oxytetracycline, demeclocycline, lymecycline, meclocycline, methacycline, minocycline, rolitetracycline, and/or tigecycline. In various embodiments, tetracycline antibiotic may include, but is not limited to, one or more of tetracycline, oxytetracycline, minocycline, doxycycline, methacycline, and/or demeclocycline.

As described, neural damage or inflammation associated with viral protein or viral infection can also lead to or exacerbate a neurological disorder. In at least one embodiment, the pharmaceutical composition may include one or more of an anti-inflammatory agent, a neurotrophic factor, and/or a neuroprotective agent. In one or more embodiments, anti-inflammatory agent may include, but is not limited to, one or more of TGFβ 1-4 ("TGFβ," e.g., TGFβ1: NP_000651; TGFβ2: NP_001129071, NP_003229; TGFβ3: NP_001316867, NP_001316868, NP_003230; TGFβ4), interleukin 2 ("IL-2," NP_000577), interleukin 10 ("IL-10," NP_000563), interleukin 17 ("IL-17," e.g., NP_002181), interleukin 35 ("IL-35"), and/or interleukin-1 family member 7 ("IL-37," NP_055254, NP_775294, NP_775295, NP_775296, NP_775297). In various embodiments, the anti-inflammatory agent may be TGFβ and/or IL-2.

In one or more embodiments, the neurotrophic factor may include, but is not limited to, one or more of brain derived neurotrophic factor (BDNF, e.g., NP_001137277), nerve growth factor (NGF, NP_002497) Neurotrophin-3 (NTF3, NP_001096124, NP_002518), ciliary neurotrophic factor (CTNF, NP_000605), glial cell derived neurotrophic factor (GDNF, e.g., NP_000505), fibroblast growth factors (FGFs) 1-23 (e.g., FGF1, NP_000791, FGF2 NP_001997), insulin-like growth factors (IGFs) (IGF1, NP_000609, IGF2 e.g., NP_000603), hepatocyte growth factor (HGF, e.g., NP_000592), Noggin (NOG, NP_005441), thyroid hormone triiodothyronine (T3, (2S)-2-amino-3-[4-(4-hydroxy-3-iodo-phenoxy)-3,5-diiodo-phenyl]propanoic acid, molecular formula C15H11I3NNaO4, available from, for example, Santa Cruz Biotechnology (Santa Cruz, Calif., USA) (e.g., T3 CAS #55-06-1)), or equivalents of each thereof. In at least one embodiment, the one or more neurotrophic factors may include, but are not limited to, one or more of FGF2, T3, NOG, BDNF, NGF, HGF, CTNF, GDNF, and/or IGF2. In various embodiments, the neurotrophic factors may include, but are not limited to, one or more of BDNF, NGF, Neurotrophin-3, FGF2, CTNF, GDNF, IGF2, HGF, Noggin, and/or T3.

Neurological symptoms associated with HAD may have been treated with previous drugs that have a number of shortcomings. For example, the psychosis associated with HIV dementia has been treated with haloperidol and thioridazine. Molindone has been used for psychotic and delirious HIV dementia patients. Methylphenidate has been used for treatment of depression associated with HAD. Electroconvulsive therapy has been used for HIV-induced stupor. All of these treatments serve to ameliorate symptoms of HAD. Thus, in at least one aspect, the methods of the present disclosure may include, but are not limited to, treating the subject with a therapeutic that is capable of ameliorating symptoms of HAD. In one or more embodiments, the therapeutic capable of ameliorating symptoms of HAD may include, but is not limited to, one or more of haloperidol, thioridazine, molindone, or a combination thereof. In at least one embodiment, the therapeutic may include an electroconvulsive therapy.

Dosage and Formulation

In various embodiments, in the pharmaceutical composition, cannabinoid product, azidothymidine, the interferon ("IFN"), and/or the tetracycline antibiotic may be formulated together, separately, either in bulk or in unit dosage forms. In at least one embodiment, if formulated separately, the active agents may be administered together or separately (e.g., at different intervals of time).

In various embodiments, biological concentration of the compounds of the present disclosure can be measured by any method known in the biochemical art. For example, the biological concentration of the pharmaceutical composition can be measured in a blood or tissue sample that is obtained from a subject following the administration of the cannabinoid product.

In one or more embodiments, any analytical technique, for example, high performance reverse-phase liquid chromatography or UV-Vis spectroscopy, can be used to measure the biological concentration of the cannabinoid product. In one example, the biological concentration of the pharmaceutical composition of this disclosure can be measured by comparing the area under a curve of a plasma sample from a patient to whom the pharmaceutical composition is administered to a standard curve that is generated prior to analysis of the biological sample.

In at least one embodiment, the concentration of the cannabinoid product, the azidothymidine, the IFN, or the tetracycline antibiotic can be in the range from 0.1 ng/mL to 50 ng/mL per milligram of the pharmaceutical composition administered to the subject. In one or more embodiments, the concentration can be in the range from 0.1 ng/mL to 25 ng/mL per milligram of the pharmaceutical composition administered to the subject, from 0.1 ng/mL to 15 ng/mL per milligram of the pharmaceutical composition administered to the subject, from 0.1 ng/mL to 10 ng/mL per milligram of the pharmaceutical composition administered to the subject, or from 0.1 ng/mL to 5 ng/mL per milligram of the pharmaceutical composition administered to the subject.

In various embodiments, the biological concentration can be in the range from 2 ng/mL to 25 ng/mL per milligram of the pharmaceutical composition administered to the subject, from 2 ng/mL to 20 ng/mL per milligram of the pharmaceutical composition administered to the subject, from 2 ng/mL to 15 ng/mL per milligram of the pharmaceutical composition administered to the subject, from 2 ng/mL to 10 ng/mL per milligram of the pharmaceutical composition administered to the subject, or from 2 ng/mL to 5 ng/mL per milligram of the pharmaceutical composition administered to the subject.

In at least one embodiment, a pharmaceutical composition can include, but is not limited to, a pharmaceutically acceptable salt, solvate, and/or stereoisomer of the cannabinoid product, the azidothymidine, or the tetracycline antibiotic, according to the present disclosure, in admixture with a pharmaceutically acceptable carrier. In one or more embodiments, the composition can contain one or more additional therapeutic agents, pharmaceutically acceptable excipients, diluents, adjuvants, stabilizers, emulsifiers, preservatives, colorants, buffers, and/or flavor imparting agents (e.g., in accordance with accepted practices of pharmaceutical compounding).

In various embodiments, the present pharmaceutical compositions may be administered orally, topically, parenterally, by inhalation or spray or rectally in dosage unit formulations. As used herein the term parenteral includes, but is not limited to, subcutaneous injections, intravenous, intramuscular, intrasternal injection, and/or infusion techniques.

In one or more embodiments, suitable oral compositions can include, but are not limited to, tablets, troches, lozenges, aqueous or oily suspensions, dispersible powders or granules, emulsion, hard or soft capsules, syrups and/or elixirs.

In at least embodiment, the present pharmaceutical compositions may be suitable for single unit dosages that include a prodrug of the pharmaceutical composition in its pharmaceutically acceptable stereoisomer, salt, solvate, hydrate, and/or tautomer, and a pharmaceutically acceptable carrier.

In at least one embodiment, compositions suitable for oral use may be prepared according to any suitable method for the manufacture of pharmaceutical compositions. For example, liquid formulations of prodrugs of the present pharmaceutical compositions may contain one or more agents including, but not limited to, sweetening agents, flavoring agents, coloring agents, and/or preserving agents in order to provide pharmaceutically elegant and palatable preparations of the prodrugs.

In one or more embodiments, for tablet compositions of the present pharmaceutical compositions, active ingredient in admixture with non-toxic pharmaceutically acceptable excipients may be used for the manufacture of tablets. Examples of such excipients include, without limitation, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example, magnesium stearate, stearic acid, or talc. In at least one embodiment, the tablets may be uncoated or may be coated by coating techniques to delay disintegration and absorption in the gastrointestinal tract and thereby to provide a sustained therapeutic action over a desired time period. For example, a time delay material such as glyceryl monostearate or glyceryl distearate may be employed.

In one or more embodiments, formulations for oral use may be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

For aqueous suspensions, various embodiments of the present compounds and formulations can be admixed with excipients suitable for maintaining a stable suspension. Examples of such excipients include, without limitation, sodium carboxymethylcellulose, methylcellulose, hydropropylmethylcellulose, sodium alginate, polyvinylpyrrolidone, gum tragacanth, and gum acacia.

In at least one embodiment, oral suspensions can contain dispersing or wetting agents, such as naturally occurring phosphatide, for example, lecithin, polyoxyethylene stearate, heptadecaethyleneoxycetanol, polyoxyethylene sorbitol monooleate, polyethylene sorbitan monooleate. In one or more embodiments, the aqueous suspensions may also contain one or more preservatives, for example, ethyl, or n-propyl p-hydroxybenzoate, one or more coloring agents, one or more flavoring agents, and/or one or more sweetening agents, such as sucrose or saccharin.

In various embodiments, oily suspensions may be formulated by suspending the present pharmaceutical compositions in a vegetable oil, for example, *arachis* oil, olive oil, sesame oil, or coconut oil, or in a mineral oil such as liquid paraffin. In at least one embodiment, the oily suspensions may contain a thickening agent, for example, beeswax, hard paraffin, or cetyl alcohol.

In one or more embodiments, syrups and elixirs may be formulated with sweetening agents, for example, glycerol, propylene glycol, sorbitol, or sucrose. In various embodiments, the formulations may include, but are not limited to, a demulcent, a preservative, and flavoring and coloring agents. In at least one embodiment, the present pharmaceutical compositions may be in the form of a sterile injectable or an aqueous suspension. In one or more embodiments, the suspension may be formulated according to the known art using those suitable dispersing or wetting agents and suspending agents. In various embodiments, the sterile injectable preparation may also be sterile injectable solution or suspension in a non-toxic parentally acceptable diluent or solvent, for example, as a solution in 1,3-butanediol. In at least one embodiment, acceptable vehicles and solvents that may be employed include, but are not limited to, water, Ringer's solution, and isotonic sodium chloride solution. In one or more embodiments, sterile, fixed oils may be employed as a solvent or suspending medium. In various embodiments, any bland fixed oil may be employed including synthetic mono- or diglycerides. In at least one embodiment, fatty acids such as oleic acid may be used in the preparation of injectables.

In one or more embodiments, compositions for parenteral administrations may administered in a sterile medium. In various embodiment, depending on the vehicle used and concentration the concentration of the drug in the formulation, the parenteral formulation can be a suspension or a solution containing dissolved drug. In at least one embodiment, adjuvants such as local anesthetics, preservatives, and buffering agents can be added to parenteral compositions.

In one or more embodiments, total amount by weight of a cannabinoid product, azidothymidine, an interferon ("IFN"), and/or a tetracycline antibiotic in a pharmaceutical composition may be from about 0.1% to about 95%. By way of illustration, the amount of a cannabinoid product by weight of the pharmaceutical composition, such as CBD or THC, of the present technology can be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

In at least one embodiment, the pharmaceutical composition includes a total amount by weight of a cannabinoid product at about 1% to about 10%; about 2% to about 10%; about 3% to about 10%; about 4% to about 10%; about 5% to about 10%; about 6% to about 10%; about 7% to about 10%; about 8% to about 10%; about 9% to about 10%; about 1% to about 9%; about 2% to about 9%; about 3% to about 9%; about 4% to about 9%; about 5% to about 9%; about 6% to about 9%; about 7% to about 9%; about 8% to about 9%; about 1% to about 8%; about 2% to about 8%; about 3% to about 8%; about 4% to about 8%; about 5% to about 8%; about 6% to about 8%; about 7% to about 8%; about 1% to about 7%; about 2% to about 7%; about 3% to about 7%; about 4% to about 7%; about 5% to about 7%; about 6% to about 7%; about 1% to about 6%; about 2% to about 6%; about 3% to about 6%; about 4% to about 6%; about 5% to about 6%; about 1% to about 5%; about 2% to about 5%; about 3% to about 5%; about 4% to about 5%; about 1% to about 4%; about 2% to about 4%; about 3% to about 4%; about 1% to about 3%; about 2% to about 3%; or about 1% to about 2%.

In various embodiments, compositions disclosed herein may further include a carrier, for example, a pharmaceutically acceptable carrier. In one or more embodiments, more than one pharmaceutically acceptable carrier can be used. In at least one embodiment, any pharmaceutically acceptable carrier known to those of skill in the art may be used. In various embodiments, the pharmaceutically acceptable carrier may be a preservative, for example, a polymeric preservative or a stabilizing agent.

In one or more embodiments, the pharmaceutically acceptable carrier may be selected from the group consisting of a polyethylene glycol (PEG) (e.g., PEG 150 Distearate), honey, a large molecular weight protein (e.g., bovine serum albumin or soy protein), polyvinyl alcohol, glyceryl monostearate, hyaluronic acid, glycerin, preferably vegetable-derived, proteins, preferably hydrolyzed proteins, (e.g., soy protein and silk protein), Vaseline, citrosept, parabens, xanthan gum, carrageenan, phytagel, Carbopol® polymers, and polyvinyl pyrrolidone.

In one or more embodiments, the pharmaceutically acceptable carrier may include, but is not limited to, polyethylene glycol (PEG) (e.g., PEG 150 Distearate), honey, a large molecular weight protein (e.g., bovine serum albumin or soy protein), polyvinyl alcohol, glyceryl monostearate, hyaluronic acid, glycerin, preferably vegetable-derived, proteins, preferably hydrolyzed proteins, (e.g., soy protein and silk protein), Vaseline, citrosept, parabens, xanthan gum, carrageenan, phytagel, Carbopol® polymers, and/or polyvinyl pyrrolidone.

In at least one embodiment, non-aqueous pharmaceutically acceptable carriers may include, but are not limited to, fixed oils, vegetable oils, such as olive oil and sesame oil, triglycerides, propylene glycol, and/or polyethylene glycol. In one or more embodiments, injectable organic esters, such as ethyl oleate, can be used.

In various embodiments, pharmaceutically acceptable carrier can contain minor amounts of additives, such as substances that enhance isotonicity, chemical stability, and/or cellular stability. Examples of buffers may include, but are not limited to, phosphate buffer, bicarbonate buffer, and Tris buffer, while examples of preservatives may include, but are not limited to, thimerosal, cresols, formalin, and benzyl alcohol. In one or more embodiments, the pH can be modified depending upon the mode of administration. In at least one embodiment, the composition has a pH in the physiological pH range, such as pH 7 to 9.

In various embodiments, depending on the type of a pharmaceutically acceptable carrier used, the compositions described herein can include about 0.1-100%, 0.1-50%, or 0.1-30%, such as 0.1%, 0.25%, 0.5%, 0.75%, 1%, 2%, 5%, 7%, 10%, 15%, 20%, 25%, 30%, 40%, 40%, 50%, 55%, 60%, 65%, 70%, 75%, 80%, 85%, 90%, or 95% of the pharmaceutically acceptable carrier used in the total weight of the composition, or any range between two of the numbers (end point inclusive).

In one or more embodiments, any one of the above listed pharmaceutically acceptable carriers may be expressly excluded.

Applications and Uses

In various embodiments, pharmaceutical compositions described herein can be used in numerous medical applications including, but not limited to, treating viral diseases, inhibiting transcription of a viral RNA or release of extracellular vesicles from a cell, inhibiting packaging of a viral component into extracellular vesicles, and reducing damage to neurons from the central neural system ("CNS") or neuroinflammation.

In at least one embodiment, the present disclosure relates to treating a viral disease in a subject in need thereof, the method including administering to the subject a therapeutically effective amount of the pharmaceutical composition. In one or more embodiments, the pharmaceutical composition includes, but is not limited to, a cannabinoid product, azidothymidine, an interferon ("IFN"), a tetracycline antibiotic, or combinations thereof. In at least one embodiment, the viral disease may be caused by human immunodeficiency virus ("HIV"), human T-cell leukemia-lymphoma virus ("HTLV"), herpes simplex virus ("HSV"), Epstein-Barr virus ("EBV"), Kaposi's sarcoma herpes virus, cytomegalovirus ("CMV"), human papilloma virus ("HPV"), hepatitis virus, and bunyavirus. In one or more embodiments, the viral disease may be a neurological disorder, which can include, but is not limited to, viral meningitis, viral encephalitis, postherpetic neuralgia, HIV-associated neurocognitive disorders, HTLV-1 associated myelopathy, poliomyelitis, influenza, Reye's Syndrome, Meniere's Disease, trigeminal neuralgia, or herpes zoster.

In various embodiments, provided herein are methods for inhibiting transcription of a viral RNA or release of extracellular vesicles from a cell including contacting the cell with the pharmaceutical composition of the present disclosure. In one or more embodiments, the cell may be a neuron, an immune cell, an astrocyte, an endothelial cell, a muscle cell, an oligodendrocyte, a reticulocyte, or a combination thereof. In at least one embodiment, the immune cell may include, but is not limited to, a T-cell, a B-cell, a dendritic cell, a macrophage, or combination thereof. In various embodiments, the extracellular vesicles may include an exosome and/or a microvesicle.

In one or more embodiments, the pharmaceutical composition can be administered any suitable means based on the subject and the purpose. In at least one embodiment, the pharmaceutical composition is administered by intravenous injection, intrathecal injection, direct injection, intramuscular injection, intracranial injection, intranasally, or topically.

In various embodiments, provided herein are methods for reducing damage to a neuron from the central neural system ("CNS") or neuroinflammation in a subject, including administering to the subject a therapeutically effective amount of a pharmaceutical composition of the present disclosure. In one or more embodiments, the damage may be caused by HIV and/or HTLV.

In at least one embodiment, the pharmaceutical composition can be administered any suitable means based on the subject and the purpose. In one or more embodiments, the pharmaceutical composition may be administered by intravenous injection, intrathecal injection, direct injection, intramuscular injection, intracranial injection, intranasally, or topically.

In various embodiments, methods to determine and monitor the therapy are known in the art and briefly described herein. In one or more embodiments, when delivered in vitro, administration may be performed by contacting the composition with the tissue or cell by any appropriate method, e.g., by administration to cell or tissue culture medium, and administration may be useful as a screen to determine if the therapy is appropriate for an individual or to screen for alternative therapies to be used as a substitute or in combination with the disclosed compositions. In at least one embodiment, when administered in vivo, administration may be by systemic or local administration. In various embodiments, in vivo, the methods can be practiced on a non-human animal to screen alternative therapies to be used as a substitute or in combination with the disclosed compositions prior to human administration. In a human or non-human mammal, the methods may be useful to treat the disease or disorder.

Kits

In various embodiments, the agents and/or compositions described herein may be assembled into pharmaceutical or diagnostic or research kits to facilitate their use in therapeutic, diagnostic, or research applications. In at least one embodiment, a kit may include one or more containers housing the components of the invention and instructions for use. In one or more embodiments, kits may include one or more agents and/or compositions described herein, along with instructions describing the intended application and the proper use thereof. In various embodiments, agents in a kit may be in a pharmaceutical formulation and dosage suitable for a particular application and for a method of administration of the agents. In one or more embodiments, kits for research purposes may contain the components in appropriate concentrations or quantities for running various experiments.

In at least one embodiment, the kit may be designed to facilitate use of the methods described herein, and the kit can take many forms. In one or more embodiments, each of the compositions of the kit, where applicable, may be provided in liquid form (e.g., in solution), or in solid form, (e.g., a dry powder). In various embodiments, the compositions may be constitutable or otherwise processable (e.g., to an active form), for example, by the addition of a suitable solvent or other species (for example, water or a cell culture medium), which may or may not be provided with the kit. In at least one embodiment, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In one or more embodiments, the preservation solution may contain an amount of metalloprotease inhibitors.

As used herein, "instructions" can define a component of instruction and/or promotion, and typically involve written instructions on or associated with packaging of the invention. In at least one embodiment, instructions also can include any oral or electronic instructions provided in any manner such that a user will clearly recognize that the instructions are to be associated with the kit, for example, audiovisual (e.g., videotape, DVD, etc.), internet, and/or web-based communications, etc. In various embodiments, the written instructions may be in a form prescribed by a governmental agency regulating the manufacture, use, or sale of pharmaceuticals or biological products, which instructions can also reflect approval by the agency of manufacture, use, or sale for animal administration.

In one or more embodiments, the kit may contain, in one or more containers, any of the one or more of the components described herein. As an example, in one embodiment, the kit may include instructions for mixing one or more components of the kit and/or isolating and mixing a sample and applying to a subject. In at least one embodiment, the kit may include a container housing agents described herein. In various embodiments, the agents may be in the form of a liquid, gel, or solid (powder). In one or more embodiments, the agents may be prepared sterilely, packaged in syringe and shipped refrigerated. In at least one embodiment, the agents may be housed in a vial or other container for storage, and a second container may have other agents prepared sterilely. In one or more embodiments, the kit may include the active agents premixed and shipped in a syringe, vial, tube, or other container. In various embodiments, the kit may have one or more or all of the components required to administer the agents to a subject, such as a syringe, topical application devices, or IV needle tubing and bag.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Inhibition of EV Release

Figure 2A:
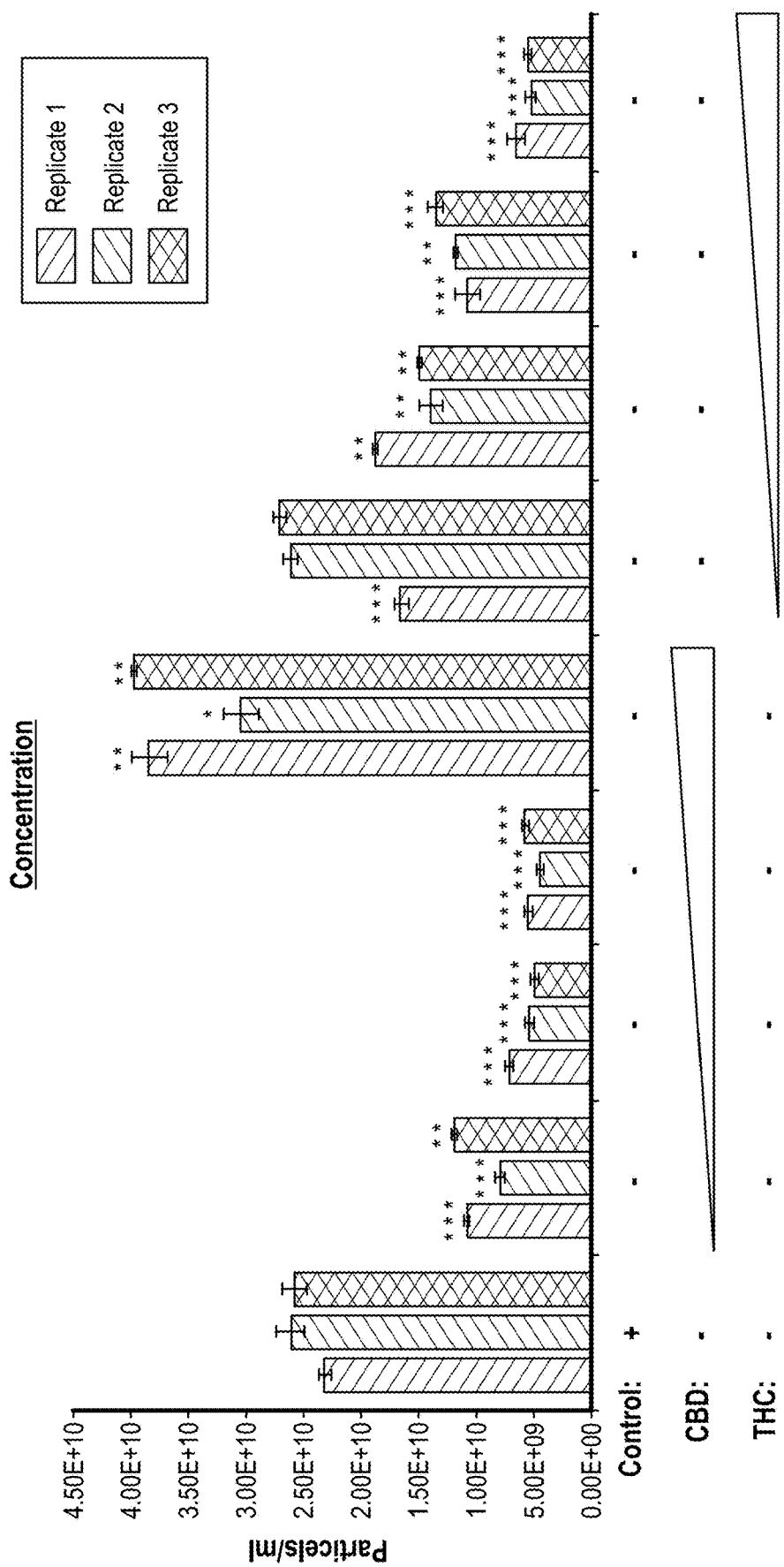
FIG. 2A shows that cannabinoids reduced the release of extracellular vesicles and altered the cargo in the extracellular vesicles. HIV-1 infected monocytes (U1) were treated with cannabidiol ("CBD") (1, 5, 20, and 50 µM) or with tetrahydrocannabinol ("THC") (1, 5, 20, and 50 µM) for 5 days. The supernatants from the treated cells were analyzed by Zeta View Nanoparticle Tracking analysis for changes in concentration. Student's t-test was used to determine significance (*=p<0.001, =p<0.01, *=p<0.05).
Figure 2B:
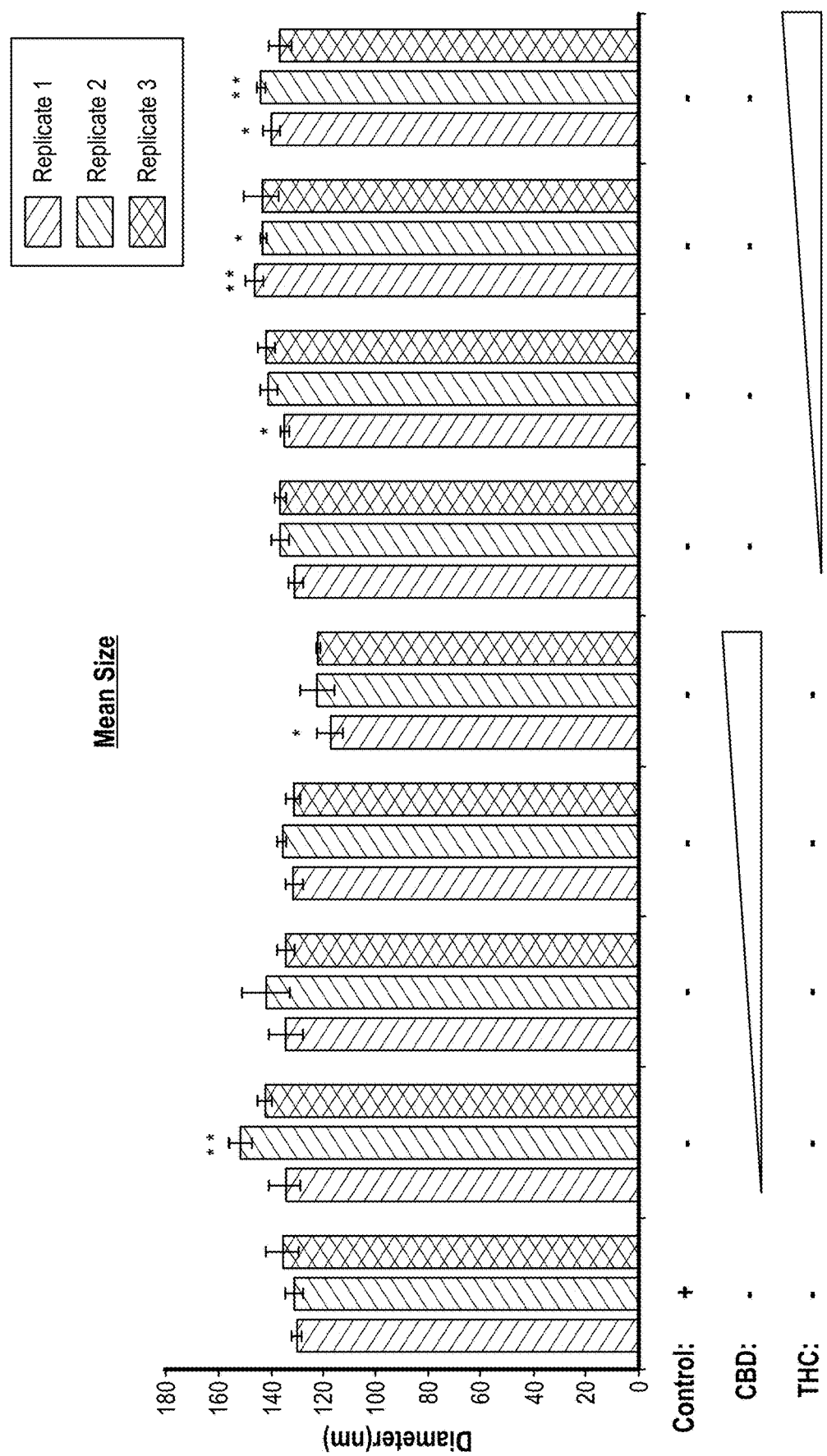
FIG. 2B shows that cannabinoids reduced the release of extracellular vesicles and altered the cargo in the extracellular vesicles. HIV-1 infected monocytes (U1) were treated with cannabidiol ("CBD") (1, 5, 20, and 50 µM) or with tetrahydrocannabinol ("THC") (1, 5, 20, and 50 µM) for 5 days. The supernatants from the treated cells were analyzed by Zeta View Nanoparticle Tracking analysis for changes in mean size. Student's t-test was used to determine significance (*=p<0.001, =p<0.01, *=p<0.05).
Figure 2C:
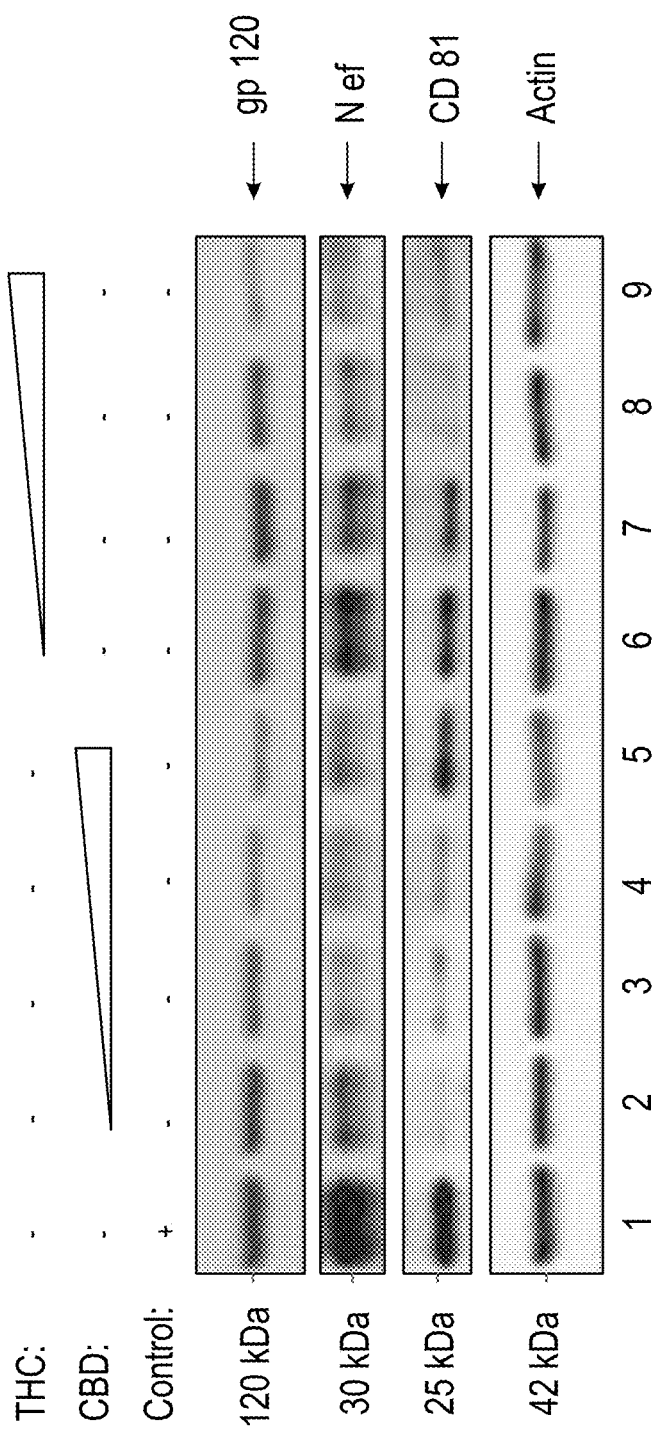
FIG. 2C shows that cannabinoids reduced the release of extracellular vesicles and altered the cargo in the extracellular vesicles. HIV-1 infected monocytes (U1) were treated with cannabidiol ("CBD") (1, 5, 20, and 50 μM) or with tetrahydrocannabinol ("THC") (1, 5, 20, and 50 μM) for 5 days. The supernatants from the treated cells were analyzed by Zeta View Nanoparticle Tracking analysis for changes in concentration and mean size. Student's t-test was used to determine significance (*=p<0.001, =p<0.01, *=p<0.05).

HIV-1 infected monocytes (U1) were treated with a titration of CBD (1, 5, 20, and 50 µM) or a titration of THC (1, 5, 20, and 50 μM) for 5 days. Resulting supernatants from the treated cells were analyzed by Zeta View Nanoparticle Tracking analysis for changes in concentration (FIG. 2A) or mean size (FIG. 2B). As shown in FIG. 2A, cannabidiol (CBD) and Δ9-tetrahydrocannabinol (THC) significantly reduced the release of EVs from the treated cells, without altering the size of the EV (FIG. 2B). Moreover, FIG. 2C indicated that there was a dose-dependent decrease in EV-associated gp120 (a glycoprotein which can facilitate the binding of the HIV-1 virus to CD4 receptors on host cells), and Nef (a small HIV protein which promotes high viral titers and has been implicated in HIV-1 associated neurotoxicity). A reduction in released EVs was further confirmed by the reduction in CD81, a tetraspanin which is commonly used as an EV marker.

Figure 3A:
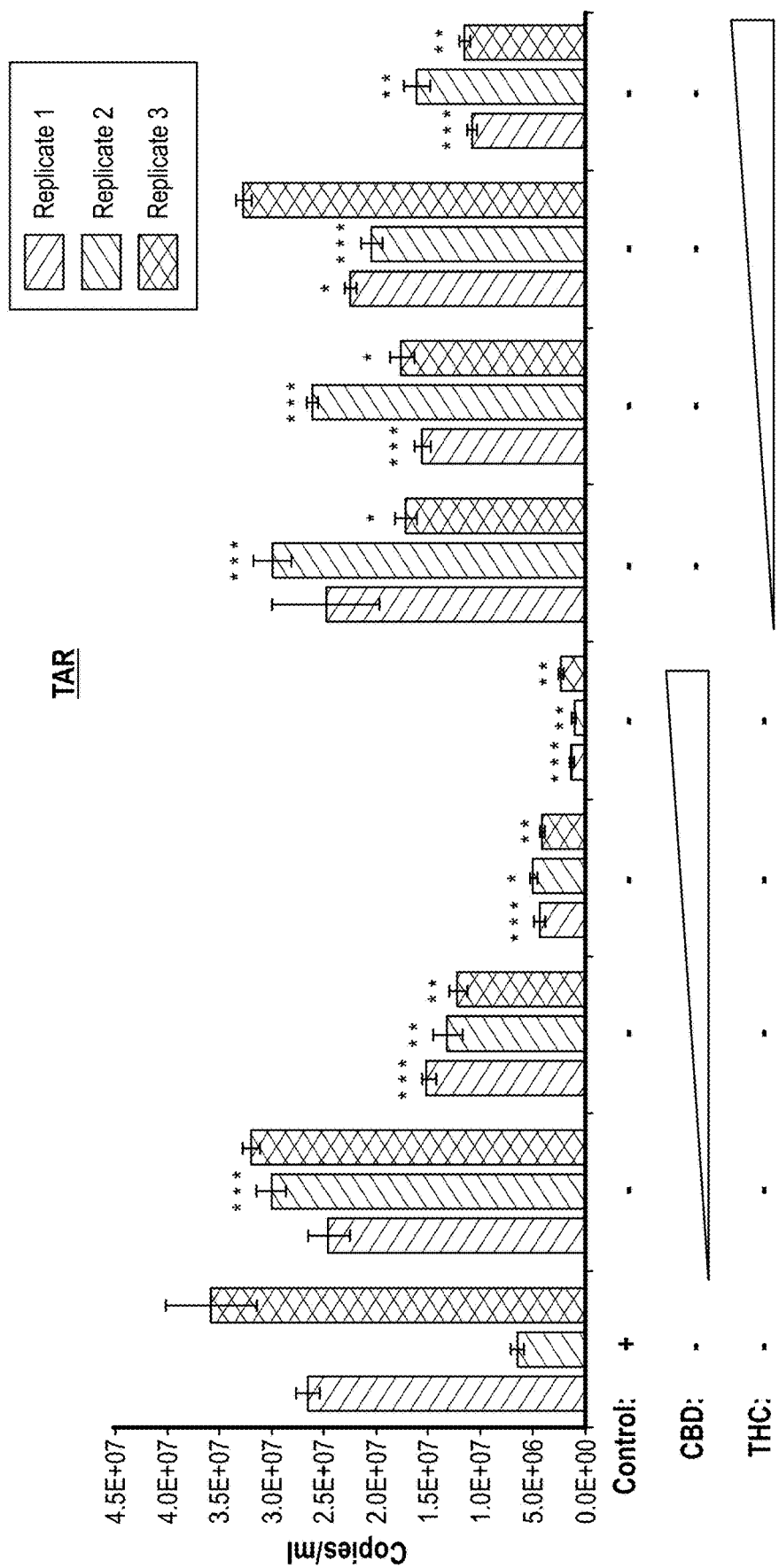
FIG. 3A shows that cannabinoids reduced release of HIV-1 short non-coding and genomic RNAs in extracellular vesicles. HIV-1 infected monocytes (U1) were treated with CBD (1, 5, 20, and 50 μM) or THC (1, 5, 20, and 50 μM) for 5 days. Extracellular vesicles were enriched from the resulting supernatant using NT 80/82. Total RNA was isolated from extracellular vesicles and analyzed using RT-qPCR for TAR RNA. Student's t-test was used to determine significance (*=p<0.001, =p<0.01, *=p<0.05).
Figure 3B:
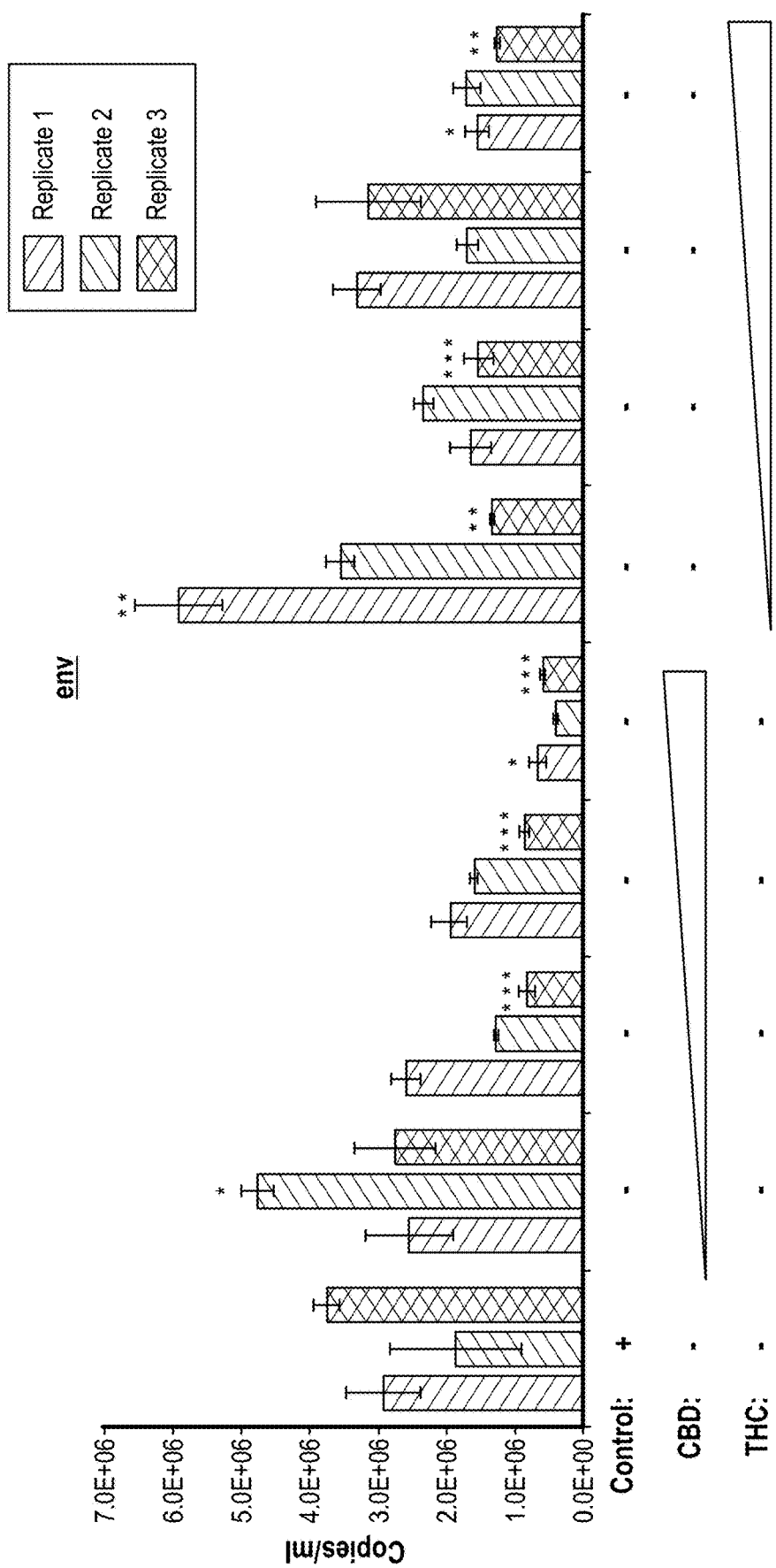
FIG. 3B shows that cannabinoids reduced release of HIV-1 short non-coding and genomic RNAs in extracellular vesicles. HIV-1 infected monocytes (U1) were treated with CBD (1, 5, 20, and 50 μM) or THC (1, 5, 20, and 50 μM) for 5 days. Extracellular vesicles were enriched from the resulting supernatant using NT 80/82. Total RNA was isolated from extracellular vesicles and analyzed using RT-qPCR for env RNA. Student's t-test was used to determine significance (*=p<0.001, =p<0.01, *=p<0.05).

The incorporation of viral RNA including TAR RNA, a short, non-coding RNA, and genomic RNA (env) have been implicated in EV-associated pathogenesis. The HIV-1 infected monocytes (U1) with the same treatments (CBD and THC) were evaluated for their RNA contents. Extracellular vesicles were enriched from the resulting supernatant using NT 80/82. Total RNA was isolated from extracellular vesicles and analyzed using RT-qPCR for (FIG. 3A) TAR RNA and (FIG. 3B) env RNA. FIG. 3 show that treatment with either CBD or THC resulted in a statistically significant, dose-dependent decrease in the incorporation of both viral RNAs—TAR (FIG. 3A) and env (FIG. 3B)—into EVs.

Figure 4A:
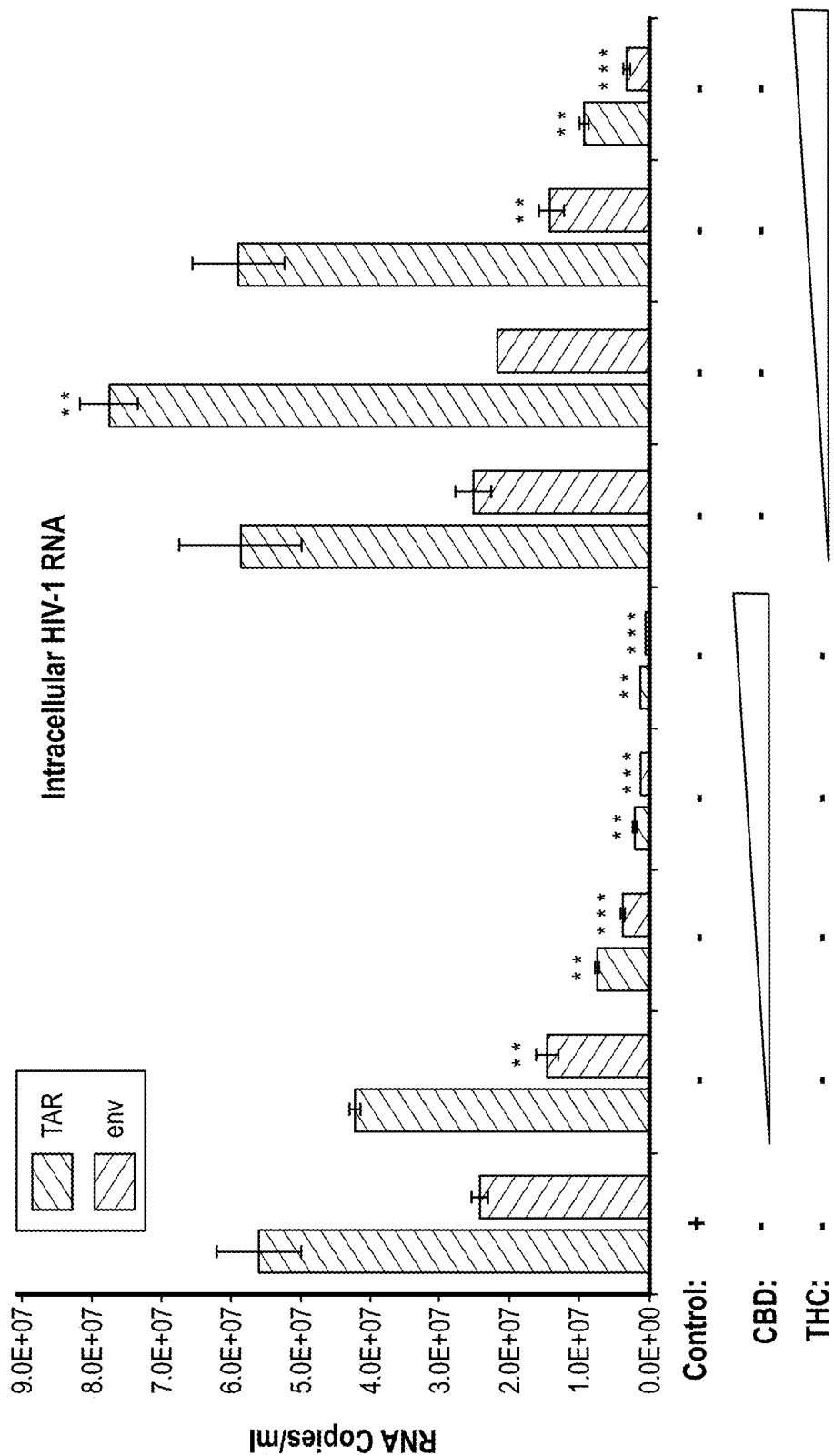
FIG. 4A shows differential HIV-1 transcriptional regulation by cannabinoids. HIV-1 infected monocytes (U1) were treated with CBD (1, 5, 20, and 50 μM) or THC (1, 5, 20, and 50 μM) for 5 days. Total RNA was isolated from cell pellets and analyzed by RT-qpCR for TAR RNA and env RNA. Student's t-test was used to determine significance (*=p<0.001, and=p<0.01).
Figure 4B:
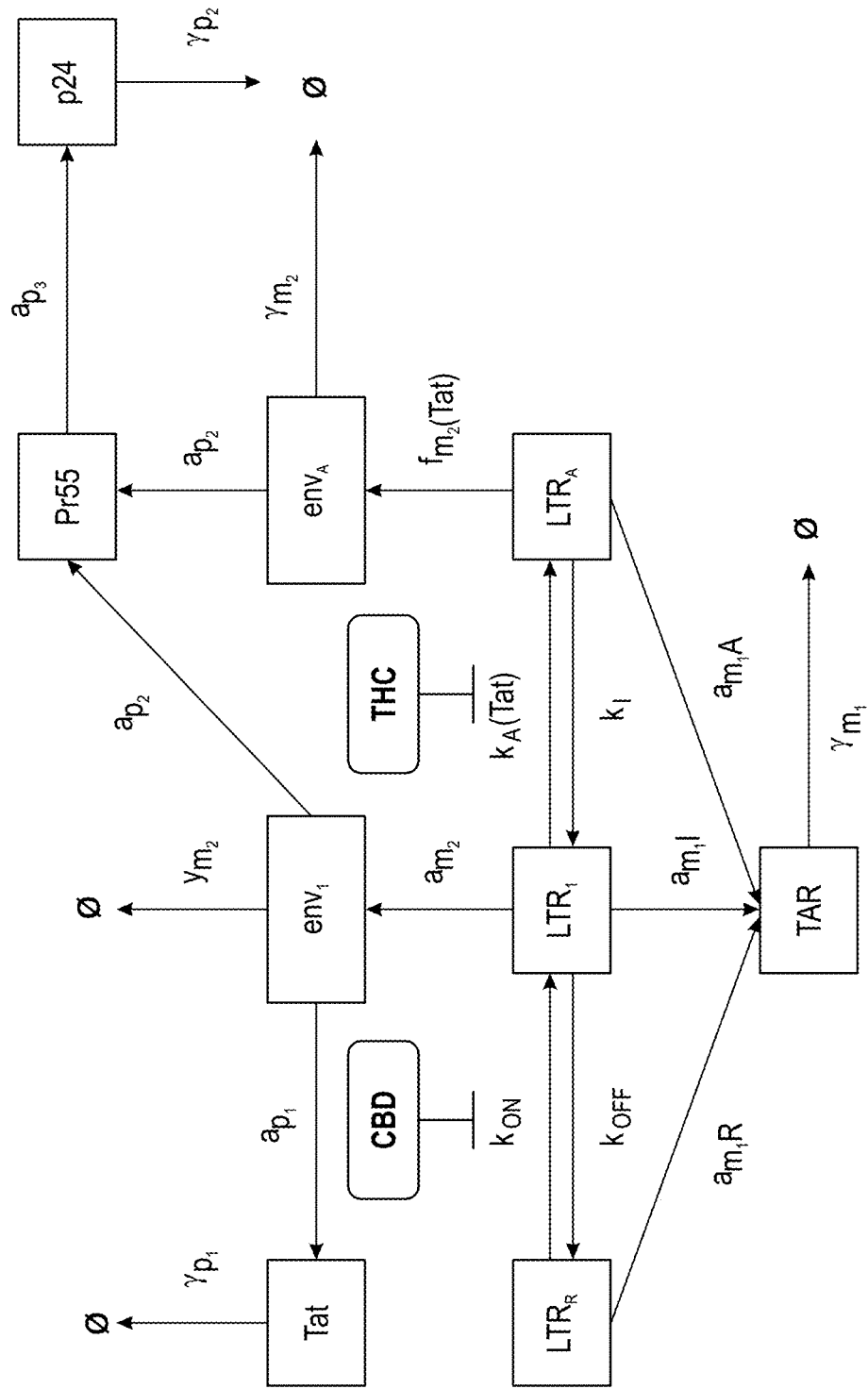
FIG. 4B shows a schematic diagram of a three-state LTR mathematical model of HIV-1 transcription which depicts production of viral RNA (TAR and env) and protein (Pr55 and p24) which can be used to model the effects of cannabinoids on HIV-1 transcription.

To determine if the observed reduction in EV-associated viral RNA was a result of a decrease in HIV-1 transcription rather than an alteration in the packaging of these viral RNAs into EVs, intracellular RNA was analyzed to assess for changes HIV-1 transcription. The data in FIG. 4A show that there was a reduction in HIV-1 transcription as a result of cannabinoid treatment. Interestingly, treatment with CBD resulted in a decrease of both transcripts (short, non-coding RNA and full-length genomic RNA; TAR and env, respectively) while THC only resulting in a decrease in the env RNA. Without being bound by a theory, these findings may suggest that there are potentially two independent mechanisms of HIV-1 transcription inhibition elicited by the two cannabinoids. The differences in inhibition of short transcripts imply targeting at different stages of transcription with CBD inhibiting transcription initiation and THC inhibiting transcription elongation. These differences in transcriptional regulation can be further analyzed using a three-state L TR mathematical model to depict changes in viral RNA and protein production over extended periods of time (FIG. 4B).

Figure 5A:
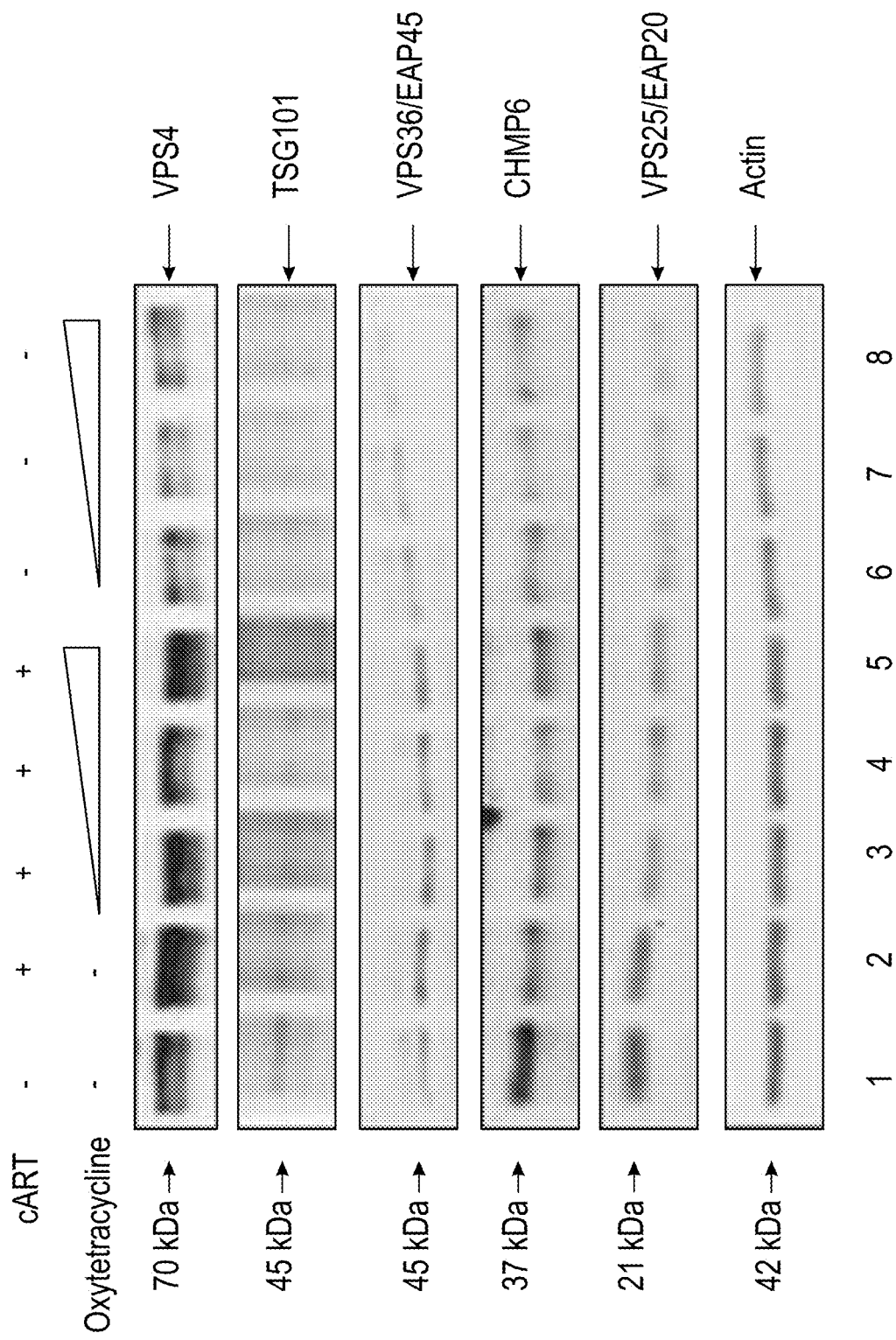
FIG. 5A shows that tetracycline class antibiotics altered EV cargo via binding of the VPS4 protein of the endosomal sorting complex required for transport (ESCRT) pathway. U1 cells were pretreated with cART (45 μM) for 3 days followed by an additional dose of cART and tetracycline antibiotics (10 nM) for 5 days. Cells were lysed, and extracts were used for Western blot analysis for ESCRT proteins [ESCRT-1 (TSG101), -11 (EAP20, EAP45), -III (CHMP6), and exit (VPS4)] and Actin levels. Resulting complexes were pulled down using streptavidin-sepharose beads.
Figure 5B:
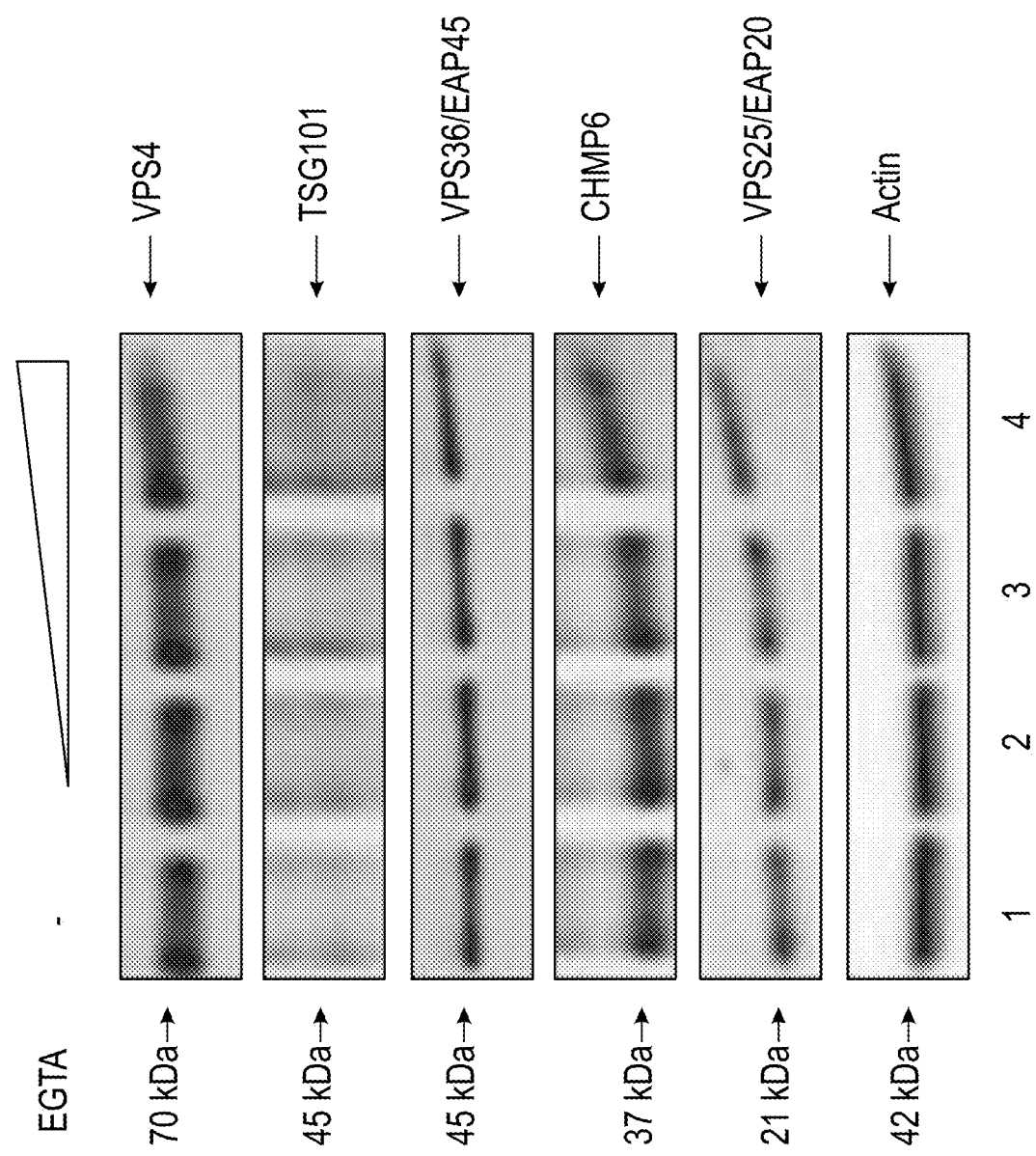
FIG. 5B shows that tetracycline class antibiotics altered EV cargo via binding of the VPS4 protein of the endosomal sorting complex required for transport (ESCRT) pathway. U1 cells were treated with a titration of ethylene glycol-bis (p-aminoethyl ether)-N,N,N',N'-tetraacetic acid (EGTA) (0.1, 1, and 10 μM) for 5 days and whole cell extracts were analyzed by Western blot for ESCRT pathway proteins and Actin.

Tetracycline class antibiotics including tetracycline, oxytetracycline, minocycline, doxycycline, methacycline, and demeclocycline have the potential to mitigate EV-associated pathogenesis by also modulating EV release. The results in FIG. 5A show that oxytetracycline downregulates VPS4 of the endosomal sorting complex required for transport (ESCRT) pathway to modulate EV dynamics. The tetracycline antibiotic family are chelators of divalent cations, including Ca2+ and Mg2+. Therefore, Applicant also tried to determine whether the chelating property of Oxytetracycline could possibly be responsible for the manipulation of the ESCRT pathway proteins levels. Results in FIG. 5B show there was no change in the levels of measured ESCRT proteins, indicating that the chelating properties of the tetracycline family of drugs are likely not responsible for the alteration of ESCRT protein levels or EV biogenesis. Results in FIG. 5C show an increase in the amount of VPS4 bound to both methacycline and doxycycline within whole cell extracts (lanes 4 and 5, respectively) in comparison to the control (lane 2).

Densitometry analysis suggested a greater increase in the amount of VPS4 bound to methacycline (76% over the lane 3 control) when compared to doxycycline (17% over the lane 3 control), suggesting differential affinity of the tetracycline antibiotics for VPS4 (second panel; FIG. 5C). Collectively, these results implicate VPS4 as a potential target of tetracycline class antibiotics, yield a potential mechanism of EV release inhibition.

Figure 6:
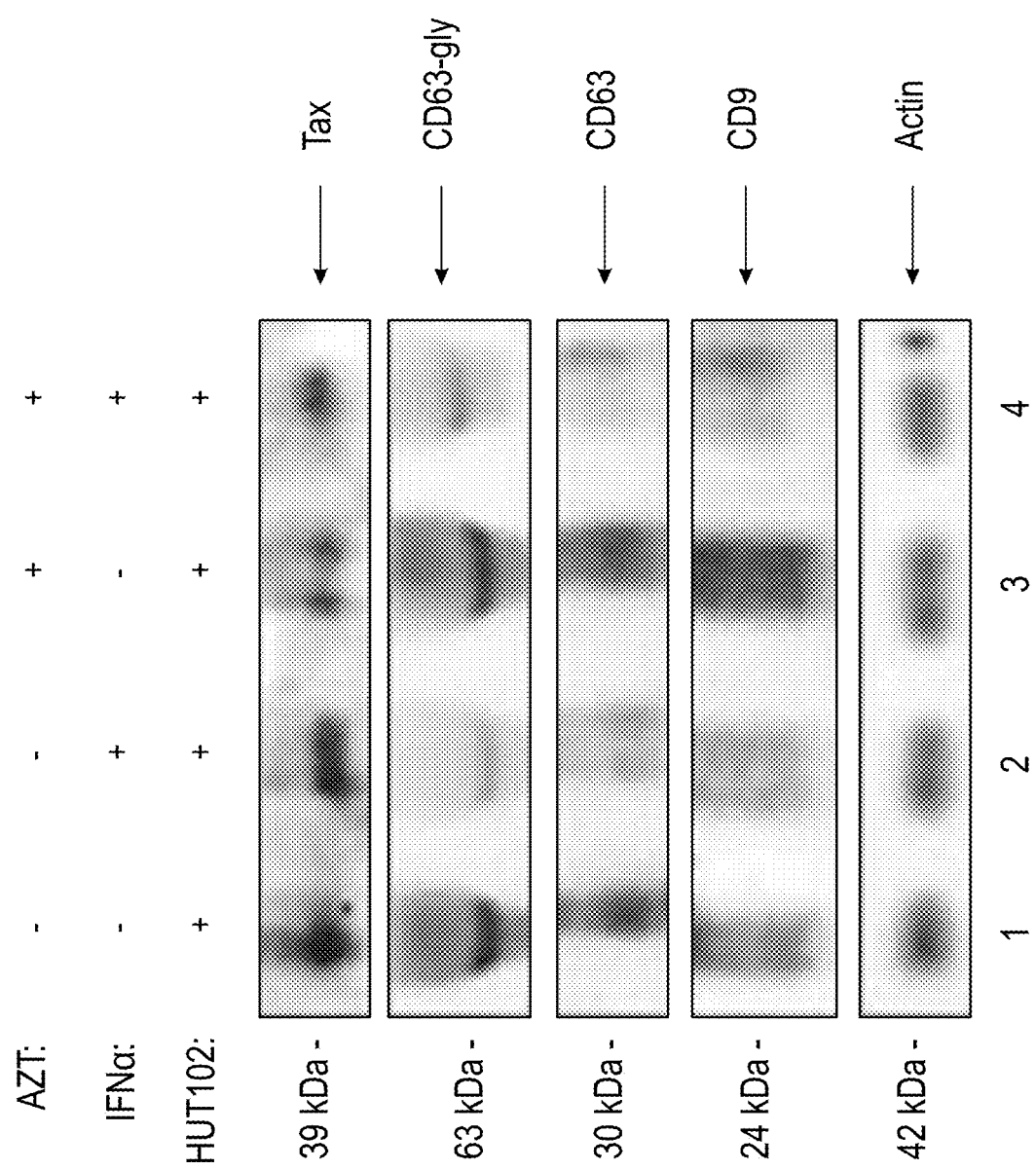
FIG. 6 shows that azidothymidine and Interferon-α modulated extracellular vesicle release by HTLV-1 infected T-cells. HTLV-1 infected T-cells (HUT 102) were treated with 10 μM AZT, 10K units of IFN-α, or a combination of the two for 5 days. Resulting supernatants were enriched for extracellular vesicles using NT80/82 and analyzed by Western blot for the presence of Tax, CD63, CD9, and Actin.

The incorporation of the human T-lymphotropic virus type 1 (HTLV-1) protein, Tax, into extracellular vesicles has been implicated in enhanced survival of recipient cells thereby contributing to a cancer phenotype. Applicant examined the effect of Azidothymidine (AZT) and interferon-α (IFN-α), both therapeutics commonly used in the treatment of HTLV-1, on the release of EVs from HTLV-1 infected cells. Here, HTLV-1 infected T-cells (HUT 102) were treated with 10 μM AZT, 10K units of IFN-α, or a combination of the two for 5 days. Resulting supernatants were enriched for extracellular vesicles using NT80/82 and analyzed by Western blot for the presence of Tax, CD63, CD9, and Actin. The results in FIG. 6 show that Tax was present in the EVs isolated from HTLV-1 infected cells and that IFN-α treatment decreases the amount of vesicles released from infected cells as indicated by a decrease in both CD63 and CD9, well known markers of exosomes (lane 2). Furthermore, the treatment of HTLV-1 infected cells with AZT resulted in an increase in the amount of vesicles release from infected cells as indicated by an increase in both CD63 and CD9 (lane 3). Finally, these results show that the combination of AZT and IFN-α synergistically reduced the release of EVs from HTLV-1 infected cells.

Taken together, these data suggest cannabinoids, azidothymidine/interferon, and tetracycline antibiotics possess therapeutic potential in the treatment of EV-associated pathogenesis, for example, HIV-associated dementia.

Example 2

Materials and Methods

One or more of the following materials and methods were used in the Examples of the present disclosure unless otherwise indicated.

Cell Culture and Reagents

U1 (HIV-1-infected promonocytic) and U937 cells were cultured in complete RPMI 1640 media with 10% fetal bovine serum (FBS), 1% L-glutamine, and 1% penicillin/streptomycin (Quality Biological) and incubated in 5% CO2 at 37° C. U1 cells were treated with varying concentrations of CBD (2-[1R-3-methyl-6R-(1-methylethenyl)-2-cyclohexen-1-yl]-5-pentyl-1,3-benzenediol; Cayman chemicals Cat. #90080) and THC (Δ9-tetrahydrocannabinol; NIDA Cat: 7370-023), as well as other drugs such as Flavopiridol hydrochloride hydrate (Cat: F3055; Sigma Aldrich), Rapamycin (Cat: Y-10219; MedChem Express), INK128 (Cat: A8551; APExBIO), Bafilomycin A1 (Cat: 54645; Cell Signaling Technology), SB 203580 (Cat: HY-10256; MedChem Express), and Wortmannin (Cat: W-2990; LC Laboratories). U1 and U937 cells were provided by the National Institutes of Health's (NIH) AIDS Reagent program.

A set of primary PBMCs were purchased (Precision For Medicine, Frederick, Md.) and cultured in vitro first with PMA/GM-CSF for 3 days to obtain macrophages. The suspension cells were then treated with PHA/IL-2 for 3 days to obtain activated T-cells. Both macrophages and T-cells were then infected with HIV-1 89.6 strain (MOI:1.0) for 6 or 12 d, respectively. The 6th-day cultures (T-cells) were then treated with cART for an additional 3 d to stop the spreading of the virus. On day 9, media was removed and CBD was added for another 3 days. The macrophages were also treated with PMA and GM-CSF during the infection period (added every 3 days into the fresh media). On day 12 post-infection, all cells were treated with a 10 µM cocktail (Lamivudine, Tenofovir, Emtricitabine, Indinavir) and kept in culture for another 3 days. On day 15, media was removed and CBD was added for 5 days (1, 5, 10 µM; at 0 and 48 h). All EV samples were collected using Nanotrap particles and processed for RNA analysis.

Patient Samples

Plasma specimens were obtained from 15 individuals, including 10 PWH with suppressed viral load on cART (n=5 *Cannabis* users and n=5 non-*Cannabis* users) and HIV-uninfected individuals (n=5 non-*Cannabis* users) at the Chronic Viral Illness Service/Centre for Innovative Medicine of the McGill University Health Centre (Montreal, Canada). This study was ethically approved by the Research Institute of the McGill University Health Centre Research Ethics Board (MUHC 15-031/18-3835). Written informed consent was obtained before enrolment. The research was conducted in accordance with the Helsinki Declaration.

ZetaView Nanoparticle Tracking Analysis (NTA)

NTA was performed with the ZetaView Z-NTA (Particle Metrix) and its software (ZetaView 8.04.02). The machine was calibrated according to manufacturer's protocol. Following the measurement and removal of any outliers from the measured 11 positions, the mean size (diameter; nm) and the concentration of the sample (EV number) were analyzed by the associated ZetaView software. Measurement data from the ZetaView were used to calculate averages and standard deviations from technical triplicates using Microsoft Excel 2016.

EV Enrichment Using Nanotrap Particles

EVs from small volume samples were enriched using Nanotrap particles (Ceres Nanosciences, Inc.) as previously described (Barclay et al., 2017, Exosomes from uninfected cells activate transcription of latent HIV-1. The Journal of Biological Chemistry, 292(28), 11682-11701; DeMarino et al., 2018, Antiretroviral Drugs Alter the Content of Extracellular Vesicles from HIV-1-Infected Cells. Scientific Reports, 8; Pleet et al., 2016, Ebola VP40 in Exosomes Can Cause Immune Cell Dysfunction. Frontiers in Microbiology, 7, 1765; Pleet, Erickson, et al., 2018, Ebola Virus VP40 Modulates Cell Cycle and Biogenesis of Extracellular Vesicles. The Journal of Infectious Diseases; Sampey et al., 2016, Exosomes from HIV-1-infected Cells Stimulate Production of Pro-inflammatory Cytokines through Trans-activating Response (TAR) RNA. The Journal of Biological Chemistry, 291(3), 1251-1266). Briefly, equal parts NT82 (Ceres #CN2010), NT80 (Ceres #CN1030), and 1×PBS without calcium or magnesium were combined and resuspended to create a 30% slurry. Twenty-five microliters of the NT80/82 slurry was added to 1 mL of culture supernatant and rotated overnight at 4° C. to enrich for EVs. The next day, the Nanotrap particles were pelleted, washed one time with 1×PBS without calcium or magnesium and used for further analyses.

RNA Isolation, Creation of cDNA, and Quantitative Real-Time PCR (RT-qPCR)

For the isolation of total RNA, cells were harvested, washed once in 1×PBS without calcium or magnesium and resuspended in 50 µL of 1×PBS. For the isolation of total RNA from EVs, Nanotrap particles were incubated and harvested as described above, then resuspended in 50 µL of 1×PBS without calcium or magnesium. Total RNA was isolated from cell pellets and NT80/82 pellets bound with EVs using Trizol Reagent (Invitrogen) as described by the manufacturer's protocol. cDNA was generated using GoScript Reverse Transcription Systems (Promega) using Envelope Reverse: (5'-TGG GAT AAG GGT CTG AAA CG-3' (SEQ ID NO:1); Tm=58° C.), and TAR Reverse: (5'-CAA CAG ACG GGC ACA CAC TAC-3' (SEQ ID NO:2), Tm=58° C.) primers. Serial dilutions of DNA from a CEM T-cell line containing a single copy of HIV-1 LAV provirus per cell (8E5 cells) were used as the quantitative standards. cDNA samples (2 µL/well) were plated into a Master Mix (18 µL/well) containing IQ Supermix (Bio-Rad), TAR Forward Primer (5'-GGT CTC TCT GGT TAG ACC AGA TCT G-3' (SEQ ID NO:3)), TAR Reverse Primer (5'-CAA CAG ACG GGC ACA CAC TAC-3' (SEQ ID NO:4)), and TAR Probe (5'56-FAM-AG CCT CAA TAA AGC TTG CCT TGA GTG CTT C-36-TAMSp-3' (SEQ ID NO:5)). RT-qPCR conditions were as follows: one cycle for 2 min at 95° C. followed by 41 cycles of 95° C. for 15 s and 58° C. for 40 s. Reactions were performed in triplicate using the BioRad CFX96 Real Time System. Quantitation was determined using cycle threshold (Ct) values relative to the 8E5 standard curve using the BioRad CFX Manager Software. Analysis of generated raw data was analyzed using Microsoft Excel 2016.

Preparation of Whole Cell Extracts

Infected U1 cell pellets were collected, washed with 1×PBS, and resuspended in 50 µL of lysis buffer [50 mM Tris-HCl (pH 7.5), 120 mM NaCl, 5 mM EDTA, 0.5% Nonidet P-40, 50 mM NaF, 0.2 mM $Na_3VO_4$, 1 mM DTT, and 1 complete protease inhibitor cocktail tablet/50 mL (Roche Applied Science)]. The mixture was incubated on ice for 20 min with vortexing every 5 min. Following incubation, the cell debris was separated by centrifugation for 10 min at 10,000×g. Protein concentrations of each cell lysate was determined using Bradford protein assay performed according to the manufacturer's protocol (Bio-Rad).

Western Blot

Laemmli buffer was added to sample cell lysates (10-20 µg) or NT80/82 pellets. Lysates were heated at 95° C. for 3 min and 15 µL of sample was loaded onto a 4-20% Tris/glycine gel (Invitrogen). When analyzing NT80/82 pellets, samples were heated at 95° C. for 3 min, vortexed, and then heated two additional times to release captured material from NT80/82 beads. Following the release of captured cargo, the total sample was then loaded on to a 4-20% Tris-Glycine gel (Invitrogen). Gels were run at 100 V and transferred onto Immobilon PVDF membranes (Millipore) at 50 mA overnight. Membranes were blocked in 5% milk in PBS with 0.1% Tween-20 (PBS-T) for 2 h at 4° C., then incubated overnight at 4° C. in PBS-T with the appropriate primary antibody ((α-p24 (Cat: 4121; NIH AIDS Reagent Program), α-Nef (Cat: 3689; NIH AIDS Reagent Program), α-gp120 (Cat: 522; NIH AIDS Reagent Program), α-CD81 (Cat: EXOAB-CD81A-1; SBI), α-VPS4 (Cat: sc-32922; Santa Cruz Biotechnology), α-CHMP6 (Cat: sc-67231; Santa Cruz Biotechnology), α-Actin (ab-49900; Abcam), α-CD63 (Cat: EXOAB-CD63A-1; Systems Biosciences), α-SQSTM1/p62 (Cat: 5114; Cell Signaling Technology), α-MAP LC3 α/β (Cat: sc-398822; Santa Crux Biotechnology), α-Alix (Cat: sc-49268; Santa Cruz Biotechnology), α-ATG12 (Cat: sc-271688; Santa Cruz Biotechnology), α-Beclin 1 (Cat: sc-48341; Santa Cruz Biotechnology)). Membranes were washed with PBS-T and incubated for 2 h with the indicated HRP-conjugated secondary antibody at 4° C. HRP luminescence was activated with Clarity Western ECL Substrate (Bio-Rad) and visualized by the Molecular Imager ChemiDoc Touch system (Bio-Rad).

Cell Viability Assay

Cells were cultured in RPMI with 10% exosome-free FBS at $10^6$ cells per well in 6 well plates. Cells were treated with 0.005% ethanol (control), CBD (1, 5 10, 50 μm) and THC (1, 5, 10, 50 μg/mL) once per day for 5 days. The MTT assay was used to measure cell death according to manufacturer's protocol (Sigma). After incubating with MTT solution for 2 h, the culture medium was aspirated and 1 mL of MTT solvent was added to each well. Cell viability was determined by the formation of formazan crystal and measured by absorbance at 590 nm and 620 nm, as previously described (Cotto et al., 2018, Cocaine and HIV-1 Tat Disrupt Cholesterol Homeostasis in Astrocytes: Implications for HIV-Associated Neurocognitive Disorders in Cocaine User Patients. Glia, 66(4), 889-902).

Chromatin Immunoprecipitation (ChIP)

Cells were harvested and washed with 1×PBS at 2000×g for 10 min. The cells were resuspended in 1% formaldehyde solution, made from 37% formaldehyde solution (Cat: F1635; Sigma-Aldrich) and exosome free RPMI media supplemented with L-glutamine, Penicillin/Streptomycin and FBS. Samples were rocked for 30 min at room temperature, and further processed using the Imprint Chromatin Immunoprecipitation Kit (Sigma). Next, the samples were sonicated, followed by an overnight 4° C. incubation while rotating with IgG and Pol II (serine 2/5) antibodies (10 μg). A 50% (v/v) protein A-Sepharose/protein G-Sepharose beads (A/G beads) (Calbiochem) was used to bind the complexes for a 2 h 4° C. incubation, rotating. Samples were washed three times with 1×PBS, and Proteinase K (800 U/mL) and crosslinking reversing solution (Sigma) was added for a 90 min at 65° C. DNA samples were washed and assayed for TAR DNA using qPCR analysis.

Kinase Assay

U1 cells ($5 \times 10^6$) were treated with CBD (1 μM) and THC 1 μg/mL) every day for 5 d. Cells were pelleted by centrifugation at 15,000×g for 5 minutes, washed with 1×PBS, and lysed in 250 μL lysis buffer. Lysates were immunoprecipitated with 10 μg of cdk9 or IgG antibodies overnight at 4° C., followed by a 2 h incubation with A/G beads at 4° C. IP complexes were washed with $TNE_{50}$+0.1% NP40 buffer and kinase buffer as described in (Guendel et al., 2014, Novel Neuroprotective GSK-3β Inhibitor Restricts Tat-Mediated HIV-1 Replication. Journal of Virology, 88(2), 1189-1208), followed by 1 h incubation period at 37° C. with $\gamma$-$^{32}$P ATP and purified histone H1. The samples (50%) were loaded and run through SDS-PAGE on a 4-20% Tris-Glycine gel, followed by staining with Coomassie blue, destain with destain buffer (50% methanol and 10% acetic acid), and dried for 2 h. The dried gels were exposed to a Phosphorlmager Cassette, followed by analysis via Molecular Dynamic's ImageQuant Software.

Neurospheres

Neural Progenitor Cells (NPCs; Cat: ACS-5003; ATCC) were grown using STEMdiff™ Neural Progenitor Medium (STEMCELL Technologies™) and differentiated into 3D neurospheres ($1 \times 10^5$ cells/well) using DMEM:F12 (Cat: 30-2006; ATCC)+Neural Progenitor Cell Dopaminergic Differentiation Kit (Cat: ACS-3004; ATCC) for an incubation period of 14 d. Inverted microscopy using Zen imaging software (Zeiss) was used to develop phase contrast images. Neurospheres were infected with HIV-1 89.6 dual-tropic strain (MOI: 10) and 10 μL of Infectin™ (Virongy, LLC) with a total volume of 200 μL, followed by 48 h incubation period. Neurospheres were then gently washed with 1×PBS±treated twice with 10 μM cocktail (Lamivudine, Tenofovir, Emtricitabine, Indinavir)±treatment (every other day) with a titration of CBD (5 and 10 μM) for a seven-day incubation period. Neurospheres were lysed in 100 μL lysis buffer and total lysates were run on a 4-20% Tris-Glycine SDS-PAGE, followed by western blot assessment. For RT-qPCR analysis, RNA was isolated from neurospheres, followed by RT-qPCR analysis.

Mass Spectrometry Analysis

HIV-1 infected U1 monocytes and U1 monocyte derived macrophages (MDMs) were cultured, followed by lysis of cell pellets. Each lysate sample (250 μg) was incubated with 100 μg of D-Biotin (ThermoFisher Scientific; Cat: B1595) or Biotinylated Cannabidiol (KareBay Biochem, Inc.), with a total volume of 800 μL, at 4° C. overnight. Streptavidin-Sepharose Beads (BioVision, Inc; Cat: 6565-2) (30 μL) were then added to each sample and incubated for 2 h at 4° C. The beads were pelleted through centrifugation at 15,000×g for 5 min. The supernatants were removed and the pellets were washed twice with $TNE_{300}$+0.1% NP40 buffer at 15,000×g for 5 min. The pellets were washed with 1×PBS at 15,000×g for 5 min and the supernatant was discarded. The pellets were treated with urea (8 M) and DTT (10 mM) to reduce samples, which were then alkylated with iodoacetamide (50 mM). The samples were then diluted by a solution of equal parts water and $NH_4HCO_3$ (500 mM). Samples were digested with trypsin (Promega) for 4 h at 37° C. Samples were then centrifuged at 12,000×g at room temperature for 10 min to remove beads, and the supernatants were cleaned with ZipTip. The peptide samples were dried and re-suspended in 0.1% TFA solution (10 μL), prior to loading into an Orbitrap Fusion mass spectrometer. Swiss-Prot and Proteome Discoverer (Thermo Scientific; version 1.3) softwares were used as previously described (Barclay et al., 2019, An Omics Approach to Extracellular Vesicles from HIV-1 Infected Cells. Cells, 8(8); DeMarino et al., 2018, Antiretroviral Drugs Alter the Content of Extracellular Vesicles from HIV-1-Infected Cells. Scientific Reports, 8).

Pathway Enrichment Analysis

Proteins with ≥2 peptide hit were included for enrichment analysis. Peptide hit filtered lists were used for removal of non-specific interactions by comparing D-Biotin to CBD-Biotin protein hits. Reactome pathway enrichment analysis was performed using an online tool named "g:Profiler" to determine pathways associated with proteins spectra retrieved from Mass spectrometry (Raudvere et al., 2019, g:Profiler: A web server for functional enrichment analysis and conversions of gene lists (2019 update). Nucleic Acids Research, 47(W1), W191-W198). For enrichment analysis, protein accession number were fed as an input with cut off threshold of 0.05 and run-on g:SCS alogrithm. g:SCS method is the default method for computing multiple testing correction for p-values gained from GO and pathway enrichment analysis, corresponds to an experiment-wide threshold of a=0.05, i.e., at least 95% of matsches above threshold are statistically significant. In result, enriched pathways are shown as bar graph between Reactome pathways identification number/name and negative p-value.

Densitometry Analysis

ImageJ software was used to conduct densitometry analysis on the kinase and western blot images. Background measurements were deducted from each lane to account for exposure, followed by normalization of each lane to each respective Actin measurements. The control lane (lane 1) was set to 100% to demonstrate a concise increase or decrease for the subsequent lanes. Percent changes were calculated by subtracting normalized lane measurements from the normalized control lane.

Statistical Analysis

Standard deviations were analyzed using Microsoft Excel software for quantitative experiments. Two-tailed Student's t-test was used to calculate p-values, where analysis was determined statistically significant when *p<0.05, p<0.01, and *p<0.001.

Example 3

Cannabidiol Inhibits the Release of EVs from HIV-1 Infected Monocytes

Figure 7:
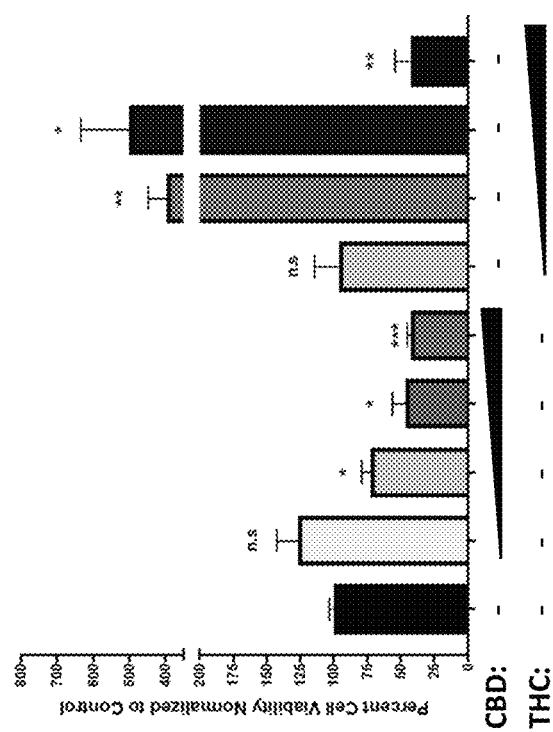
FIG. 7 is a graph showing cell viability analysis of cannabidiol components on HIV-1 infected monocytes. HIV-1 infected U1 monocytic cells ($1\times10^6$) were treated with CBD (green bars) at 1, 5, 10 and 50 μM) or THC (blue bars) at 1, 5, 10 and 50 μg/mL) every day for 5 days. Cell viability was determined using the MTT assay. Student's t-test was used for statistical analysis, where n.s is not significant, *p-value≤0.05; p-value≤0.01, *p-value≤0.001.
Figure 8C:
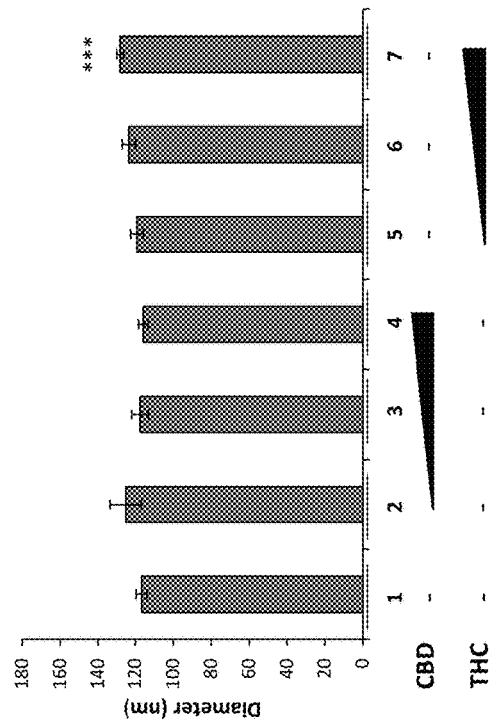
FIGS. 8A-8D are graphs showing *Cannabis* components lower EVs released from HIV-1 infected monocytes. HIV-1 infected U1 monocytic cells ($1\times10^6$) were treated with a titration of CBD (1, 5, and 10 μM) and THC (1, 5, and 10 μg/mL) every day for 5 days. Cells were pelleted and supernatant was used for Zetaview NTA analysis to determine (A) EV concentration, (B) median size, (C) mean size, and (D) peak size. Each bar represents an average of three independent replicates. Student's t-test was used for statistical analysis, where *p-value≤0.05; p-value≤0.01, *p-value≤0.001.
Figure 8D:
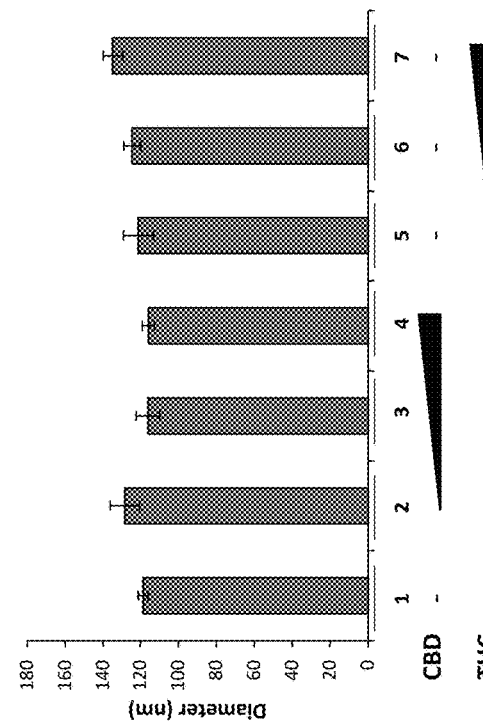
Figure 8A:
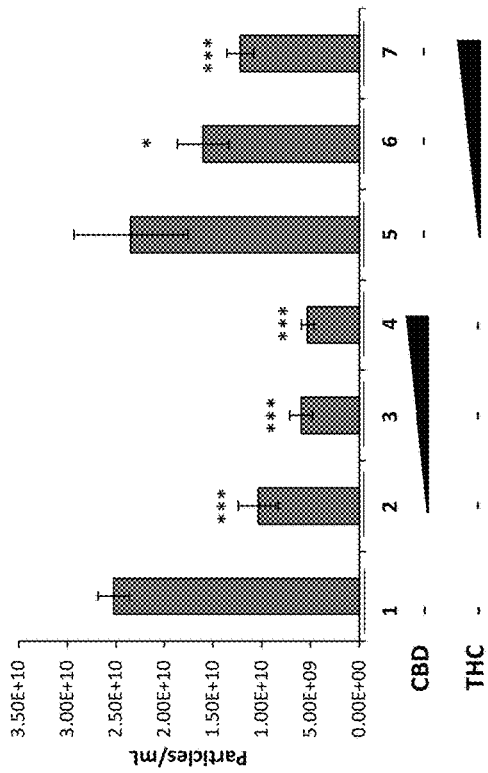

To determine whether CBD could mitigate the enhanced inflammation observed in PWH through modulation of EV release from infected cells, HIV-1 infected monocytes (U1) were treated twice with a titration of CBD (1, 5, and 10 µM) or a THC control (1, 5, and 10 µg/ml) over 5 days with no effects on cell viability (FIG. 7). Supernatants were harvested and analyzed using ZetaView NTA. The data in FIG. 8A suggests that treatment with CBD or THC results in a significant reduction in the number of EVs released from virally infected cells, specifically, treatment with CBD (1, 5, and 10 µM; lanes 2-4) resulted in a 44, 76, and 79% decrease in EVs, respectively, as compared to an untreated control. A similar, yet less drastic, trend was observed for THC treatments (1, 5, 10 µg/mL; lanes 5-7).

Figure 8B:
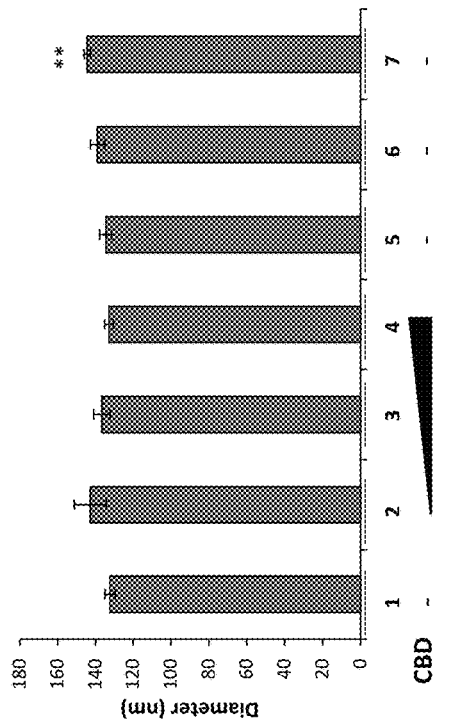

To verify that the observed decrease in EVs was not the result of modifications in packaging of various cargos into larger EVs, the mean diameter size (FIG. 8B), median diameter size (FIG. 8C), and peak diameter size (FIG. 8D) were also analyzed. Treatment with any of the concentrations of either cannabinoid (1, 5, and 10 µM or µg/mL, respectively) resulted in little to no change in diameter. Collectively, these results suggest that both THC and CBD (to a greater extent) reduce overall release of EVs.

Example 4

Cannabidiol Decreases EV-Associated Viral Proteins and Viral RNAs

To determine that cannabinoid treatment not only results in a reduction in EV number, but also a reduction in the presence of viral products, cells were treated twice with a titration of CBD or THC (1, 5, and 10 µM or µg/mL, respectively) and incubated for 5 days. Following incubation, supernatants were collected and EVs were enriched using NT80/82 particles, which have previously been shown to be effective in enriching EVs from low volume culture supernatants. Enriched samples were then analyzed by Western blot for the presence of EV marker and HIV-1 viral proteins. The data in FIG. 9A confirm the findings in FIG. 8A, as the levels of CD81, a tetraspanin protein associated with EVs, specifically exosomes, were decreased upon addition of CBD (1, 5, and 10 µM; lanes 2-4). The most drastic decrease in CD81 expression was achieved by low titer CBD which resulted in an 80% reduction as indicated by densitometry analysis (lane 2; FIG. 10A). Additionally, treatment with a titration of THC also elicited a decrease in CD81 (lanes 5-7).

The viral protein Nef is reported to be incorporated into EVs from numerous cell types, including astrocytes and microglia. Further evidence identified Nef as a potential contributor to HIV-1 pathogenesis through various mechanisms including the promotion of secreted proinflammatory cytokines, the suppression of neuronal action potentials, and disruption of the BBB. Data in FIG. 9A illustrates a dose-dependent decrease in EV-associated Nef (30 kDa) and its membrane-associated myristoylated Nef dimer (70 kDa) upon treatment with both CBD and THC. Densitometry analysis shown in FIG. 10B-C suggests there is a more drastic decrease in the lower molecular weight form of Nef (up to 79%, lane 3) as compared to the myristoylated dimer (up to 37%, lane 7). Interestingly, the greatest reduction of Nef (30 kDa) was achieved by administration of CBD, whereas the greatest reduction of myristoylated Nef dimer (70 kDa) was elicited by THC, potentially suggesting two different mechanisms of EV cargo modification.

CBD and/or THC, which target the same receptors as endocannabinoids, could also result in a reduction in EV-associated gp120. Results in FIG. 9A show a reduction in EV-associated gp120 ranging from 39-58% (FIG. 10D; lanes 2-4) with CBD treatment, suggesting a potential to mitigate the gp120-induced neuropathogenesis. Interestingly, the titration of both cannabinoids elicited an increase in the presence of gp160, the HIV-1 precursor glycoprotein. However, CBD induced an increase in gp160 by up to 125% (lane 4), whereas THC was less effective resulting in a maximum increase of 57% (lane 7), as measured by densitometry (FIG. 10E). This is in line with a corresponding decrease in the presence of the processed envelope glycoprotein, gp120, suggesting that both cannabinoids could potentially interfere with the proteolytic cleavage of HIV-1 precursor polyproteins, potentially through modulation of intracellular $Ca^{2+}$ levels as the primary endoprotease responsible for cleavage is a calcium-dependent enzyme. Therefore, CBD and/or THC may also contribute to the levels of EVs containing unprocessed glycoprotein and/or defective viral particles.

HIV-1 infection also leads to the incorporation of viral RNAs into EVs released from infected cells. HIV-1 TAR RNA is a short, non-coding RNA produced in infected cells as a result of non-processive transcription. We and other colleagues have found TAR RNA to be incorporated into EVs released from infected cells and can be detected in several biofluids at high copy numbers. TAR within EVs has been shown to expand viral pathogenesis through down-regulation of apoptosis, increased susceptibly to HIV-1 infection, and activation of TLR3 to subsequently stimulate the production of pro-inflammatory cytokines within uninfected recipient cells. To determine if cannabinoids possessed the potential to limit the incorporation of such RNAs into EVs, the same supernatants were enriched for EVs using NT80/82 particles, total RNA was isolated and subjected to RT-qPCR for the presence of TAR RNA, a short non-coding HIV-1 RNA, and viral full-length genomic RNA, env. The results in FIG. 9B show a dose-dependent decrease in the presence of EV-associated TAR RNA following addition of CBD (lanes 2-4), and to a lesser extent, THC (lanes 5-7). All doses of CBD elicited a reduction in TAR RNA as compared to the control (lane 1). A statistically significant decrease in TAR RNA within EVs was observed in the two highest concentrations (5 and 10 µM), which produced an average of 55%, and 86% reduction, respectively, from two replicates. Similarly, treatment with CBD and THC resulted in the reduction of env RNA within EVs (FIG. 9C). Taken together, these results indicate that CBD and THC decrease the number of EVs released from HIV-1 infected cells, which leads to a decrease in the amounts of viral products (protein and RNA) available to contribute to chronic inflammation.

To examine whether the same trend could be observed in a primary cell model, three independent HIV-1 infected primary macrophage cell cultures were treated with a titration of CBD (1, 5, and 10 uM). EVs were enriched from the extracellular supernatant using NT80/82 beads and analyzed for HIV-1 TAR and env (FIG. 11). Data in FIG. 11A demonstrates a relationship between increasing doses of CBD treatment and statistically significant decrease in TAR RNA within EVs from all three infected primary macrophages. Additionally, a similar statistically significant decreasing trend is observed with the amount of env RNA in secreted EVs released from two out of three infected primary macrophages (FIG. 11B). A similar trend was observed in EVs from HIV-1 infected primary macrophages treated with cART and CBD (FIGS. 12A-B) and EVs from HIV-1 infected primary T-cells treated with CBD alone (FIGS. 13A-B). To apply these findings to in vivo HIV-1 infection, total EVs were enriched from plasma samples from 15 individuals; 5 healthy donors, 5 HIV-1 positive donors, and 5 HIV-1 positive donors who used *Cannabis*, were trapped using NT80/82 particles and analyzed via Western blot for the presence of HIV-1 Nef protein. The results in FIG. 14 show a reduction in the presence of Nef protein in EVs isolated from HIV-1 infected individuals who used *Cannabis*. These results confirm that the cannabinoid CBD has the potential to decrease the release of EVs containing viral products from infected primary cells.

Example 5

Cannabinoids Inhibit HIV-1 Transcription in Monocytes

Given that our results indicate a reduction in EV release and EV-associated HIV-1 viral RNAs and proteins, we hypothesized that the observed reduction could be the result of changes in viral transcription resulting in a decreased production of viral products available for release from the cell in EVs. Therefore, U1 monocytes were treated with a titration of CBD (1, 5, 10 µM) and THC (1, 5, 10 µg/mL) every day for 5 days. Total RNA was isolated from the harvested cell pellets followed by RT-qPCR analysis of 3 independent replicates for TAR and env RNAs. Both TAR and env viral RNAs exhibited a dose-dependent decrease in response to CBD treatment (FIG. 15A; lanes 2-4 vs lane 1, with the highest dose (lane 4; 10 µM) resulting in a 95% and 96% decrease as compared to the untreated control. This may indicate that the reduction in secreted EV-associated viral TAR and env RNAs may be the result of CBD-mediated transcription inhibition. Interestingly, only treatment with the highest concentration of THC resulted in a significant decrease in env RNA. These results suggest that CBD has a more significant effect on viral transcription compared to THC. Furthermore, the reduction in both TAR and full length genomic (env) RNA suggest that CBD has the potential to inhibit viral transcription at the level of transcription initiation. Comparatively, the THC mediated reduction in full length genomic RNA but not TAR RNA suggests that THC may have a very modest impact on viral transcription elongation.

Figure 16A:
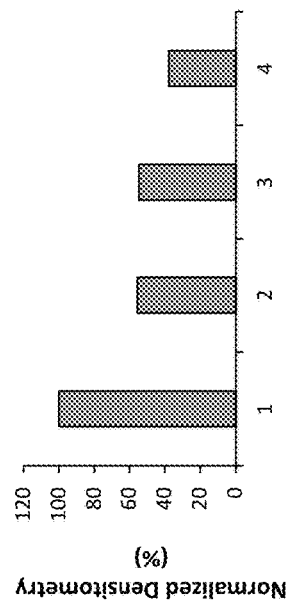
Figure 16B:
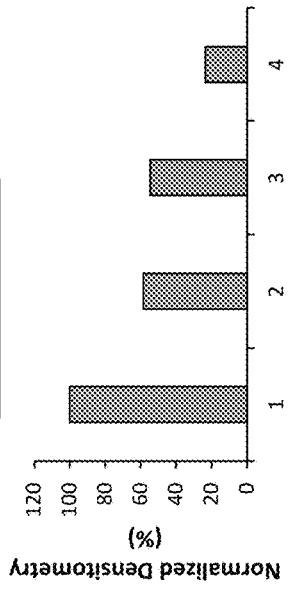
Figure 16C:
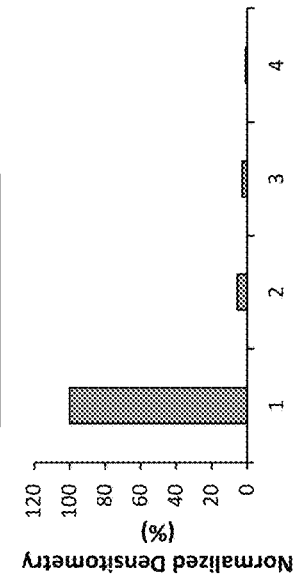
Figure 16D:
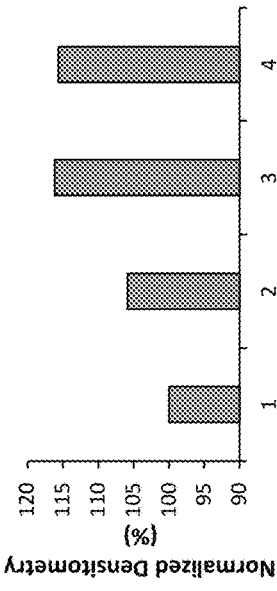
Figure 16E:
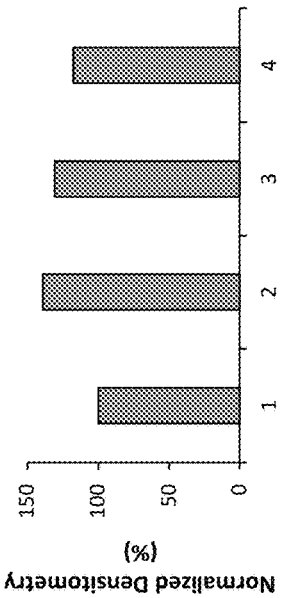

To verify that the CBD-mediated transcription inhibition resulted in a decrease in the production of viral proteins within HIV-1 infected cells, U1 cells were treated with a titration of CBD (1, 5, 10 µM) every day for 5 days and intracellular lysate was used for Western blot analysis of specific viral proteins, Nef, Pr55, and p24. As expected, intracellular levels of Nef, Pr55, and p24 proteins were downregulated post-CBD treatment in a dose dependent manner (FIG. 15B). The most significant reduction in all three viral proteins Pr55 (99%), p24 (76%), and Nef (62%) was observed with the 10 µM concentration of CBD (FIG. 16A-C). This is potentially due innate differences in the abundance of these mRNAs. Overall, there are typically fewer gag (Pr55/p24) mRNA transcripts within HIV-1 infected cells as compare to compared to nef mRNAs, which account for nearly 50% of all HIV-1 doubly spliced RNA in infected cells.

EVs consist of different subpopulations of vesicles which vary in size, biomarker characterization, and functionality. Previously, we have shown that one of the mechanisms by which exosomes (an EV subpopulation) are released, the endosomal sorting complexes required for transport (ES-CRT) pathway, is altered when HIV-1 infected cells are treated with combination antiretroviral therapy (cART) drugs (DeMarino et al., 2018). Briefly, the ESCRT pathway involves a series of interactions between four different ESCRT complexes (-0, -I, -II, -III), which contain a specific set of proteins to recruit exosomal cargo and promote intraluminal vesicular (ILV) budding inside multivesicular bodies (MVBs), as well as a VPS4 complex which disassociates ESCRT complexes post exosomal formation. The observed decrease in CD81 levels, an exosomal biomarker, as a result of CBD treatment and the decrease in EV concentration (FIGS. 7 and 8), suggest that the ESCRT pathway may be involved in the CBD-mediated changes in EV release and cargo. Western blot analysis of ESCRT proteins showed a slight increase in CHMP6, a protein involved in the ESCRT-III complex, and VPS4, a protein involved in exosomal membrane scission, indicating that the later stages of EV maturation may not be the target of CBD.

CBD-mediated transcription inhibition was further explored by investigating RNA polymerase II (Pol II) loading activity in comparison to a known transcription inhibitor, Flavopiridol HCl (Flavo), which has been shown to inhibit cyclin-dependent kinase 9 (cdk9)/Cyclin Ti complex activity. U1 monocytes were treated with CBD (10 µM) and Flavo (50 nM) for short periods (0, 2 and 6 hours) due to the fact that HIV-1 transcription activity is a rapid event that can be scored using chromatin immunoprecipitation (ChIP) assay for factor occupancy. Treated samples were lysed and incubated with IgG control and Pol II (serine 2/5) antibodies for ChIP, followed by qPCR analysis for TAR DNA. Data in FIG. 15C shows minimal TAR DNA for all of the IgG ChIPs, which served as a negative control. As expected, there was no change in amount of TAR DNA pulled down with PolII with any treatment compared to the untreated control at 0 hours samples (lanes 1-3). However, both the 2-hour and 6-hour Pol II pulldown samples showed statistically significant decreases of Pol II-associated TAR DNA when treated with CBD and Flavo in comparison to the untreated samples (lanes 4-6 and lanes 7-9), with Flavo exhibiting more effective inhibition in comparison to CBD. It is also important to note that CBD did not inhibit cdk9/Cyclin Ti activity in vitro, indicating that lower Pol II loading onto DNA may not be related to cdk9/Cyclin Ti kinase activity (FIG. 17). Collectively, these data indicate that CBD has a partial effect on HIV-1 transcription and Pol II loading. This data emphasizes the potential inhibitory nature of CBD (either direct or indirect) on serine 2/5 phosphorylated Pol II activity of HIV-1 viral transcription in monocytes.

Example 6

Cannabidiol Alters Intracellular and Secretory Autophagy Pathways

We have previously described a complex relationship between the intracellular autophagy pathway, secretory autophagy pathway, and EVs, where regulation of the autophagy pathway in infected cells can result in the blocking of viral protein degradation and, in turn, the export of viral products through EVs. Based on this, we next asked whether CBD had any effect on EV release by examining the secretory autophagy pathway. In order to evaluate the levels of intracellular autophagy proteins in HIV-1 infected cells, U1 cells were treated with CBD (10 μM) for 0, 6, 24, and 48 hours, followed by Western blot analysis for autophagosomal markers, p62 and LC3 I/II (FIG. 18A). The data indicates that, overtime, there was an increase in autophagosomal p62 production in the untreated samples (lanes 1, 3, 5, and 7). Conversely, a time dependent decrease of intracellular p62 with CBD treatment was observed, starting at the 24-hour (lane 5 vs lane 6) and peaking at 48-hour (lane 7 vs lane 8) timepoints. The normalized densitometry results of intracellular p62 is shown in FIG. 19. This decrease in SQSTM1/p62 protein, an autophagosome cargo adaptor protein which is degraded upon fusion of the autophagosome with the lysosome, suggests an increased autophagic flux in response to CBD treatment. A decrease in LC3 I levels was also observed in CBD treated samples up to 24 hours as compared to the untreated control, suggesting an increased conversion of LC3 I to LC3 II, which is indicative of elongation of the pre-autophagosomal membrane and is critical for the initiation of autophagy. This is further supported by the higher levels of LC3 II in CBD treated samples that is sustained at 6- and 24-hour as compared to their respective controls, further indicating active autophagosome formation in CBD treated samples. In order to examine any alterations that CBD might have on secretory autophagy in HIV-1 infected monocytes, EVs were enriched from the supernatants using NT80/82 and analyzed by Western blot for changes in secreted autophagosome proteins. As expected, there was increase in the levels of extracellular p62 in untreated controls (FIG. 19D, lanes 1, 3, 5, 7), suggesting an increase in the number of secreted autophagosomes over time as a result of virally-mediated autophagy inhibition observed in the intracellular protein levels. This is in line with numerous studies which have shown the HIV-1 viral proteins Tat and Nef to be involved in autophagy deregulation in infected cells. Furthermore, lower p62 levels were observed with CBD treatment from the 6-hour time point onwards compared to the untreated controls (lanes 3, 5, 7 vs 4, 6, 8; respectively), suggesting an overall decreased secretion of autophagosomes from HIV-1 infected cells. Additionally, there was an overall lower level of LC3 I in EVs secreted from CBD treated cells (lanes 3, 5, 7 vs 4, 6, 8; respectively). The Actin normalized densitometry analysis is shown in FIG. 19. Taken together, decreased p62 and LC3 levels in both intracellular and in secreted autophagosome vesicles suggests that CBD may activate the autophagy pathway thereby lowering overall secretory autophagy.

To determine the specific points at which CBD inhibits intracellular and extracellular autophagosome formation and secretion, we compared CBD treatment of U1 monocytes with known inhibitors of different points in the autophagy pathway. Cell viability was assessed among a panel of titrated autophagy drugs and the least toxic concentration per drug was utilized (FIG. 20). We treated U1 cells with CBD (10 μM) every day, Rapamycin (50 nM), INK128 (50 nM), Bafilomycin A1 (50 nM), SB 203580 (20 μM), or Wortmannin (2 nM) for 5 days. Our rationale for using these drugs was that they regulate different steps of autophagy including nucleation inhibition by inhibiting MTOR activity (Rapamycin, INK128) or by inhibiting pre-autophagosomal VPS34 complex activity (Wortmannin, SB 203580), and autophagosome-lysosome fusion inhibition (Bafilomycin A1). Therefore, a side-by-side comparison to CBD would potentially allow for a better definition of which step of autophagosome formation is primarily regulated by CBD. U1 cells were treated with the autophagy regulators and harvested along with their corresponding supernatants for further analysis using Western blot against p62, LC3, ATG12-ATG5 complex, free ATG12, Beclin-1, and Actin. Results in FIG. 18B (intracellular proteins, top panel) show autophagy protein profiles associated with the various autophagy regulators. Interestingly, the autophagy protein profile resulting from treatment with CBD most closely reflected the profile exhibited by cells treated with the autophagy inducers, rapamycin and INK128 (lanes 2-4) as indicated by the low levels of LC3 I and ATG12-ATG5, and by high levels of Beclin-1. The corresponding supernatants were enriched for EVs and also analyzed for the presence of autophagy proteins. Treatment with CBD, rapamycin, and INK128 resulted in a reduction of EV-associated p62 and LC3 I levels (FIG. 18A, lower panel, lanes 2-4). Conversely, treatment with autophagy inhibitors, Bafilomycin A1, SB 203580, and Wortmannin (FIG. 18B, lower panel, lanes 5-7) resulted in sustained levels of EV-associated p62, elevated levels of LC3 I and -II as compared to the untreated, HIV-1 infected control (lane 1). Little to no change in EV-associated levels of ATG12-ATG5, and Beclin-1 was observed with any treatment. The Actin normalized densitometry analysis is shown in FIG. 21. Collectively, these data indicate that CBD may promote activation of the autophagy pathway, potentially at the level of upstream mTOR signaling and/or pre-autophagosome formation.

Example 7

Cannabidiol Reduces Production of Viral Products in a 3D Neurosphere Model

In recent years, three-dimensional (3D) culture systems have emerged as reliable in vitro tools for studying not only normal developmental processes but also disease modeling and drug discovery. Generally speaking, the 3D architecture provides a more tissue-like environment in which cell-to-cell and cell-to-matrix interactions are expected to more closely mimic the in vivo phenotype (Pampaloni et al., 2007, The third dimension bridges the gap between cell culture and live tissue. Nature Reviews. Molecular Cell Biology, 8(10), 839-845). Additionally, these cultures may express more biologically relevant responses to diffusible factors, such as drugs of abuse.

With respect to the CNS, induced pluripotent stem cells (iPSCs) have been widely used to study several different neuropathologies ranging from neurodegenerative disorders to neurotrophic viruses. More recently, others have utilized iPSC-derived neural progenitor cells (NPCs) to generate 3D neurospheres that are susceptible to viral infection, including Zika virus and Herpes Simplex Virus 1. For these reasons, we chose to utilize a similar platform to potentially model HIV-1 infection as well as the effects of treatment with both antiretroviral compounds and CBD.

Figure 22B:
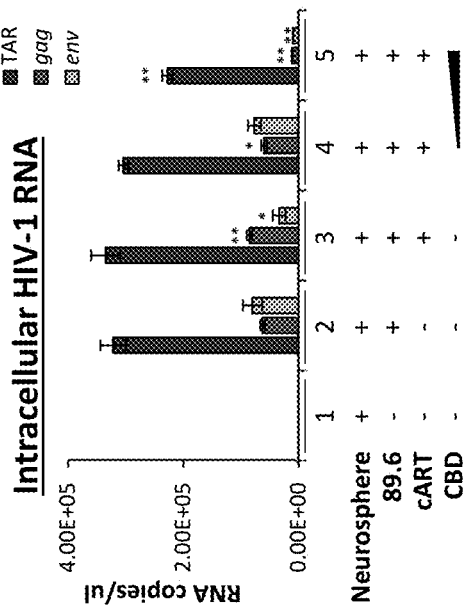
Figure 22D:
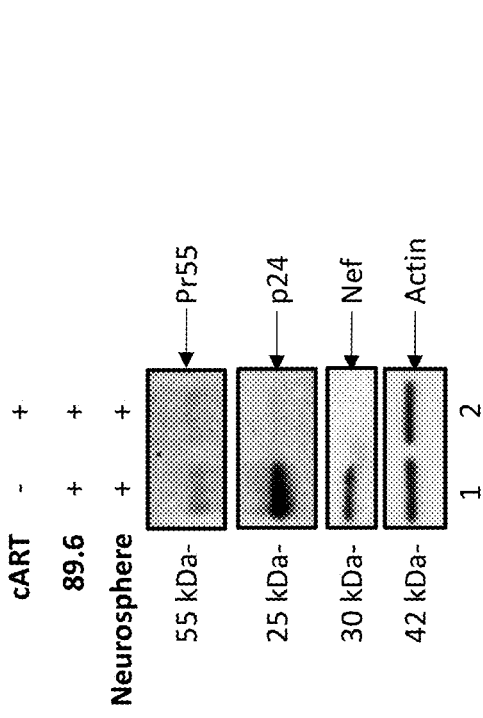
Figure 22A:
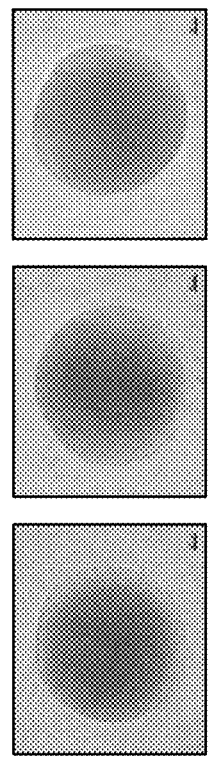

Here, commercially available NPCs were used to establish neurospheres for infection. The diagram in FIG. 22A provides a high-level summary of the workflow involved in this process, which utilized CD34+ cells as the original starting material to generate iPSCs, followed by embryoid body formation, and then differentiation into NPCs. To induce neurosphere formation, approximately $1\times10^5$ NPCs were individually seeded in U-shaped wells. After approximately 48 hours of incubation, NPCs had self-aggregated into well-defined neurospheres. Representative images in FIG. 22B show the appearance of three individual neurospheres, which clearly demonstrate their uniform shape and structure.

Figure 22C:
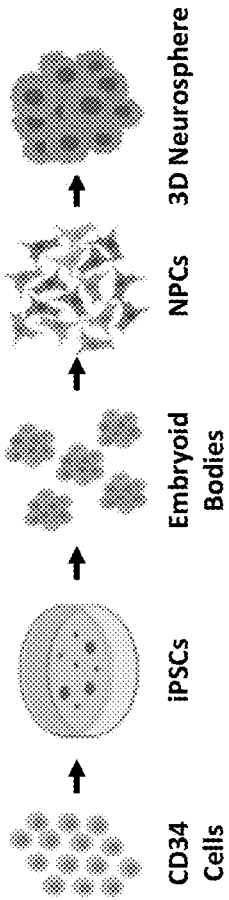

To determine if neurospheres were susceptible to HIV-1 infection, differentiated neurospheres were cultured with HIV-1 dual tropic 89.6 with or without the addition of cART cocktail (10 µM; Tenofovir, Emtricitabine, Lamuvidine, and Indinavir) for a period of seven days. Neurospheres were then harvested for downstream experiments. To evaluate the extent of viral replication, Western blot was performed to assess the relative expression levels of HIV-1 viral proteins. As shown in FIG. 22C, expression of Pr55, p24, and Nef proteins were detected in neurospheres cultured with HIV-1 89.6 (lane 1). In contrast, the presence of cART resulted in a reduction in all three viral proteins, with the most drastic decrease being observed in p24 (92%) and Nef (98%). This data was validated via densitometry analysis by normalizing expression levels to Actin (FIG. 23). Overall, this data suggests that NPC-derived neurospheres can harbor replicating HIV-1 and, furthermore, highlights the efficacy of cART in a 3D model.

Next, the levels of intracellular viral RNA transcripts were assessed to determine the effects of CBD treatment on HIV-1 infected neurospheres. Prior to these experiments, the expression of relevant receptors in neurospheres were confirmed including Cannabinoid receptors CB1 and CB2, as well as the serotonin receptor 5-HT1A and the Vanilloid receptor which have been previously found to bind cannabinoids (FIG. 24). We then performed RT-qPCR analysis to quantify the expression of TAR, gag, and env. Data in FIG. 22D shows that upon cART treatment, there was a significant decrease in gag and env RNA relative to HIV-1 89.6 alone (lanes 2 vs. 3), potentially suggesting that cART treatment of neurospheres lowers only full length genomic viral RNAs while not affecting short non-coding RNAs. Interestingly, treatment of HIV-1 infected neurospheres with CBD (10 µM) resulted in a signification reduction of all three viral transcripts (FIG. 22D, lanes 3 vs 5). This data suggests that CBD (10 µM) may serve as an optimal concentration for 3D models and, furthermore, demonstrates that CBD in combination with cART may be more effective at reducing viral transcription than cART alone. In conclusion, these data emphasize the potential of CBD for mitigating the inflammation and neuronal degradation associated with HIV-1.

Discussion

The examples and studies of the present disclosure demonstrate, among other things, that both cannabinoids independently reduce the number of EVs released from HIV-1 infected myeloid cells. In addition, a decrease in copy number of HIV-1 RNAs, TAR and genomic env, packaged into EVs was observed, suggesting that cannabinoids have therapeutic potential in mitigating inflammation during infection.

In long-term HIV-1 infections, several HIV-1 proteins and RNAs have been found in the CSF of HIV-1 infected individuals potentially owing to increased protein half-life through modifications inhibiting their reuptake and encapsulation in EVs such as exosomes. As a result of their increased half-life, viral proteins accumulate in the extracellular space within the CNS and as well as traverse the BBB via absorptive endocytosis to elicit neuroinflammation through interactions with microglia, astrocytes, and neurons. Although cART is effective for suppressing viremia, a shift in the neurocognitive symptoms with existing regimens indicates potential changes in neuropathogenic mechanisms in treated patients. This, coupled with the fact that these proteins and RNAs continue to be produced despite cART suggests a gap in current cART regimens which implies the need for the development of new therapeutics with high CNS penetrance designed to degrade or inhibit soluble/EV-associated viral proteins and RNAs. The highly lipophilic nature of cannabinoids makes them ideal candidates for the treatment of HIV-1 associated neurocognitive deficits.

In the studies and examples of the present disclosure, the use of cannabinoids as a potential EV-modulator (FIG. 8) was investigated. The highly lipophilic nature of cannabinoids makes them ideal candidates for the treatment of EV-associated neurological complications of infection, particularly HIV-1 associated neurocognitive deficits. The reduction of both viral proteins and RNA (FIGS. 9 and 11) by low dose CBD points to the widespread potential of CBD to combat inflammation in HIV-1 patients both within the CNS and peripherally. This is in line with studies which have shown an association between lower counts of $CD16^+$ monocytes (which facilitate entry of the HIV-1 virus into the CNS) and use of *Cannabis*. The inhibition of EV release from circulating monocytes and immune-competent cells of the CNS such as microglia, perivascular macrophages, and pericytes, could potentially mitigate the levels of chemokine and cytokine released from these cells as various proinflammatory molecules have been found to be associated with EVs. This diminished release of inflammatory factors would release in a decrease in the activation of astrocytes, which serve as expanders of neuroinflammation in HIV, numerous other infections, and several CNS-related diseases.

While decades of research have led to great advances in the treatment of HIV-1 allowing for adequate suppression of the virus, improved quality of life, and a longer life span, there is currently no HIV-1 transcription inhibitor included in antiretroviral therapies. This gap allows for persistent HIV-1 transcription with occasional full length read throughs which can result in the production of fully infectious virus. The presented data suggests CBD and THC have the potential to inhibit HIV-1 transcription (FIG. 11). Interestingly, these two cannabinoids likely have different mechanisms by which they alter viral transcription with CBD likely acting at the level of transcription initiation and THC acting on transcription elongation. These findings are supported by differences in the transcriptional regulation of cellular genes in myeloid cells by CBD and THC. These studies have found CBD to increase the expression of negative regulators of transcription factors NF-kB and AP-1, both of which can bind the HIV-1 promoter.

Viruses have evolved mechanisms by which they can hijack numerous host cell pathways, to promote pathogenesis. HIV-1 accessory proteins such as Nef, Tat, and Vif have been shown to inhibit nearly all stages of autophagy, including nucleation, sequestration, elongation of the phagophore, and autophagosome-lysosomal fusion for the purpose of preventing host cell-mediated degradation of viral products. Inhibition of the cell degradation pathway induces accumulation of the excess host cellular products, as well as accumulation of the viral RNAs and proteins in the cytosol.

We have shown that through CBD-mediated activation of the intracellular autophagy pathway (FIG. 18), the host cell degradation pathway continues to degrade viral proteins and RNAs, which may contribute to the lowered incorporation of viral proteins and RNAs in EVs (seen in FIGS. 9 and 11) thereby limiting HIV-1 pathogenesis. When the relationship between CBD and autophagy was investigated using a biotinylated-CBD pull-down from U1 monocytes and monocyte-derived macrophages for mass spectrometry analysis, reactome pathway enrichment analysis showed significant enrichment of proteins in reactome autophagy pathways (Macrophage: R-HSA-9663891, R-HSA-1236974, R-HSA-1632852, R-HSA-9612973; Monocyte: R-HSA-9646399, R-HSA-9663891, R-HSA-9612973, R-HSA-1632852, R-HSA-9613829, FIG. 25).

Few studies have utilized 3D organoids to study systematic pathogenesis progression within particular organs. More specifically, development of CNS organoids have been increasingly crucial for the examination of neurodegenerative diseases, such as HAND, amyotrophic lateral sclerosis, and multiple sclerosis, as invasive surgeries for CNS are less than optimal for living patients exhibiting neurodegeneration. Our study showed the expression of endocannabinoid receptors in the 3D neurospheres, which implies promising potential for CBD and THC drug delivery (FIG. 25). Additionally, successful infection of the 3D neurosphere and lowering of its viral products by CBD indicates the potential CBD has in lowering EV-associated viral products in a systematic HIV-1 infected organoid model (FIG. 22). It is important to note that the high density and tight junctions formed throughout the neurosphere may affect CBD uptake to certain regions of the neurosphere, which may potentially contribute to the low efficacy of lower concentrated CBD treatment seen in altering viral transcripts. Although more research is needed to examine the characteristics, viral infection, and drug uptake on the 3D neurospheres, the impact of CBD-mediated lowered viral transcription in neurospheres (FIG. 22) combined with CBD-mediated lowered incorporation of viral RNAs in EVs from HIV-1 infected patients undergoing *Cannabis* treatment (FIG. 14) implies the potential for cannabinoid-induced lowering of neuroinflammation seen in HAND.

Although this study focuses on EVs released from HIV-1 infected cells, these findings can be applied to any EV-mediated dysfunction. While not wishing to be bound by theory, the statistically significant reduction in EV release suggests that cannabinoids, particularly CBD, exert its anti-inflammatory effects by limiting EV release, thereby broadening the application of these findings not only to other infectious diseases but also to any diseases with an inflammatory component.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention. The appended claims are intended to be construed to include all such embodiments and equivalent variations.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, patents, and other references mentioned herein are expressly incorporated by reference in their entirety, including all formulas and figures, to the same extent as if each were incorporated by reference individually. In case of conflict, the present specification, including definitions, will control.

What is claimed is:

1. A pharmaceutical composition comprising a cannabinoid product in an effective amount sufficient to inhibit release of extracellular vesicles from a cell infected by a virus, wherein the cell is a neuron, an astrocyte, an oligodendrocyte, or a microglia, and wherein the virus is a human immunodeficiency virus (HIV) or a human T-cell leukemia-lymphoma virus (HTLV).

2. The pharmaceutical composition of claim 1, further comprising azidothymidine, an interferon ("IFN"), a tetracycline antibiotic, or the combination thereof.

3. The pharmaceutical composition of claim 1, wherein the cannabinoid product comprises a pentyl side chain on an aromatic ring or a propyl side chain on an aromatic ring.

4. The pharmaceutical composition of claim 1, wherein the cannabinoid product comprises tetrahydrocannabinol (THC), cannabidiol (CBD), olivetol, cannabinol (CBN), cannabigerol (CBG), cannabichromene (CBC), cannabicyclol (CBCL), nabilone, tetrahydrocannabinolic acid (THCA), cannabichromenic acid (CBCA), cannabicyclolic acid (CBCLA), cannabigerolic acid (CBGA), cannabidiolic acid (CBDA), cannabinolic acid (CBNA), tetrahydrocannabivarin (THCV), cannabivarin (CBV), cannabidivarin (CBDV), cannabigerovarin (CBGV), cannabichromevarin (CBCV), cannabicyclovarin (CBCLV), cannabicyclovarinic acid (CBCLVA), cannabigerovarinic acid (CBGVA), tetrahydrocannabivarinic acid (THCVA), cannabichrome varinic acid (CBCVA), cannabidivarinic acid (CBDVA), or a combination thereof.

5. The pharmaceutical composition of claim 1, wherein the cannabinoid compound comprises CBD, THC, or a combination thereof.

6. The pharmaceutical composition of claim 2, wherein the IFN comprises IFN-α, IFN-β, IFN-ε, IFN-κ, IFN-ω, IFN-γ, IFN-λ1, IFN-λ2, and IFN-λ3; and wherein the tetracycline antibiotic comprises tetracycline, chlortetracycline, oxytetracycline, demeclocycline, doxycycline, lymecycline, meclocycline, methacycline, minocycline, rolitetracycline, tigecycline, or a combination thereof.

7. The pharmaceutical composition of claim 1 further comprising azidothymidine, an interferon ("IFN"), a tetracycline antibiotic, an anti-inflammatory agent, a neurotrophic factor, a neuroprotective agent, or a combination thereof.

8. The pharmaceutical composition of claim 7, wherein the anti-inflammatory agent is GFβ, IL-2, IL-17, IL-35, or IL-37; and wherein the neurotrophic factor is BDNF, NGF, Neurotrophin-3, FGF2, CTNF, GDNF, IGF2, HGF, Noggin, or T3.

9. The pharmaceutical composition of claim 1, further comprises a pharmaceutically acceptable carrier.

10. A method for treating a viral disease in a subject in need thereof, comprising
administering to the subject a therapeutically effective amount of a pharmaceutical composition comprising a cannabinoid product in an effective amount sufficient to inhibit release of extracellular vesicles from a cell infected by a virus,
wherein the cell is a neuron, an astrocyte, an oligodendrocyte, or a microglia, and
wherein the virus is a human immunodeficiency virus (HIV) or a human T-cell leukemia-lymphoma virus (HTLV).

11. The method of claim 10, wherein the viral disease is a neurological disorder; is associated with HIV-1 and/or HTLV-1; or comprises Alzheimer's disease, multiple sclerosis, stroke, or a combination thereof.

12. The method of claim 11, wherein the neurological disorder comprises viral meningitis, viral encephalitis, postherpetic neuralgia, HIV-associated neurocognitive disorders, HTLV-1 associated myelopathy, poliomyelitis, influenza, Reye's Syndrome, Meniere's Disease, trigeminal neuralgia, or herpes zoster.

13. The method of claim 12, wherein the HIV-associated neurocognitive disorder comprises asymptomatic neurocognitive impairment (ANI), minor neurocognitive disorder (MND), minor cognitive motor disorder (MCMD), HIV-associated dementia (HAD), HIV-associated myelopathy, HIV-associated peripheral neuropathy, or a combination thereof.

14. A method of reducing damage to a neuron from central neural system ("CNS") or treating neuroinflammation in a subject in need thereof, comprising
    administering to the subject a therapeutically effective amount of a pharmaceutical composition comprising a cannabinoid product in an effective amount sufficient to inhibit release of extracellular vesicles from a cell infected by a virus,
    wherein the cell is a neuron, an astrocyte, an oligodendrocyte, or a microglia, and
    wherein the virus is a human immunodeficiency virus (HIV) or a human T-cell leukemia-lymphoma virus (HTLV).

15. The method of claim 14, wherein the damage is caused by infection of the subject with a HIV and/or HTLV-1.

16. A method of inhibiting transcription of a viral RNA comprising contacting the cell with the pharmaceutical composition of claim 1.

17. A method of inhibiting release of extracellular vesicles from a cell infected by a virus, comprising contacting the cell with the pharmaceutical composition of claim 1.

18. The method of claim 17, wherein the extracellular vesicles comprise an exosome and/or a microvesicle.

* * * * *